(12) United States Patent
Karasawa

(10) Patent No.: US 9,694,578 B2
(45) Date of Patent: Jul. 4, 2017

(54) LIQUID EJECTION CONTROL APPARATUS, LIQUID EJECTION SYSTEM, AND CONTROL METHOD

(71) Applicant: SEIKO EPSON CORPORATION, Tokyo (JP)

(72) Inventor: Junichi Karasawa, Shimosuwa-machi (JP)

(73) Assignee: SEIKO EPSON CORPORATION, Tokyo (JP)

( * ) Notice: Subject to any disclaimer, the term of this patent is extended or adjusted under 35 U.S.C. 154(b) by 0 days.

(21) Appl. No.: 15/268,564

(22) Filed: Sep. 17, 2016

(65) Prior Publication Data

US 2017/0080710 A1    Mar. 23, 2017

(30) Foreign Application Priority Data

Sep. 18, 2015  (JP) ................. 2015-185396

(51) Int. Cl.
*B41J 2/045* (2006.01)
*A61B 17/3203* (2006.01)

(52) U.S. Cl.
CPC ....... *B41J 2/04588* (2013.01); *B41J 2/04581* (2013.01)

(58) Field of Classification Search
CPC ............. B41J 2/04588; B41J 2/04581; A61B 17/3203; A61B 17/32037; A61B 2/04581; A61B 2017/0019; A61B 2017/00154; A61B 2017/00181; A61B 2017/0017; A61B 2017/00185

See application file for complete search history.

(56) References Cited

U.S. PATENT DOCUMENTS

| | | | |
|---|---|---|---|
| 9,289,228 B2 | 3/2016 | Seto et al. | |
| 2015/0073452 A1* | 3/2015 | Uchida | A61B 17/3203 606/167 |
| 2015/0224527 A1 | 8/2015 | Kojima et al. | |
| 2016/0185106 A1 | 6/2016 | Karasawa | |
| 2016/0185107 A1 | 6/2016 | Karasawa | |
| 2016/0185108 A1 | 6/2016 | Karasawa | |
| 2016/0185109 A1 | 6/2016 | Karasawa | |
| 2016/0221335 A1 | 8/2016 | Karasawa | |
| 2016/0221336 A1 | 8/2016 | Karasawa | |

FOREIGN PATENT DOCUMENTS

| | | |
|---|---|---|
| JP | 2005-152127 A | 6/2005 |
| JP | 2009-039384 A | 2/2009 |
| JP | 2011-036533 A | 2/2011 |
| JP | 2016-016284 A | 2/2016 |
| JP | 2016-027838 A | 2/2016 |

(Continued)

*Primary Examiner* — Julian Huffman
(74) *Attorney, Agent, or Firm* — Maschoff Brennan

(57) ABSTRACT

A liquid ejection control apparatus, which controls a drive voltage waveform applied to a piezoelectric element so as to control ejection of a pulsed liquid jet, includes a first operation unit that receives input of an index value for setting a position of an inflection point in a rising portion of the drive voltage waveform, and a control unit that sets the position of the inflection point in the rising portion of the drive voltage waveform according to the index value so as to control changing of the drive voltage waveform.

15 Claims, 53 Drawing Sheets

(56) References Cited

FOREIGN PATENT DOCUMENTS

| | | |
|---|---|---|
| JP | 2016-120023 A | 7/2016 |
| JP | 2016-120024 A | 7/2016 |
| JP | 2016-120066 A | 7/2016 |
| JP | 2016-120067 A | 7/2016 |
| JP | 2016-140551 A | 8/2016 |
| JP | 2016-140552 A | 8/2016 |

* cited by examiner

FIG.37

PARAMETER TABLE 510

| ENERGY DIAL POSITION 511 | ENERGY INDICATION VALUE 512 | CUTTING TYPE DIAL POSITION (R VALUE: INFLECTION POINT INDICATION VALUE) 513 | VOLTAGE AMPLITUDE 514 | REPETITION FREQUENCY 516 | RISING FREQUENCY 518 |
|---|---|---|---|---|---|
| 1 | E001 | R=0.1 | Vm11 | Fp11 | Fpr11 |
|   |      | R=0.3 | Vm13 | Fp13 | Fpr13 |
|   |      | R=0.5 | Vm15 | Fp15 | Fpr15 |
|   |      | R=0.7 | Vm17 | Fp17 | Fpr17 |
|   |      | R=0.9 | Vm19 | Fp19 | Fpr19 |
| 2 | E002 | R=0.1 | Vm21 | Fp21 | Fpr21 |
|   |      | R=0.3 | Vm23 | Fp23 | Fpr23 |
|   |      | R=0.5 | Vm25 | Fp25 | Fpr25 |
|   |      | R=0.7 | Vm27 | Fp27 | Fpr27 |
|   |      | R=0.9 | Vm29 | Fp29 | Fpr29 |
| 3 | E003 | R=0.1 | Vm31 | Fp31 | Fpr31 |
|   |      | R=0.3 | Vm33 | Fp33 | Fpr33 |
|   |      | R=0.5 | Vm35 | Fp35 | Fpr35 |
|   |      | R=0.7 | Vm37 | Fp37 | Fpr37 |
|   |      | R=0.9 | Vm39 | Fp39 | Fpr39 |
| ... | ... | ... | ... | ... | ... |

FIG.41

PARAMETER TABLE 510B

| ENERGY DIAL POSITION 511 | ENERGY INDICATION VALUE 512 | REPETITION FREQUENCY DIAL POSITION 515 | REPETITION FREQUENCY 516B | CUTTING TYPE DIAL POSITION 513 | VOLTAGE AMPLITUDE 514 | RISING FREQUENCY 518 |
|---|---|---|---|---|---|---|
| 1 | E001 | 1 | Fp11 | R=0.1 | Vm111 | Fpr111 |
| | | | | R=0.3 | Vm113 | Fpr113 |
| | | | | R=0.5 | Vm115 | Fpr115 |
| | | | | R=0.7 | Vm117 | Fpr117 |
| | | | | R=0.9 | Vm119 | Fpr119 |
| | | 2 | Fp12 | R=0.1 | Vm121 | Fpr121 |
| | | | | R=0.3 | Vm123 | Fpr123 |
| | | | | R=0.5 | Vm125 | Fpr125 |
| | | | | R=0.7 | Vm127 | Fpr127 |
| | | | | R=0.9 | Vm129 | Fpr129 |
| | | 3 | Fp13 | R=0.1 | Vm131 | Fpr131 |
| | | | | R=0.3 | Vm133 | Fpr133 |
| | | | | R=0.5 | Vm135 | Fpr135 |
| | | | | R=0.7 | Vm137 | Fpr137 |
| | | | | R=0.9 | Vm139 | Fpr139 |
| | | ... | ... | ... | ... | ... |
| ... | ... | ... | ... | ... | ... | ... |

FIG.45

PARAMETER TABLE 510C

| ENERGY DIAL POSITION 511 | ENERGY INDICATION VALUE 512 | REPETITION FREQUENCY DIAL POSITION 515 | REPETITION FREQUENCY 516B | RISING FREQUENCY DIAL POSITION 517 | RISING FREQUENCY 518C | CUTTING TYPE DIAL POSITION 513 | VOLTAGE AMPLITUDE 514 |
|---|---|---|---|---|---|---|---|
| 1 | E001 | 1 | Fp11 | 1 | Fpr111 | R=0.1 | Vm111 |
|   |   |   |   |   |   | R=0.3 | Vm113 |
|   |   |   |   |   |   | R=0.5 | Vm115 |
|   |   |   |   |   |   | R=0.7 | Vm117 |
|   |   |   |   |   |   | R=0.9 | Vm119 |
|   |   |   |   | 2 | Fpr121 | R=0.1 | Vm121 |
|   |   |   |   |   |   | R=0.3 | Vm123 |
|   |   |   |   |   |   | R=0.5 | Vm125 |
|   |   |   |   |   |   | R=0.7 | Vm127 |
|   |   |   |   |   |   | R=0.9 | Vm129 |
|   |   |   |   | 3 | Fpr131 | R=0.1 | Vm131 |
|   |   |   |   |   |   | R=0.3 | Vm133 |
|   |   |   |   |   |   | R=0.5 | Vm135 |
|   |   |   |   |   |   | R=0.7 | Vm137 |
|   |   |   |   |   |   | R=0.9 | Vm139 |
|   |   |   |   | ... | ... | ... | ... |
| ... | ... | ... | ... | ... | ... | ... | ... |

FIG.49

PARAMETER TABLE 510D

| ENERGY DIAL POSITION 511 | ENERGY INDICATION VALUE 512 | REPETITION FREQUENCY DIAL POSITION 515 | REPETITION FREQUENCY 516B | RISING FREQUENCY DIAL POSITION 517 | RISING FREQUENCY 518C | VOLTAGE AMPLITUDE 514 |
|---|---|---|---|---|---|---|
| 1 | E001 | 1 | Fp11 | 1 | Fpr111 | Vm111 |
|  |  |  |  |  |  | Vm113 |
|  |  |  |  |  |  | Vm115 |
|  |  |  |  |  |  | Vm117 |
|  |  |  |  |  |  | Vm119 |
|  |  |  |  | 2 | Fpr121 | Vm121 |
|  |  |  |  |  |  | Vm123 |
|  |  |  |  |  |  | Vm125 |
|  |  |  |  |  |  | Vm127 |
|  |  |  |  |  |  | Vm129 |
|  |  |  |  | 3 | Fpr131 | Vm131 |
|  |  |  |  |  |  | Vm133 |
|  |  |  |  |  |  | Vm135 |
|  |  |  |  |  |  | Vm137 |
|  |  |  |  |  |  | Vm139 |
| ... | ... | ... | ... | ... | ... | ... |

CHANGE RATIO TABLE 550

| REPETITION FREQUENCY 551 | RISING FREQUENCY 552 | VOLTAGE AMPLITUDE 553 | CUTTING TYPE DIAL POSITION 554 | MAIN JET ENERGY 556 | ENERGY CHANGE RATIO 557 |
|---|---|---|---|---|---|
| Fp101 | Fpr1011 | Vm1011 | R=0.1 | EJ11 | dE11 (=EJ11/EJ15) |
| | | | R=0.3 | EJ13 | dE13 (=EJ13/EJ15) |
| | | | R=0.5 | EJ15 | dE15 (=EJ15/EJ15) |
| | | | R=0.7 | EJ17 | dE17 (=EJ17/EJ15) |
| | | | R=0.9 | EJ19 | dE19 (=EJ19/EJ15) |
| | Fpr1012 | Vm1012 | R=0.1 | EJ21 | dE21 (=EJ21/EJ25) |
| | | | R=0.3 | EJ23 | dE23 (=EJ23/EJ25) |
| | | | R=0.5 | EJ25 | dE25 (=EJ25/EJ25) |
| | | | R=0.7 | EJ27 | dE27 (=EJ27/EJ25) |
| | | | R=0.9 | EJ29 | dE29 (=EJ29/EJ25) |
| | Fpr1013 | Vm1013 | R=0.1 | EJ31 | dE31 (=EJ31/EJ35) |
| | | | R=0.3 | EJ33 | dE33 (=EJ33/EJ35) |
| | | | R=0.5 | EJ35 | dE35 (=EJ35/EJ35) |
| | | | R=0.7 | EJ37 | dE37 (=EJ37/EJ35) |
| | | | R=0.9 | EJ39 | dE39 (=EJ39/EJ35) |
| ... | ... | ... | ... | ... | ... |

510E PARAMETER TABLE

| MOMENTUM DIAL POSITION 520 | MOMENTUM INDICATION VALUE 521 | CUTTING TYPE DIAL POSITION (R VALUE: INFLECTION POINT) INDICATION VALUE 513 | VOLTAGE AMPLITUDE 514 | REPETITION FREQUENCY 516 | RISING FREQUENCY 518 |
|---|---|---|---|---|---|
| 1 | P1 | R=0.1 | Vm11 | Fp11 | Fpr11 |
|   |    | R=0.3 | Vm13 | Fp13 | Fpr13 |
|   |    | R=0.5 | Vm15 | Fp15 | Fpr15 |
|   |    | R=0.7 | Vm17 | Fp17 | Fpr17 |
|   |    | R=0.9 | Vm19 | Fp19 | Fpr19 |
| 2 | P2 | R=0.1 | Vm21 | Fp21 | Fpr21 |
|   |    | R=0.3 | Vm23 | Fp23 | Fpr23 |
|   |    | R=0.5 | Vm25 | Fp25 | Fpr25 |
|   |    | R=0.7 | Vm27 | Fp27 | Fpr27 |
|   |    | R=0.9 | Vm29 | Fp29 | Fpr29 |
| 3 | P3 | R=0.1 | Vm31 | Fp31 | Fpr31 |
|   |    | R=0.3 | Vm33 | Fp33 | Fpr33 |
|   |    | R=0.5 | Vm35 | Fp35 | Fpr35 |
|   |    | R=0.7 | Vm37 | Fp37 | Fpr37 |
|   |    | R=0.9 | Vm39 | Fp39 | Fpr39 |
| … | … | … | … | … | … |

FIG.59

PARAMETER TABLE 510F

| MOMENTUM DIAL POSITION 520 | MOMENTUM INDICATION VALUE 521 | REPETITION FREQUENCY DIAL POSITION 515 | REPETITION FREQUENCY 516B | CUTTING TYPE DIAL POSITION 513 | VOLTAGE AMPLITUDE 514 | RISING FREQUENCY 518 |
|---|---|---|---|---|---|---|
| 1 | P1 | 1 | Fp11 | R=0.1 | Vm111 | Fpr111 |
| | | | | R=0.3 | Vm113 | Fpr113 |
| | | | | R=0.5 | Vm115 | Fpr115 |
| | | | | R=0.7 | Vm117 | Fpr117 |
| | | | | R=0.9 | Vm119 | Fpr119 |
| | | 2 | Fp12 | R=0.1 | Vm121 | Fpr121 |
| | | | | R=0.3 | Vm123 | Fpr123 |
| | | | | R=0.5 | Vm125 | Fpr125 |
| | | | | R=0.7 | Vm127 | Fpr127 |
| | | | | R=0.9 | Vm129 | Fpr129 |
| | | 3 | Fp13 | R=0.1 | Vm131 | Fpr131 |
| | | | | R=0.3 | Vm133 | Fpr133 |
| | | | | R=0.5 | Vm135 | Fpr135 |
| | | | | R=0.7 | Vm137 | Fpr137 |
| | | | | R=0.9 | Vm139 | Fpr139 |
| | | ... | ... | ... | ... | ... |
| ... | ... | | | ... | ... | ... |

FIG.63

PARAMETER TABLE 510G

| 520 MOMENTUM DIAL POSITION | 521 MOMENTUM INDICATION VALUE | 515 REPETITION FREQUENCY DIAL POSITION | 516B REPETITION FREQUENCY | 517 RISING FREQUENCY DIAL POSITION | 518C RISING FREQUENCY | 513 CUTTING TYPE DIAL POSITION | 514 VOLTAGE AMPLITUDE |
|---|---|---|---|---|---|---|---|
| 1 | P1 | 1 | Fp11 | 1 | Fpr111 | R=0.1 | Vm111 |
| | | | | | | R=0.3 | Vm113 |
| | | | | | | R=0.5 | Vm115 |
| | | | | | | R=0.7 | Vm117 |
| | | | | | | R=0.9 | Vm119 |
| | | | | 2 | Fpr121 | R=0.1 | Vm121 |
| | | | | | | R=0.3 | Vm123 |
| | | | | | | R=0.5 | Vm125 |
| | | | | | | R=0.7 | Vm127 |
| | | | | | | R=0.9 | Vm129 |
| | | | | 3 | Fpr131 | R=0.1 | Vm131 |
| | | | | | | R=0.3 | Vm133 |
| | | | | | | R=0.5 | Vm135 |
| | | | | | | R=0.7 | Vm137 |
| | | | | | | R=0.9 | Vm139 |
| ... | ... | ... | ... | ... | ... | ... | ... |

FIG.67

PARAMETER TABLE 510H

| MOMENTUM DIAL POSITION 520 | MOMENTUM INDICATION VALUE 521 | REPETITION FREQUENCY DIAL POSITION 515 | REPETITION FREQUENCY 516B | RISING FREQUENCY DIAL POSITION 517 | RISING FREQUENCY 518C | VOLTAGE AMPLITUDE 514 |
|---|---|---|---|---|---|---|
| 1 | P1 | 1 | Fp11 | 1 | Fpr111 | Vm111 |
| | | | | | | Vm113 |
| | | | | | | Vm115 |
| | | | | | | Vm117 |
| | | | | | | Vm119 |
| | | | | 2 | Fpr121 | Vm121 |
| | | | | | | Vm123 |
| | | | | | | Vm125 |
| | | | | | | Vm127 |
| | | | | | | Vm129 |
| | | | | 3 | Fpr131 | Vm131 |
| | | | | | | Vm133 |
| | | | | | | Vm135 |
| | | | | | | Vm137 |
| | | | | | | Vm139 |
| ... | ... | | | ... | ... | ... |
| | | | | ... | ... | ... |

FIG.68

CHANGE RATIO TABLE 550H

| 551 REPETITION FREQUENCY | 552 RISING FREQUENCY | 553 VOLTAGE AMPLITUDE | 554 CUTTING TYPE DIAL POSITION | 560 MAIN JET MOMENTUM | 561 MOMENTUM CHANGE RATIO |
|---|---|---|---|---|---|
| Fp101 | Fpr1011 | Vm1011 | R=0.1 | PJ11 | dP11 (=PJ11/PJ15) |
| | | | R=0.3 | PJ13 | dP13 (=PJ13/PJ15) |
| | | | R=0.5 | PJ15 | dP15 (=PJ15/PJ15) |
| | | | R=0.7 | PJ17 | dP17 (=PJ17/PJ15) |
| | | | R=0.9 | PJ19 | dP19 (=PJ19/PJ15) |
| | Fpr1012 | Vm1012 | R=0.1 | PJ21 | dP21 (=PJ21/PJ25) |
| | | | R=0.3 | PJ23 | dP23 (=PJ23/PJ25) |
| | | | R=0.5 | PJ25 | dP25 (=PJ25/PJ25) |
| | | | R=0.7 | PJ27 | dP27 (=PJ27/PJ25) |
| | | | R=0.9 | PJ29 | dP29 (=PJ29/PJ25) |
| | Fpr1013 | Vm1013 | R=0.1 | PJ31 | dP31 (=PJ31/PJ35) |
| | | | R=0.3 | PJ33 | dP33 (=PJ33/PJ35) |
| | | | R=0.5 | PJ35 | dP35 (=PJ35/PJ35) |
| | | | R=0.7 | PJ37 | dP37 (=PJ37/PJ35) |
| | | | R=0.9 | PJ39 | dP39 (=PJ39/PJ35) |
| | ... | ... | ... | ... | ... |
| ... | | | | ... | ... |

LIQUID EJECTION CONTROL APPARATUS, LIQUID EJECTION SYSTEM, AND CONTROL METHOD

BACKGROUND

1. Technical Field

The present invention relates to a control apparatus and the like controlling ejection of a pulsed liquid jet by controlling a drive voltage waveform applied to a piezoelectric element.

2. Related Art

There is a technique of cutting a cutting target object by ejecting a liquid in a pulse form. The liquid ejected in a pulse form is a liquid jet flow which is ejected from a nozzle in a pulsating manner, and is referred to as a "pulsed liquid jet" as appropriate in the present specification.

A pulsed liquid jet may be variously applied, and, for example, JP-A-2005-152127 has proposed a technique in which the pulsed liquid jet is used for surgery in a medical field. In this case, a cutting target object is living tissue, and a liquid is physiological saline.

As one of the mechanisms generating a pulsed liquid jet, there is a mechanism using a piezoelectric element. The mechanism applies a pulsed drive voltage to a piezoelectric element so that the piezoelectric element generates instantaneous pressure in a working fluid (fluid), and thus ejects the liquid in a pulse form. Thus, the strength of the pulsed liquid jet is changed by controlling a drive voltage applied to the piezoelectric element. JP-A-2009-39384 or JP-A-2011-36533 discloses a technique of changing a characteristic value of a drive voltage applied to a piezoelectric element, for example, the amplitude or a frequency of a drive voltage waveform.

A cut depth or a cut volume related to one pulsed liquid jet can be changed by changing a drive voltage. However, in a case of taking into consideration convenience or usability when cutting is performed by using a pulsed liquid jet, simply changing a cut depth or a cut volume cannot be said to cope with all cutting applications and thus to be versatile. For example, there is a need for changing an aspect during cutting (hereinafter, referred to as a "cutting aspect" as appropriate), such as a need for "narrow and deep" cutting, or a need for "wide and shallow" cutting.

SUMMARY

An advantage of some aspects of the invention is to provide an ejection control technique for a pulsed liquid jet, capable of changing a cutting aspect.

A first aspect of the invention is directed to a liquid ejection control apparatus which controls a drive voltage waveform applied to a piezoelectric element so as to control ejection of a pulsed liquid jet, the apparatus including a first operation unit that receives input of an index value for setting a position of an inflection point in a rising portion of the drive voltage waveform; and a control unit that sets the position of the inflection point in the rising portion of the drive voltage waveform according to the index value so as to control changing of the drive voltage waveform.

As will be described later in detail, it has been found that a rising portion of a drive voltage waveform has great influence on an action of a pulsed liquid jet, and a cutting aspect is changed by changing a position of an inflection point in the rising portion. According to the first aspect of the invention, since an inflection point position in the rising portion of the drive voltage waveform can be changed according to an index value input by a user, the user can change a cutting aspect to a desired aspect.

As a more specific configuration, as a second aspect of the invention, the liquid ejection control apparatus according to the first aspect of the invention may be configured such that the control unit moves the inflection point along a line segment connecting a rising start point to a maximum voltage in the rising portion so as to set the position of the inflection point corresponding to the index value.

A third aspect of the invention is directed to the liquid ejection control apparatus according to the first or second aspect of the invention, which further includes a second operation unit that receives input of an indication value of momentum or kinetic energy of the pulsed liquid jet, and in which the control unit sets the position of the inflection point according to the index value, and controls changing of the drive voltage waveform so that the indication value is obtained.

According to the third aspect of the invention, the position of the inflection point in the rising portion of the drive voltage waveform is changed according to the input index value, but the drive voltage waveform is controlled so that momentum or kinetic energy related to a pulsed liquid jet has the input indication value. As will be described later, a cut volume has a high correlation with the momentum or the kinetic energy related to a pulsed liquid jet. Thus, a user directly indicates momentum or kinetic energy related to a pulsed liquid jet, and thus it is possible to realize a cut volume suitable for the user's intention or operation sense and also to further improve convenience along with changing of a cutting aspect.

A fourth aspect of the invention is directed to the liquid ejection control apparatus according to the third aspect of the invention, in which the control unit controls the amplitude of the drive voltage waveform so that the indication value is obtained.

According to the fourth aspect of the invention, it is possible to control the amplitude of the drive voltage waveform applied to the piezoelectric element so that momentum or kinetic energy related to a pulsed liquid jet has the input indication value.

A fifth aspect of the invention is directed to the liquid ejection control apparatus according to the third or fourth aspect of the invention, in which the control unit controls any one of time, a rising frequency, and a repetition frequency related to rising of the drive voltage waveform so that the indication value is obtained.

According to the fifth aspect of the invention, it is possible to control any one of time, a rising frequency, and a repetition frequency related to rising of the drive voltage waveform applied to the piezoelectric element so that momentum or kinetic energy related to a pulsed liquid jet has the input indication value.

A sixth aspect of the invention is directed to the liquid ejection control apparatus according to any one of the first to fifth aspects of the invention, in which ejection control of the pulsed liquid jet is performed so that momentum of the pulsed liquid jet is equal to or more than 2 nanonewton seconds (nNs) and is equal to or less than 2 millinewton seconds (mNs), or kinetic energy of the pulsed liquid jet is equal to or more than 2 nanojoules (nJ) and is equal to or less than 200 millijoules (mJ).

According to the sixth aspect of the invention, it is possible to control ejection of a pulsed liquid jet within a range in which the momentum is equal to or more than 2 nNs and is equal to or less than 2 mNs, and the kinetic energy is equal to or more than 2 nJ and is equal to or less than 200 mJ. Therefore, for example, the liquid ejection control apparatus is suitable to cut soft materials, for example, living tissue, food, a gel material, and a resin material such as rubber or plastic.

A seventh aspect of the invention is directed to the liquid ejection control apparatus according to any one of the first to sixth aspects of the invention, in which ejection control of the pulsed liquid jet is performed so that living tissue is cut.

According to the seventh aspect of the invention, it is possible to control the strength of a pulsed liquid jet suitable for surgery, for example.

An eighth aspect of the invention is directed to a liquid ejection system including the liquid ejection control apparatus according to any one of the first to seventh aspects of the invention; a liquid ejection device that ejects the pulsed liquid jet; and a liquid feeding pump that feeds a liquid to the liquid ejection device.

According to the eighth aspect of the invention, it is possible to implement the liquid ejection system achieving the operations and effects of the first to seventh aspects.

A ninth aspect of the invention is directed to a control method of controlling a drive voltage waveform applied to a piezoelectric element so as to control ejection of a pulsed liquid jet, the method including receiving input of an index value for setting a position of an inflection point in a rising portion of the drive voltage waveform; and setting the position of the inflection point in the rising portion of the drive voltage waveform according to the index value so as to control changing of the drive voltage waveform.

According to the ninth aspect of the invention, it is possible to achieve the same operation and effect as in the first aspect.

BRIEF DESCRIPTION OF THE DRAWINGS

The invention will be described with reference to the accompanying drawings, wherein like numbers reference like elements.

FIG. 37 is a diagram illustrating a data configuration example of a parameter table in the first embodiment.

FIG. 41 is a diagram illustrating a data configuration example of a parameter table in the second embodiment.

FIG. 45 is a diagram illustrating a data configuration example of a parameter table in the third embodiment.

FIG. 49 is a diagram illustrating a data configuration example of a parameter table in the fourth embodiment.

FIG. 50 is a diagram illustrating a data configuration example of a change ratio table in the fourth embodiment.

FIG. 55 is a diagram illustrating a data configuration example of a parameter table in the fifth embodiment.

FIG. 59 is a diagram illustrating a data configuration example of a parameter table in the sixth embodiment.

FIG. 63 is a diagram illustrating a data configuration example of a parameter table in the seventh embodiment.

FIG. 67 is a diagram illustrating a data configuration example of a parameter table in the eighth embodiment.

FIG. 68 is a diagram illustrating a data configuration example of a change ratio table in the eighth embodiment.

DESCRIPTION OF EXEMPLARY EMBODIMENTS

Figure 1:
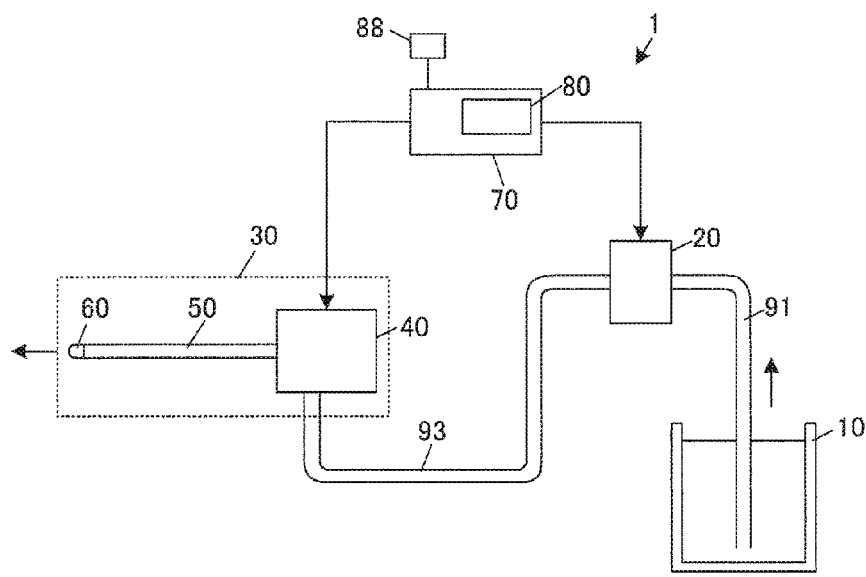
FIG. 1 is a diagram illustrating the entire configuration example of a liquid ejection system.

Hereinafter, a description will be made of embodiments of a liquid ejection control apparatus, a liquid ejection device, and a liquid ejection control method according to the invention. The invention is not limited to the embodiments described below, and embodiments to which the invention is applicable are not limited to the embodiments described below. The same portions are given the same reference numerals throughout the drawings.

First Embodiment

FIG. 1 is a diagram illustrating the entire configuration example of a liquid ejection system 1 in the present embodiment.

The liquid ejection system 1 is used for applications such as surgery with a soft material, for example, living tissue as a cutting target object, food processing with food as a cutting target object, processing of a gel material, and cutting processing of a resin material such as rubber or plastic, and ejects a pulsed liquid jet whose momentum is equal to or more than 2 nanonewton seconds (nNs) and is equal to or less than 2 millinewton seconds (mNs), or whose kinetic energy is equal to or more than 2 nanojoules (nJ) and is equal to or less than 200 millijoules (mJ) so as to cut a cutting target object. Hereinafter, a case will be exemplified in which the liquid ejection system 1 is used for a surgery application and performs incision, excision, or crushing (these are collectively referred to as "cutting") of the affected part (living tissue). Momentum flux and momentum in the present embodiment indicate a scalar quantity in which only an ejection direction component of a pulsed liquid jet, that is, the magnitude thereof is taken into consideration.

The liquid ejection system 1 includes a container 10 accommodating a liquid, a liquid feeding pump 20, a liquid ejection device 30 which ejects the liquid toward a cutting target object (living tissue in the present embodiment) in a pulse form, and a liquid ejection control apparatus 70.

In the liquid ejection system 1, the liquid ejection control apparatus 70 is provided with an operation panel 80 which is operated by a user during surgery. The operation panel 80 is used to input various operations such as an operation of changing kinetic energy. The liquid ejection control apparatus 70 is provided with an ejection pedal 88 for switching between ejection starting and ejection stoppage of a pulsed liquid jet by the user treading thereon.

The container 10 accommodates a liquid such as water, physiological saline, or a chemical liquid. The liquid feeding pump 20 supplies the liquid accommodated in the container 10 to a pulse flow generator 40 of the liquid ejection device 30 at predetermined pressure or a predetermined flow rate via connection tubes 91 and 93.

The liquid ejection device 30 is a portion called "handpiece" held and operated by the user during surgery. The liquid ejection device 30 includes the pulse flow generator 40 which gives pulsation to the liquid supplied from the liquid feeding pump 20 so as to generate a pulse flow, and an pipe-shaped ejection tube 50. The liquid ejection device 30 ejects the pulse flow generated by the pulse flow generator 40 from a front end nozzle 60 through the ejection tube 50 as a pulsed liquid jet.

Here, the pulse flow indicates a pulsative flow of the liquid which considerably and rapidly changes temporally in a flow velocity or pressure thereof. Similarly, ejecting a liquid in a pulse form indicates pulsative ejection of the liquid in which a flow velocity of the liquid passing through the nozzle considerably changes temporally. In the present embodiment, a case of ejecting a pulsed liquid jet generated by applying periodic pulsation to a steady flow is exemplified, but the invention is also applicable to intermittent and fitful ejection of a pulsed liquid jet in which ejection and non-ejection of a liquid are repeatedly performed.

Figure 2:
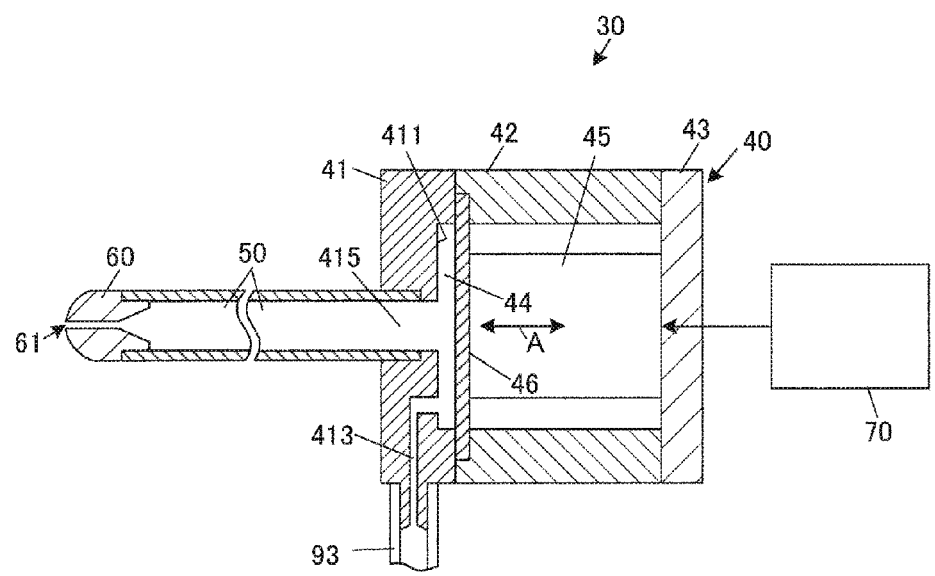
FIG. 2 is a diagram illustrating an internal structure of a liquid ejection device.

FIG. 2 is a diagram illustrating a cut surface obtained by cutting the liquid ejection device 30 along a liquid ejection direction. Vertical and horizontal scales of members or portions are different from actual ones for convenience of illustration.

The pulse flow generator 40 is configured of a piezoelectric element 45 and a diaphragm 46 which change a volume of a pressure chamber 44 and are disposed in a tubular internal space formed by a first case 41, a second case 42, and a third case 43. The respective cases 41, 42 and 43 are joined together and are thus integrally formed at surfaces facing each other.

The diaphragm 46 is a disk-shaped metal thin plate, and an outer circumferential portion thereof is interposed and fixed between the first case 41 and the second case 42. The piezoelectric element 45 is, for example, a laminated piezoelectric element, and has one end fixed to the diaphragm 46 between the diaphragm 46 and the third case 43, and the other end fixed to the third case.

The pressure chamber 44 is a space surrounded by the diaphragm 46, and a depression 411 formed on a surface of the first case 41 facing the diaphragm 46. The first case 41 is provided with an inlet channel 413 and an outlet channel 415 which communicate with the pressure chamber 44. An inner diameter of the outlet channel 415 is larger than an inner diameter of the inlet channel 413. The inlet channel 413 is connected to the connection tube 93 and introduces a liquid supplied from the liquid feeding pump 20 into the pressure chamber 44. One end of the ejection tube 50 is connected to the outlet channel 415, and thus the liquid flowing in the pressure chamber 44 is introduced into the ejection tube 50. The nozzle 60 having a liquid ejection opening 61 which has an inner diameter smaller than an inner diameter of the ejection tube 50 is inserted into the other end (front end) of the ejection tube 50.

The liquid accommodated in the container 10 is supplied to the pulse flow generator 40 via the connection tube 93 at predetermined pressure or a predetermined flow rate by the liquid feeding pump 20 whose driving is controlled by the liquid ejection control apparatus 70. If a drive signal is output from the liquid ejection control apparatus 70 to the piezoelectric element 45, and thus a drive voltage is applied thereto, the piezoelectric element 45 is expanded or contracted (an arrow A in FIG. 2).

The drive voltage is repeatedly applied at a predetermined repetition frequency (for example, several tens of Hz to several hundreds of Hz), and thus expansion and contraction of the piezoelectric element 45 are repeatedly performed for each cycle. Consequently, pulsation is applied to the steady flow liquid flowing in the pressure chamber 44, and thus a pulsed liquid jet is repeatedly ejected from the liquid ejection opening 61.

Specifically, if a positive voltage is applied, the piezoelectric element 45 is expanded, and thus the diaphragm 46 is pushed by the piezoelectric element 45 so as to be bent toward the pressure chamber 44 side. If the diaphragm 46 is bent toward the pressure chamber 44 side, the volume of the pressure chamber 44 is reduced, and thus the liquid in the pressure chamber 44 is pushed out of the pressure chamber 44. Here, the inner diameter of the outlet channel 415 is larger than the inner diameter of the inlet channel 413, fluid inertance and fluid resistance of the outlet channel 415 are less than fluid resistance of the inlet channel 413. Therefore, most of the liquid pushed out of the pressure chamber 44 due to rapid expansion of the piezoelectric element 45 is introduced into the ejection tube 50 through the outlet channel 415, and is ejected at a high speed as pulsed liquid droplets, that is, a "pulsed liquid jet" through the liquid ejection opening 61 having the diameter smaller than the diameter of the outlet channel.

In the process in which the drive voltage is increased to voltage amplitude and is then slowly decreased, the piezoelectric element 45 is contracted for a longer time than a rising time, and thus the diaphragm 46 is pulled to the piezoelectric element 45 so as to be bent toward the third case 43 side. On the other hand, since the liquid feeding pump 20 supplies the liquid to the pulse flow generator 40 at predetermined pressure or a predetermined flow rate, if the diaphragm 46 is bent toward the third case 43 side and thus the volume of the pressure chamber 44 is increased, the liquid is introduced from the inlet channel 413 into the pressure chamber 44 which is then replenished therewith, and fills the ejection tube 50 through the outlet channel 415. In the process in which the piezoelectric element 45 is rapidly expanded next, the next pulsed liquid jet is ejected from the liquid ejection opening 61.

Even in a case where an expansion operation of the piezoelectric element 45 is not performed, in a case where the liquid feeding pump 20 is operated, the liquid enters the pressure chamber 44 from the inlet channel 413, and flows out of the liquid ejection opening 61 via the ejection tube 50 through the outlet channel 415. This outflow is a liquid flow at a constant and low speed, and may thus be regarded as a steady flow.

Figure 3:
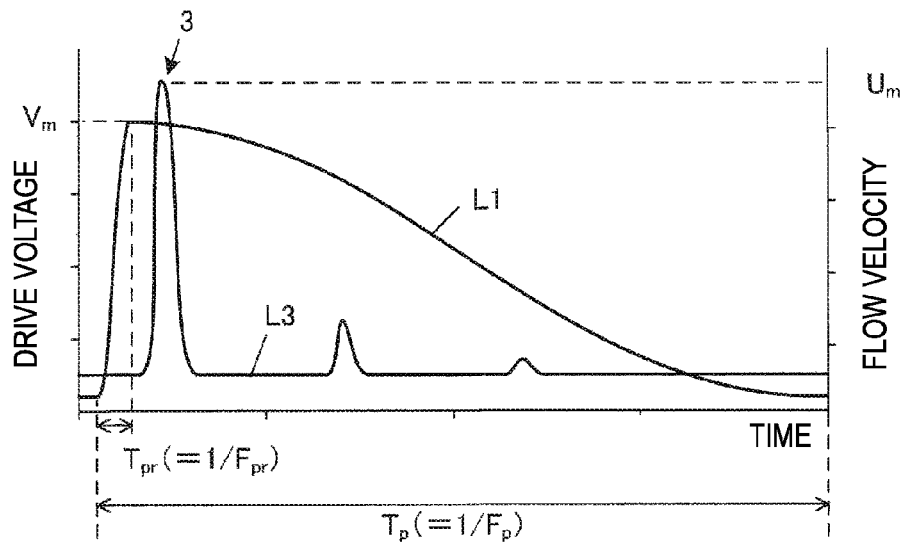
FIG. 3 is a diagram illustrating a drive voltage waveform for a piezoelectric element corresponding to one cycle and a liquid flow velocity waveform in a liquid ejection opening.

FIG. 3 is a diagram illustrating examples of a drive voltage waveform L1 of a drive signal corresponding to one cycle applied to the piezoelectric element 45, and a flow velocity waveform L3 of a liquid in the liquid ejection opening 61.

A repetition cycle $T_p$ of the drive voltage waveform L1 is time corresponding to one cycle of the drive voltage waveform L1, and an inverse number thereof is a repetition frequency $F_p$. The repetition cycle $T_p$ is about 1 millisecond (ms) to 100 ms.

Rising time $T_{pr}$ of the drive voltage waveform L1 is time required for the drive voltage waveform L1 to rise to the maximum voltage, and an inverse number thereof is a rising frequency $F_{pr}$. The rising time $T_{pr}$ is about 10 microseconds (μs) to 1000 μs.

The repetition cycle $T_p$ is set to be longer than the rising time $T_{pr}$, and the repetition frequency $F_p$ is set to be lower than the rising frequency $F_{pr}$. Both of the rising frequency $F_{pr}$ and the rising time $T_{pr}$ are rising indexes related to rising of the drive voltage waveform L1.

Figure 4:
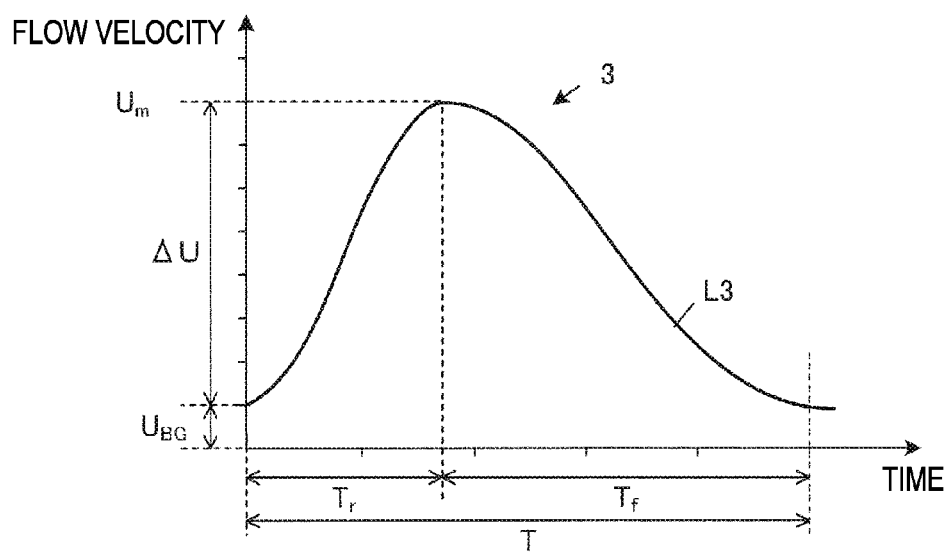
FIG. 4 is a diagram obtained by extracting a flow velocity waveform of a main jet from FIG. 3.

After the drive voltage waveform L1 reaches the voltage amplitude $V_m$, a pulsed liquid jet may include a plurality of liquid masses. Above all, a flow velocity waveform (a jet in a head wave) with the highest peak generated right after rising of the drive voltage is focused. An enlarged view of the waveform is illustrated in FIG. 4. Other low peaks are caused by jets which are incidentally ejected since a pressure changing wave occurring in the pressure chamber 44 during expansion of the piezoelectric element 45 reflects and reciprocates in the ejection tube 50, but a destruction state of a cutting target object, that is, a cut depth or a cut volume of the cutting target object is determined by a jet (main jet) in a head wave with the highest flow velocity.

FIG. 4 is a diagram obtained by extracting a flow velocity waveform of a main jet.

Duration T of a main jet 3 is a period of time after a flow velocity waveform L3 returns to an initial flow velocity $U_{BG}$ after increasing more than the flow velocity $U_{BG}$ of a steady flow and reaching a peak. The duration T is a sum of a flow velocity rising time $T_r$ required for a flow velocity to reach the peak and a flow velocity falling time $T_f$ required for the flow velocity to return to the initial state from the peak.

Principle

Next, a description will be made of a principle for adjusting a cutting aspect using a pulsed liquid jet from a "narrow and deep" aspect to a "wide and shallow" aspect without changing a cut volume if at all possible.

First, a description will be made of a principle for realizing the premise, "without changing a cut volume if at all possible".

A pulsed liquid jet is characterized by the flow velocity waveform L3 in the liquid ejection opening 61 of a jet corresponding to a single pulse, but a destruction state of a cutting target object, that is, a cut depth, a cut volume, or a cut area is determined by the main jet 3 with the highest flow velocity.

Therefore, focusing on the flow velocity waveform L3 (refer to FIG. 4) of the main jet 3, correlations among several parameters, a cut depth, and a cut volume determined by the flow velocity waveform L3 of the main jet 3 was examined.

Specifically, on the basis of the flow velocity waveform L3 of the main jet in the liquid ejection opening 61, mass flux kg/s, momentum flux N, and energy flux W, passing through the liquid ejection opening 61, were examined. The mass flux is mass [kg/s] per unit time of a liquid passing through the liquid ejection opening 61. The momentum flux is momentum [N] per unit time of a liquid passing through the liquid ejection opening 61. The energy flux is energy [W] per unit time of a liquid passing through the liquid ejection opening 61. The energy indicates kinetic energy, and will be hereinafter abbreviated to "energy".

In the liquid ejection opening 61, a liquid is released to a free space, and thus pressure may be regarded to be "0". A velocity of the liquid in a direction orthogonal to a jet ejection direction (a diameter direction of the liquid ejection opening 61) may also be regarded to be "0". Assuming that there is no velocity distribution of a liquid in a diameter direction of the liquid ejection opening 61, mass flux Jm [kg/s], momentum flux Jp [N], and energy flux Je [W] of the liquid passing through the liquid ejection opening 61 may be respectively obtained according to the following Equations (1), (2) and (3). S [m²] indicates a nozzle sectional area, and ρ [kg/m³] indicates a working fluid density.

$$Jm = S \cdot \rho \cdot v \quad (1)$$

$$Jp = S \cdot \rho \cdot v^2 \quad (2)$$

$$Je = 1/2 \cdot \rho \cdot S \cdot v^3 \quad (3)$$

Figure 5:
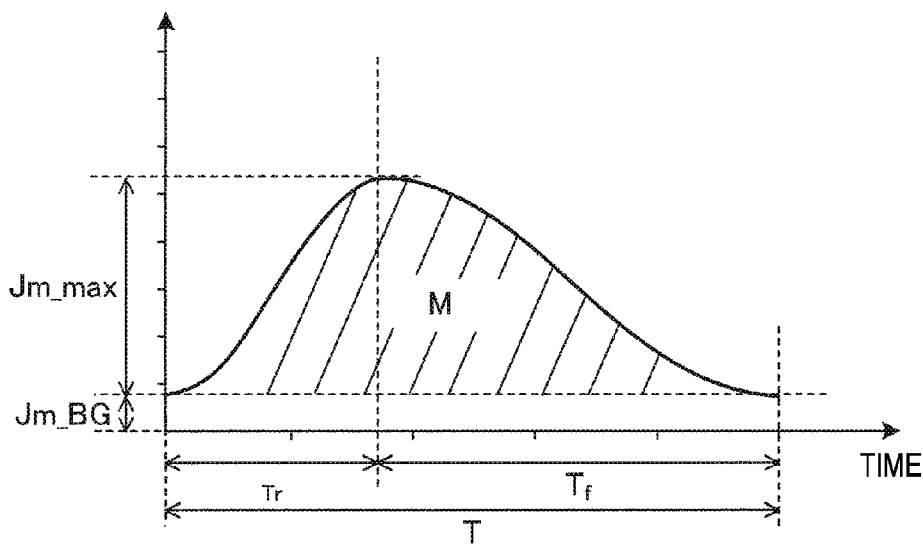
FIG. 5 is a diagram illustrating mass flux obtained on the basis of the flow velocity waveform of the main jet.
Figure 6:
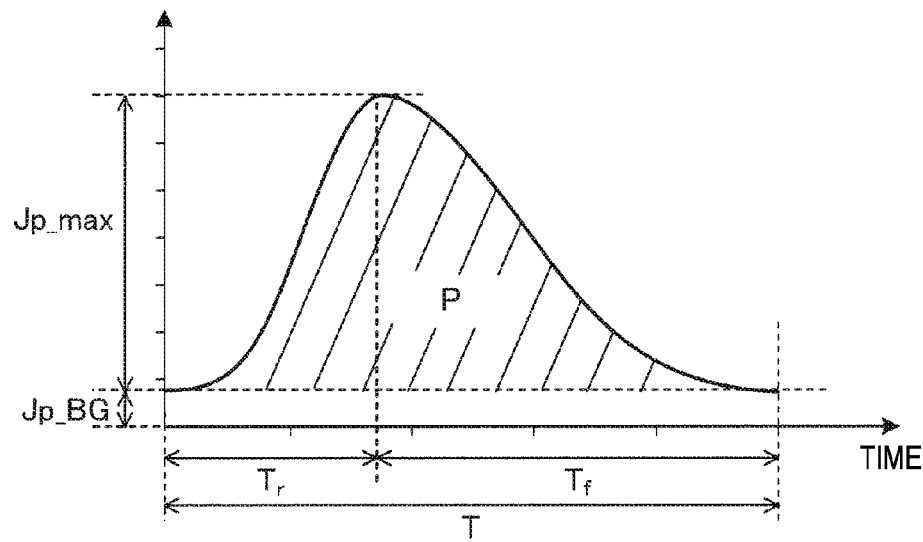
FIG. 6 is a diagram illustrating momentum flux obtained on the basis of the flow velocity waveform of the main jet.
Figure 7:
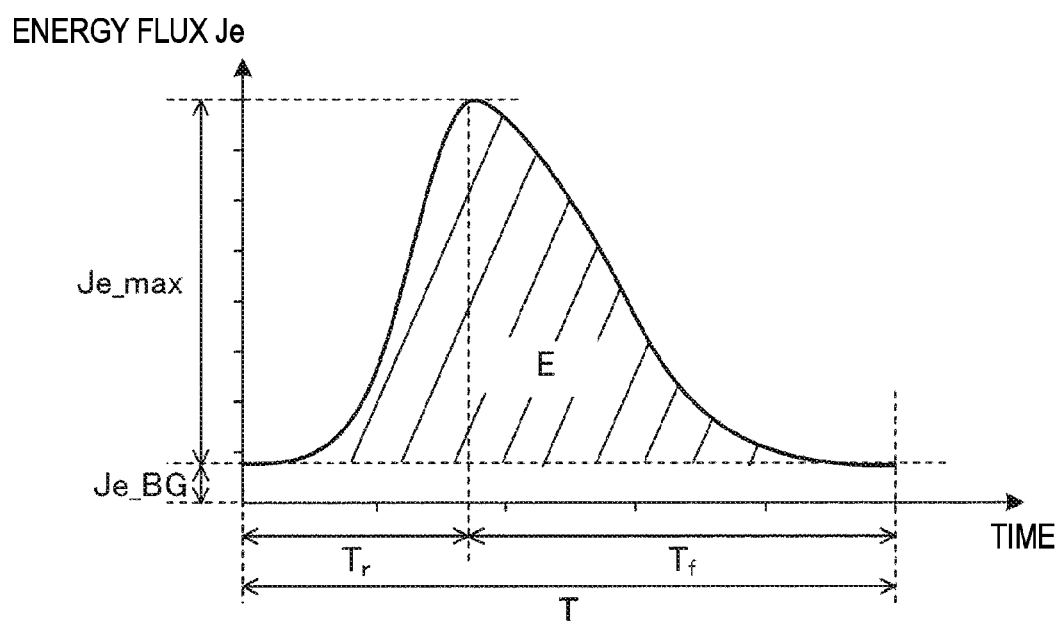
FIG. 7 is a diagram illustrating energy flux obtained on the basis of the flow velocity waveform of the main jet.

FIGS. 5 to 7 are graphs respectively illustrating mass flux Jm, momentum flux Jp, and energy flux Je obtained on the basis of the flow velocity waveform L3 of the main jet 3. If each of the mass flux Jm, the momentum flux Jp, and the energy flux Je is integrated over time (duration T) from rising to falling of the flow velocity waveform of the main jet, mass, momentum, and energy of a liquid ejected from the liquid ejection opening 61 as the main jet 3 can be obtained.

The mass flux Jm, the momentum flux Jp, the energy flux Je, the mass, the momentum, and the energy calculated in the above-described way may determine a cut depth and a cut volume related to a single main jet 3. However, each of the above physical quantities includes a quantity corresponding to a steady flow, and it is noted that a value thereof is obtained by subtracting an attribution of the steady flow.

Therefore, regarding the mass flux Jm illustrated in FIG. 5, two parameters are defined, such as the maximum mass flux Jm_max [kg/s] obtained by subtracting mass flux Jm_BG [kg/s] of a steady flow from a peak value (maximum value) of the mass flux Jm, and outflow mass M [kg] (a hatched portion in FIG. 5) obtained by excluding an amount corresponding to the steady flow from mass of a liquid flowing out of the liquid ejection opening 61 as a main jet. The outflow mass M is expressed by the following Equation (4).

$$M = \int (Jm - Jm\_BG) dt \quad (4)$$

Regarding the momentum flux Jp illustrated in FIG. 6, two parameters are defined, such as the maximum momentum flux Jp_max [N] obtained by subtracting momentum flux Jp_BG [N] of a steady flow from a peak value (maximum value) of the momentum flux Jp, and momentum P [Ns] (a hatched portion in FIG. 6) obtained by excluding an amount corresponding to the steady flow from momentum of a liquid flowing out of the liquid ejection opening 61 as a main jet. The momentum P is expressed by the following Equation (5).

$$P = \int (Jp - Jp\_BG) dt \quad (5)$$

Regarding the energy flux Je illustrated in FIG. 7, two parameters are defined, such as the maximum energy flux Je_max [W] obtained by subtracting energy flux Je_BG [W] of a steady flow from a peak value (maximum value) of the energy flux Je, and energy E [J] (a hatched portion in FIG. 7) obtained by excluding an amount corresponding to the steady flow from energy of a liquid flowing out of the liquid ejection opening 61 as a main jet. The energy E is expressed by the following Equation (6).

$$E = \int (Je - Je\_BG) dt \quad (6)$$

Here, the integration section in each of the above Equations (4), (5) and (6) is time (duration T) from rising to falling of the main jet 3 in the flow velocity waveform.

By using numerical value simulation, to what extent each of the six parameters such as the maximum mass flux Jm_max, the outflow mass M, the maximum momentum flux Jp_max, the momentum P, the maximum energy flux Je_max, and the energy E is correlated with a cut depth and a cut volume was examined.

Here, a pulsed liquid jet is a fluid, and a cutting target object is a soft elastic body. Therefore, in order to perform simulation for a destruction behavior of the cutting target object using the pulsed liquid jet, an appropriate destruction threshold value is set on the soft elastic body side, and then so-called interaction analysis (fluid structure interaction (FSI) analysis) of the fluid and a structure (here, the soft elastic body) is required to be performed. Examples of computation methods in simulation may include a finite element method (FEM), a method using a particle method whose representative is a smoothed particle hydrodynamics (SPH), and a method of combining the finite element method with the particle method. An applied method is not particularly limited. Thus, although not described in detail, an optimal method was selected by taking into consideration of stability of an analysis result, computation time, and the like, and the simulation was performed.

When the simulation was performed, a fluid density=1 g/cm$^3$, a diameter of the liquid ejection opening 61=0.15 mm, and a standoff distance (a distance from the liquid ejection opening 61 to a surface of the cutting target object) =0.5 mm were set. Assuming that the cutting target object was a soft elastic body having a flat surface, a Mooney-Rivlin super-elastic body having a density of 1 g/cm$^3$ and an elastic modulus of about 9 kPa (about 3 kPa in terms of shear modulus) in terms of Young's modulus was used as a physical model thereof. Equivalent deviation strain=0.7 was used in the destruction threshold value.

Regarding flow velocity waveforms of a main jet, various flow velocity waveforms were assumed, and a total of flow velocity waveforms of 27 types were prepared by changing amplitude (the maximum value of flow velocity) of three types in a range of 12 m/s to 76 m/s and changing duration of three type in a range of 63 μs to 200 μs, with respect to each of waveforms of three types such as a sine wave, a triangular wave, and a rectangular wave. A flow velocity of a steady flow was 1 m/s.

Figure 8:
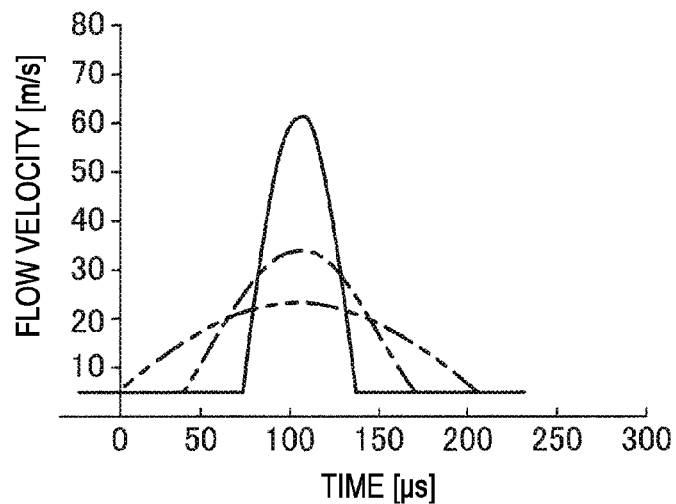
FIG. 8 is a diagram illustrating a sine wave provided as a flow velocity waveform of a main jet in simulation.
Figure 9:
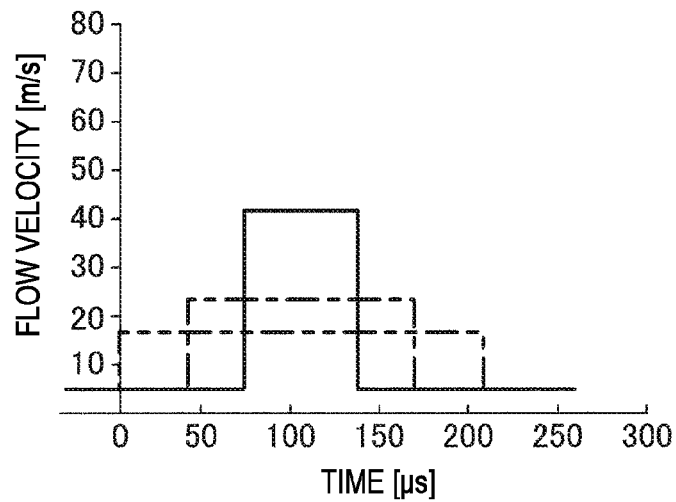
FIG. 9 is a diagram illustrating a rectangular wave provided as a flow velocity waveform of a main jet in simulation.
Figure 10:
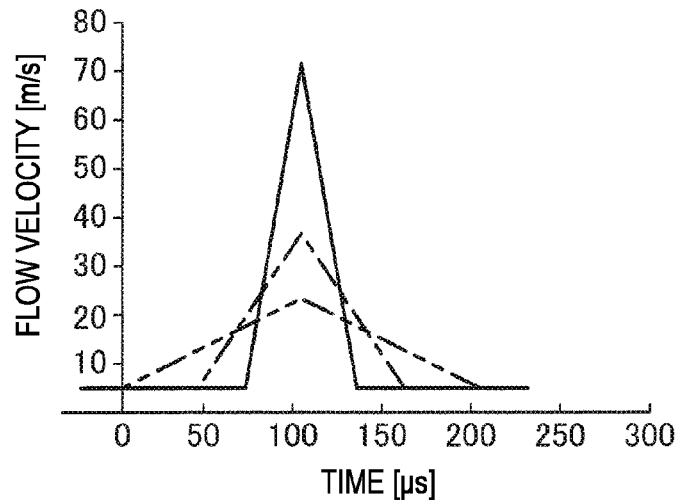
FIG. 10 is a diagram illustrating a triangular wave provided as a flow velocity waveform of a main jet in simulation.

FIGS. 8 to 10 respectively illustrate a sine wave, a rectangular wave, and a triangular wave provided as flow velocity waveforms of a main jet in the simulation, in which a solid line indicates a case where the duration is 63 μs, a dot chain line indicates a case where the duration is 125 μs, and a two-dot chain line indicates a case where the duration is 200 μs. The waveforms were provided as flow velocity waveforms of a main jet so that pulsed liquid jets were generated, the simulation for a destruction behavior of the soft elastic body when the pulsed liquid jets were ejected onto the soft elastic body was performed, and a cut depth or a cut volume was examined.

FIGS. 11 to 16 are diagrams respectively plotting simulation results of relationships of the maximum mass flux Jm_max (FIG. 11), the maximum momentum flux Jp_max (FIG. 12), the maximum energy flux Je_max (FIG. 13), the outflow mass M (FIG. 14), the momentum P (FIG. 15), and the energy E (FIG. 16), with respect to a cut depth of a cutting target object.

In the figures, a simulation result obtained when a sine wave with the duration of 63 μs is provided as a flow velocity waveform of a main jet is indicated by a plot of "*"; a simulation result obtained when a sine wave with the duration of 125 μs is provided as a flow velocity waveform of a main jet is indicated by a plot of "♦"; and a simulation result obtained when a sine wave with the duration of 200 μs is provided as a flow velocity waveform of a main jet is indicated by a plot of "–".

In addition, a simulation result obtained when a triangular wave with the duration of 63 μs is provided as a flow velocity waveform of a main jet is indicated by a plot of "+"; a simulation result obtained when a triangular wave with the duration of 125 μs is provided as a flow velocity waveform of a main jet is indicated by a plot of "X"; and a simulation result obtained when a triangular wave with the duration of 200 μs is provided as a flow velocity waveform of a main jet is indicated by a plot of a square shape displayed black.

Further, a simulation result obtained when a rectangular wave with the duration of 63 μs is provided as a flow velocity waveform of a main jet is indicated by a plot of "●"; a simulation result obtained when a rectangular wave with the duration of 125 μs is provided as a flow velocity waveform of a main jet is indicated by a plot of a triangular shape displayed black; and a simulation result obtained when a rectangular wave with the duration of 200 μs is provided as a flow velocity waveform of a main jet is indicated by a plot of "-".

Figure 11:
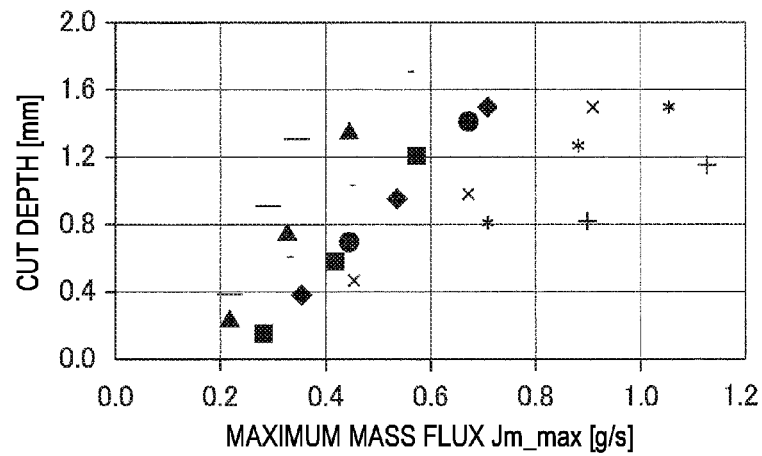
FIG. 11 is a diagram plotting a simulation result of a relationship between a cut depth of a cutting target object and the maximum mass flux.
Figure 12:
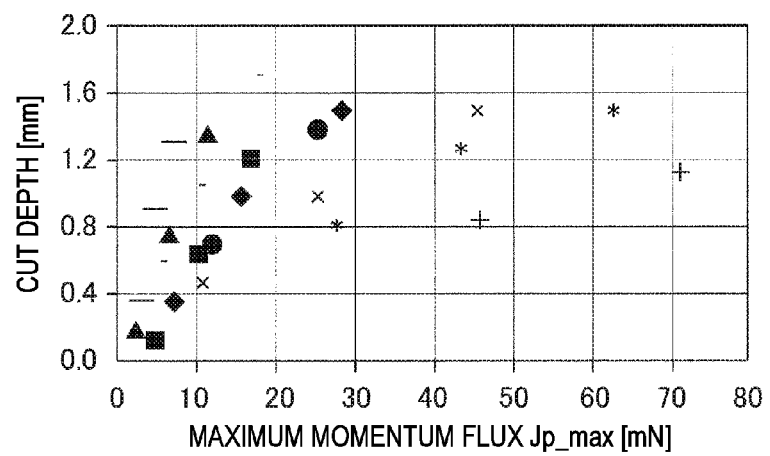
FIG. 12 is a diagram plotting a simulation result of a relationship between a cut depth of a cutting target object and the maximum momentum flux.
Figure 13:
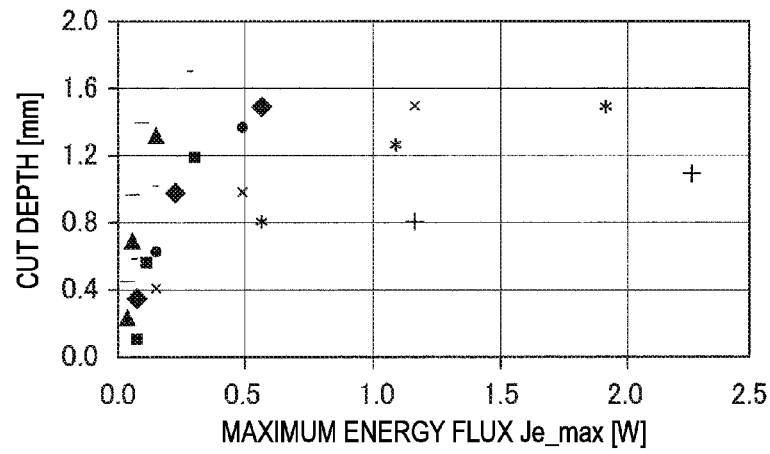
FIG. 13 is a diagram plotting a simulation result of a relationship between a cut depth of a cutting target object and the maximum energy flux.

As illustrated in FIGS. 11 to 13, the relationship between each of the three parameters such as the maximum mass flux Jm_max, the maximum momentum flux Jp_max, and the maximum energy flux Je_max, and the cut depth greatly varies depending on the shape of the waveform provided as a flow velocity waveform of a main jet, and thus it was found that a mutual correlation is low. Especially, this suggests that the mass flux has a value proportional to a flow velocity, and thus a cut depth is not defined by only the maximum flow velocity of a main jet.

Figure 14:
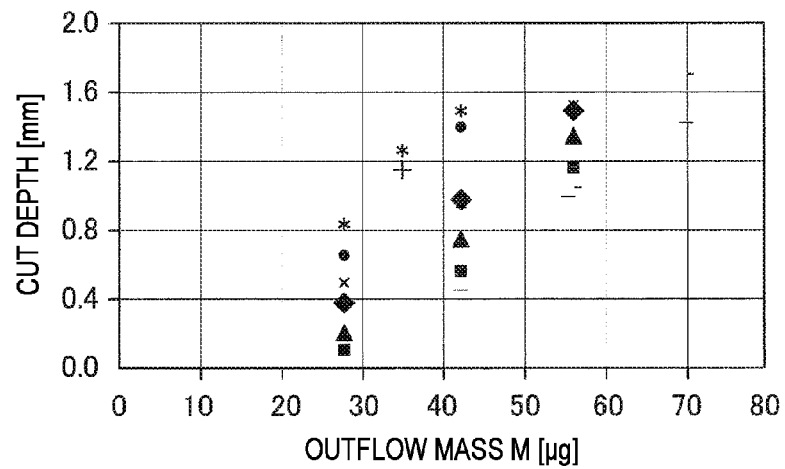
FIG. 14 is a diagram plotting a simulation result of a relationship between a cut depth of a cutting target object and outflow mass.
Figure 15:
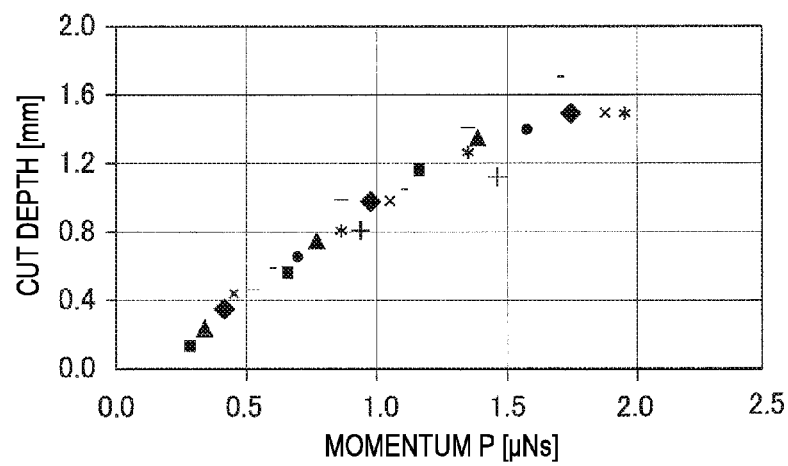
FIG. 15 is a diagram plotting a simulation result of a relationship between a cut depth of a cutting target object and momentum.
Figure 16:
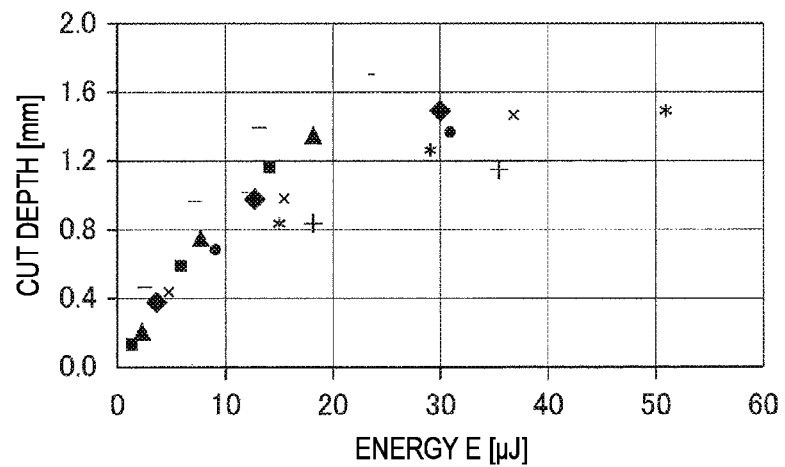
FIG. 16 is a diagram plotting a simulation result of a relationship between a cut depth of a cutting target object and energy.

Next, regarding the relationship between each of the three parameters such as the outflow mass M, the momentum P, and the energy E, illustrated in FIGS. 14 to 16, and the cut depth, the relationship between the outflow mass M and the cut depth greatly varies depending on the shape of the waveform provided as a flow velocity waveform of a main jet, and thus a mutual correlation is low. In contrast, in the relationship with the momentum P or the energy E, a variation due to the shape of the provided waveform is small, and the respective plots are substantially distributed on the same curve. Of the momentum P and the energy E, the momentum P less varies. Therefore, it can be said that the cut depth has a high correlation with the momentum P or the energy E, and is highly correlated with, especially, the momentum P.

Here, the simulation was performed in a case where the diameter of the liquid ejection opening was 0.15 mm, and a standoff distance was 0.5 mm, but simulation was performed for other liquid ejection opening diameters or standoff distances, and it was found that a quantitative tendency that the cut depth is highly correlated with the momentum P or the energy E does not greatly change.

FIGS. 17 to 22 are diagrams respectively plotting simulation results of relationships of the maximum mass flux Jm_max (FIG. 17), the maximum momentum flux Jp_max (FIG. 18), the maximum energy flux Je_max (FIG. 19), the outflow mass M (FIG. 20), the momentum P (FIG. 21), and the energy E (FIG. 22), with respect to a cut volume of a cutting target object. Relationships between waveforms provided as a flow velocity waveform of a main jet and the types of plots are the same as in FIGS. 11 to 16.

Figure 17:
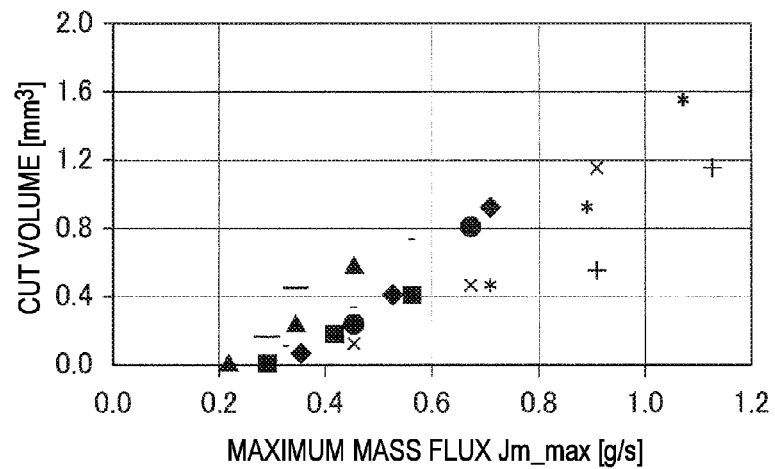
FIG. 17 is a diagram plotting a simulation result of a relationship between a cut volume of a cutting target object and the maximum mass flux.
Figure 18:
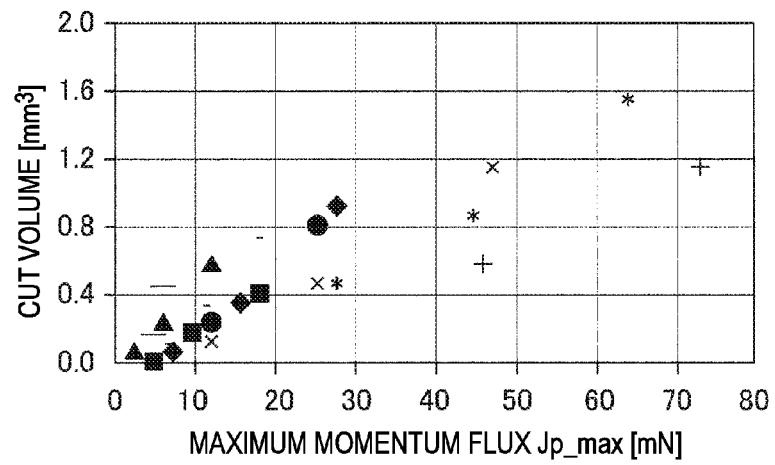
FIG. 18 is a diagram plotting a simulation result of a relationship between a cut volume of a cutting target object and the maximum momentum flux.
Figure 19:
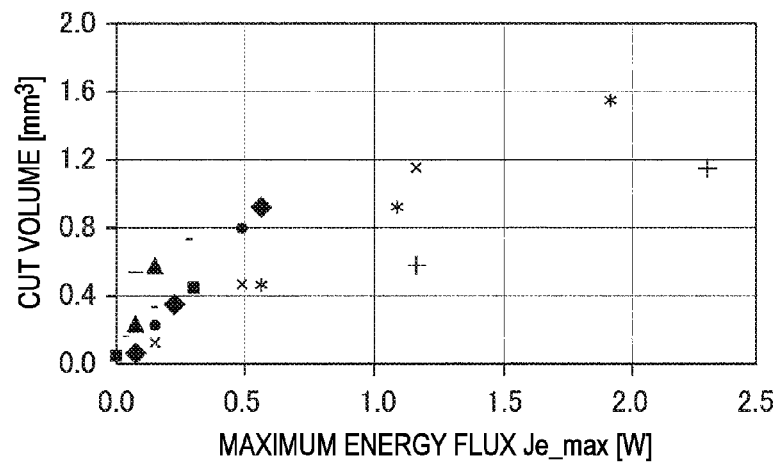
FIG. 19 is a diagram plotting a simulation result of a relationship between a cut volume of a cutting target object and the maximum energy flux.

As illustrated in FIGS. 17 to 19, the relationship between each of the three parameters such as the maximum mass flux Jm_max, the maximum momentum flux Jp_max, and the maximum energy flux Je_max, and the cut volume varies depending on the shape of the waveform provided as a flow velocity waveform of a main jet although not as much as the relationship with the cut depth, and thus it is considered that a mutual correlation is low.

Figure 20:
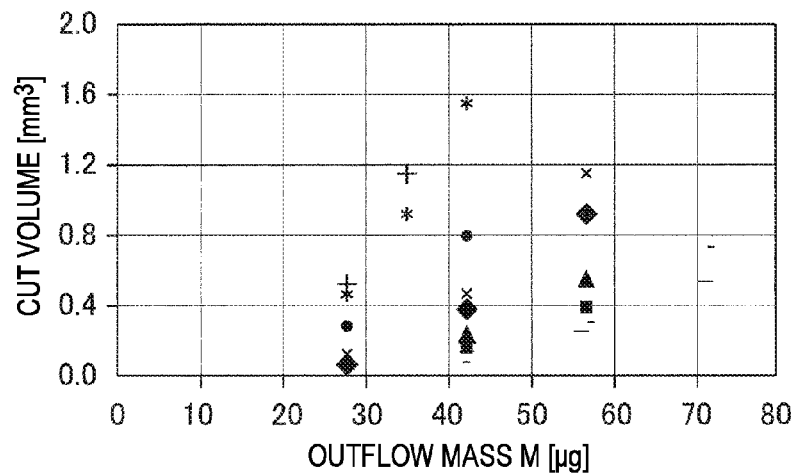
FIG. 20 is a diagram plotting a simulation result of a relationship between a cut volume of a cutting target object and outflow mass.
Figure 21:
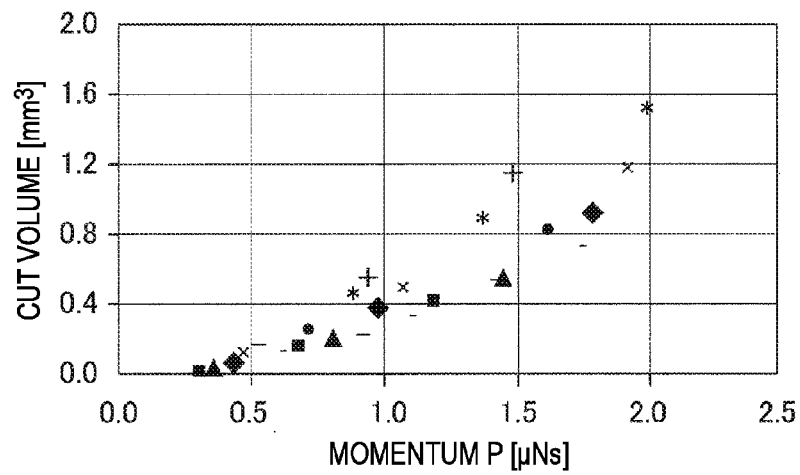
FIG. 21 is a diagram plotting a simulation result of a relationship between a cut volume of a cutting target object and momentum.
Figure 22:
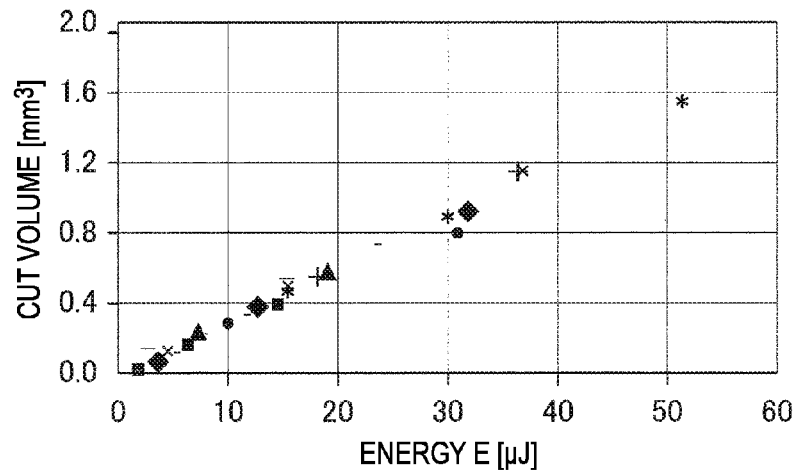
FIG. 22 is a diagram plotting a simulation result of a relationship between a cut volume of a cutting target object and energy.

Next, regarding the relationship between each of the three parameters such as the outflow mass M, the momentum P, and the energy E, illustrated in FIGS. 20 to 22, and the cut volume, the relationship between the outflow mass M and the cut volume greatly varies depending on the shape of the waveform provided as a flow velocity waveform of a main jet in the same manner as in the cut depth, and thus a mutual correlation is low. In contrast, in the relationship with the momentum P or the energy E, a variation due to the shape of the provided waveform is small in the same manner as in the cut depth, and the respective plots are substantially distributed on the same curve. The energy E less varies than the momentum P. Therefore, it can be said that the cut volume has a high correlation with the momentum P or the energy E, and is highly correlated with, especially, the energy E.

Here, the simulation was performed in a case where the diameter of the liquid ejection opening was 0.15 mm, and a standoff distance was 0.5 mm, but simulation was performed for other liquid ejection opening diameters or standoff distances, and it was found that a quantitative tendency that the cut volume is highly correlated with the momentum P or the energy E does not greatly change.

On the basis of the above examination results, in the present embodiment, as an example of "adjusting a cutting aspect using a pulsed liquid jet from a "narrow and deep" aspect to a "wide and shallow" aspect without changing a cut volume if at all possible", the drive voltage waveform L1 is controlled focusing on the energy E, and thus a cutting aspect is changed without greatly changing a cut volume.

For this, first, the flow velocity waveform L3 of the main jet 3 was obtained through simulation by changing control parameters (the rising frequency $F_{pr}$, the voltage amplitude $V_m$, and the repetition frequency $F_p$) of the drive voltage waveform L1. The simulation may be performed, for example, by using numerical value simulation which is based on a model replacing a channel system of the liquid ejection device with fluid (channel) resistance, fluid inertance, fluid compliance, or the like, and which uses an equivalent circuit method. Alternatively, if higher accuracy is required, fluid simulation using a finite element method (FEM), a finite volume method (FVM), or the like may be used.

First, the flow velocity waveform L3 of the main jet 3 is obtained through simulation by providing the drive voltage waveform L1 in which the rising frequency $F_{pr}$ is changed in steps in a state in which the voltage amplitude $V_m$ and the repetition frequency $F_p$ are fixed.

Figure 23:
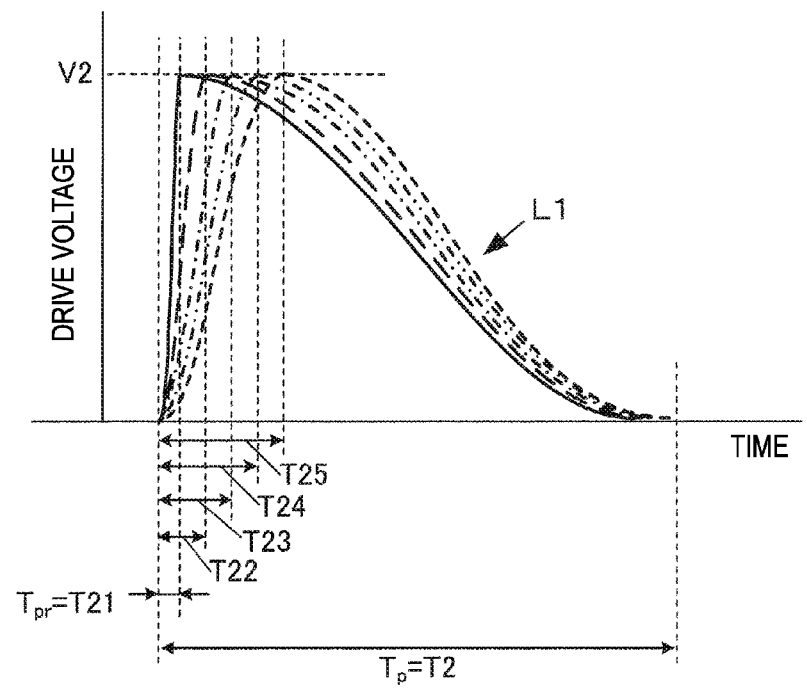
FIG. 23 is a diagram illustrating examples of drive voltage waveforms in which voltage amplitude and a repetition cycle are fixed, and a rising time is changed in steps.

FIG. 23 is a diagram illustrating examples of the provided drive voltage waveforms L1. In each drive voltage waveform L1, the voltage amplitude is V2, the repetition cycle $T_p$ is T2, and the rising time $T_{pr}$ is lengthened in steps from T21 to T25, that is, the rising frequency $F_{pr}$ is lowered in steps.

Figure 24:
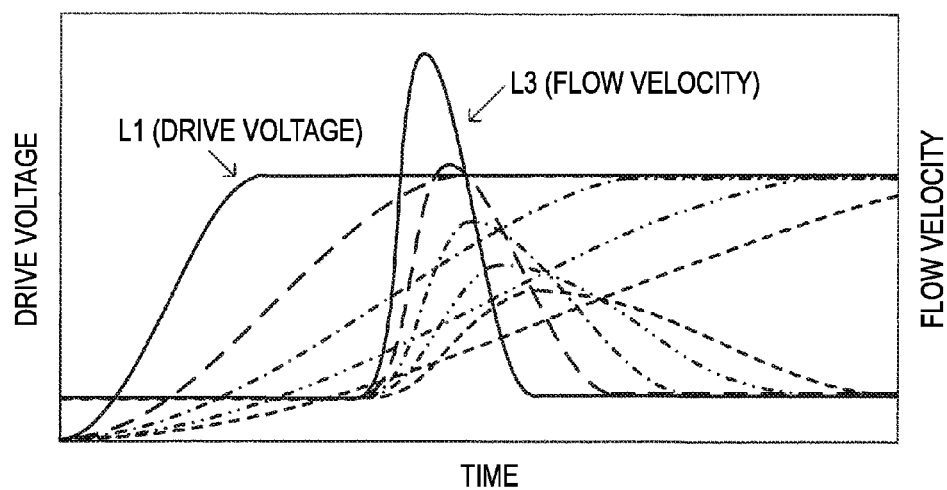
FIG. 24 is a diagram illustrating a simulation result of a flow velocity waveform of a main jet in a case where each drive voltage waveform in FIG. 23 is provided.

FIG. 24 is a diagram illustrating simulation results of the flow velocity waveform L3 of the main jet 3 in a case where the drive voltage waveforms L1 with the different rising frequencies $F_{pr}$ illustrated in FIG. 23 are provided.

As illustrated in FIG. 24, if the rising frequency $F_{pr}$ is low (the rising time $T_p$, is long), in the flow velocity waveform L3 of the main jet 3, a rising start timing does not vary, and the duration T during rising is lengthened, and thus flow velocity amplitude (the maximum value of the flow velocity) is also reduced.

Second, the flow velocity waveform L3 of the main jet 3 is obtained through simulation by providing the drive voltage waveform L1 in which the voltage amplitude $V_m$ is changed in steps in a state in which the rising frequency $F_{pr}$ and the repetition frequency $F_p$ are fixed.

Figure 25:
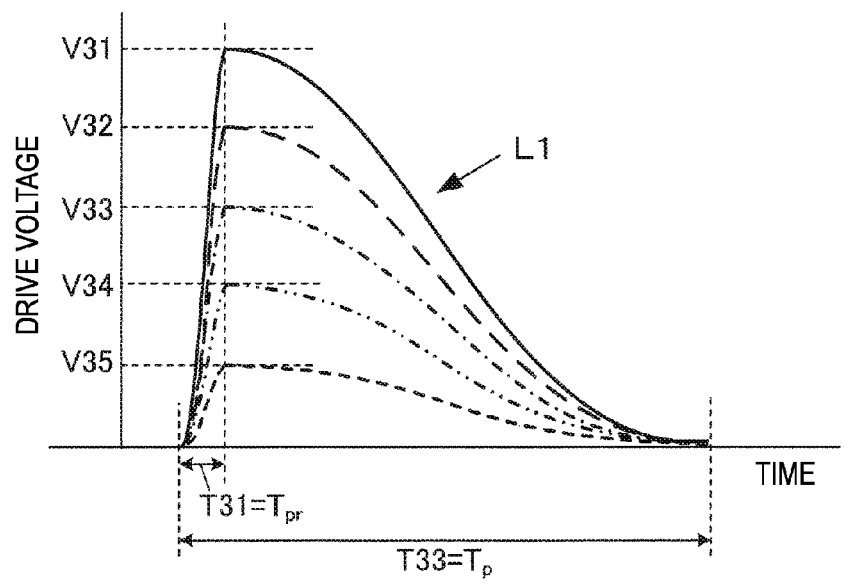
FIG. 25 is a diagram illustrating examples of drive voltage waveforms in which a repetition cycle and a rising time are fixed, and voltage amplitude is changed in steps.

FIG. 25 is a diagram illustrating examples of the provided drive voltage waveforms L1. In each drive voltage waveform L1, the rising time $T_{pr}$ is T31, the repetition cycle $T_p$ is T33, and the voltage amplitude is reduced in steps from V31 to V35.

Figure 26:
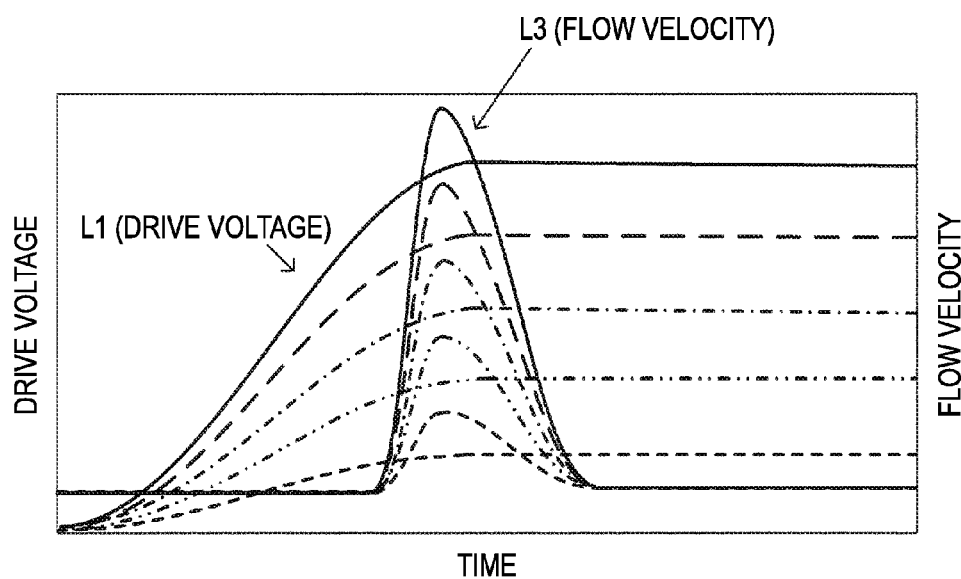
FIG. 26 is a diagram illustrating a simulation result of a flow velocity waveform of a main jet in a case where each drive voltage waveform in FIG. 25 is provided.

FIG. 26 is a diagram illustrating simulation results of the flow velocity waveform of the main jet in a case where the drive voltage waveforms L1 with the different voltage amplitudes $V_m$ illustrated in FIG. 25 are provided.

As illustrated in FIG. 26, if the voltage amplitude $V_m$ is reduced, in the flow velocity waveform L3 of the main jet, the duration T during rising is maintained unlike in the cases of FIGS. 23 and 24 in which the rising frequency $F_{pr}$ is reduced, and flow velocity amplitude (the maximum value of the flow velocity) is reduced.

Third, the flow velocity waveform L3 of the main jet 3 is obtained through simulation by providing the drive voltage waveform L1 in which the repetition frequency $F_p$ is changed in steps in a state in which the rising frequency $F_{pr}$ and the voltage amplitude $V_m$ are fixed.

Figure 27:
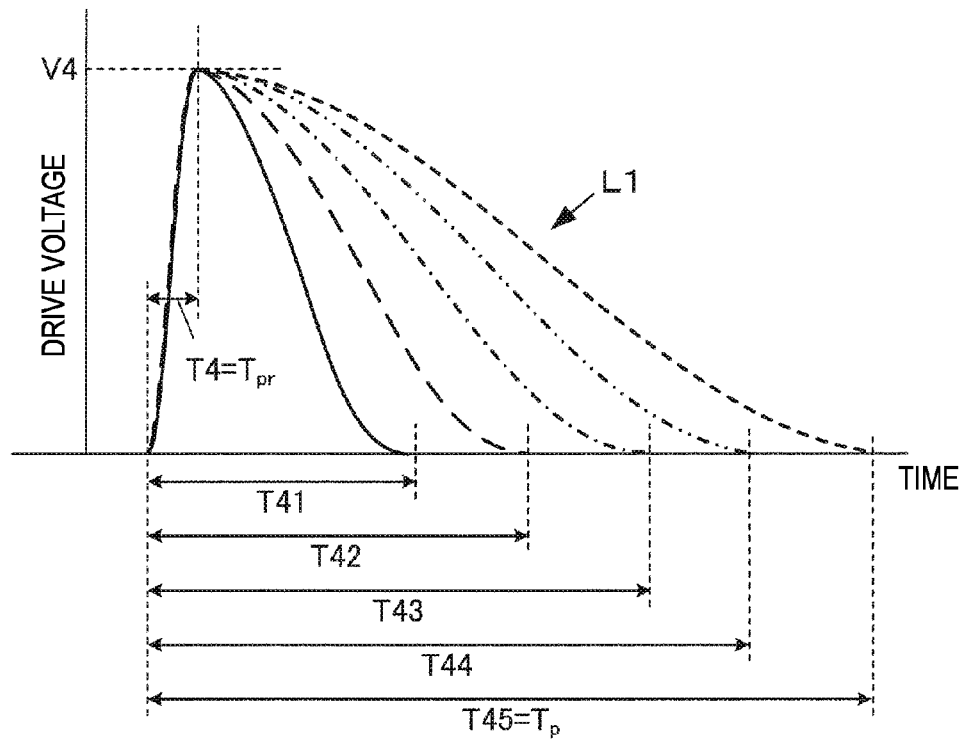
FIG. 27 is a diagram illustrating examples of drive voltage waveforms in which voltage amplitude and a rising time are fixed, and a repetition cycle is changed in steps.

FIG. 27 is a diagram illustrating examples of the provided drive voltage waveforms L1. In each drive voltage waveform L1, the rising time $T_{pr}$ is T4, the voltage amplitude is V4, and the repetition cycle $T_p$ is lengthened in steps from T41 to T45 by extending, in a time axis direction, a falling shape after a drive voltage increases up to the voltage amplitude (the repetition frequency $F_p$ is lowered in steps).

Figure 28:
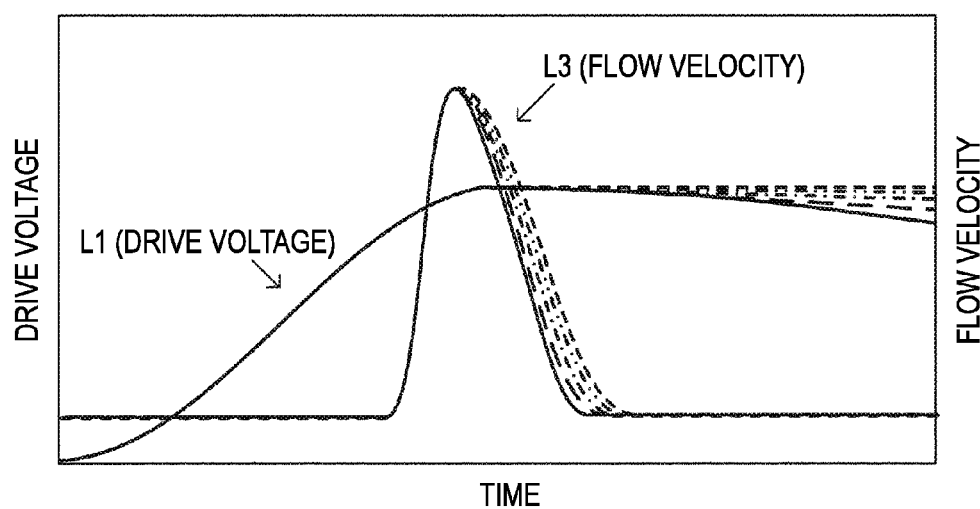
FIG. 28 is a diagram illustrating a simulation result of a flow velocity waveform of a main jet in a case where each drive voltage waveform in FIG. 27 is provided.

FIG. 28 is a diagram illustrating simulation results of the flow velocity waveform L3 of the main jet 3 in a case where the drive voltage waveforms L1 with the different repetition frequencies $F_p$ illustrated in FIG. 27 are provided.

As illustrated in FIG. 28, if the repetition frequency $F_p$ is lowered (the repetition cycle $T_p$ is lengthened), in the flow velocity waveform L3 of the main jet 3, the duration T is slightly lengthened compared with the cases of FIGS. 23 and 24 in which the rising frequency $F_{pr}$ is reduced. The flow velocity amplitude (the maximum value of the flow velocity) is maintained to be constant.

Next, the energy E is obtained on the basis of for each of the obtained flow velocity waveforms L3 of the main jet 3. Specifically, for each repetition frequency $F_p$ while changing the repetition frequency $F_p$ in the way described with reference to FIGS. 27 and 28, simulation is performed in a case where the voltage amplitude $V_m$ is fixed and the rising frequency $F_{pr}$ is changed in the way described with reference to FIGS. 23 and 24 and simulation is performed in a case where the rising frequency $F_{pr}$ is fixed and the voltage amplitude $V_m$ is changed in the way described with reference to FIGS. 25 and 26. The energy E of the flow velocity waveform L3 of the main jet 3 obtained through each simulation is obtained.

Figure 29:
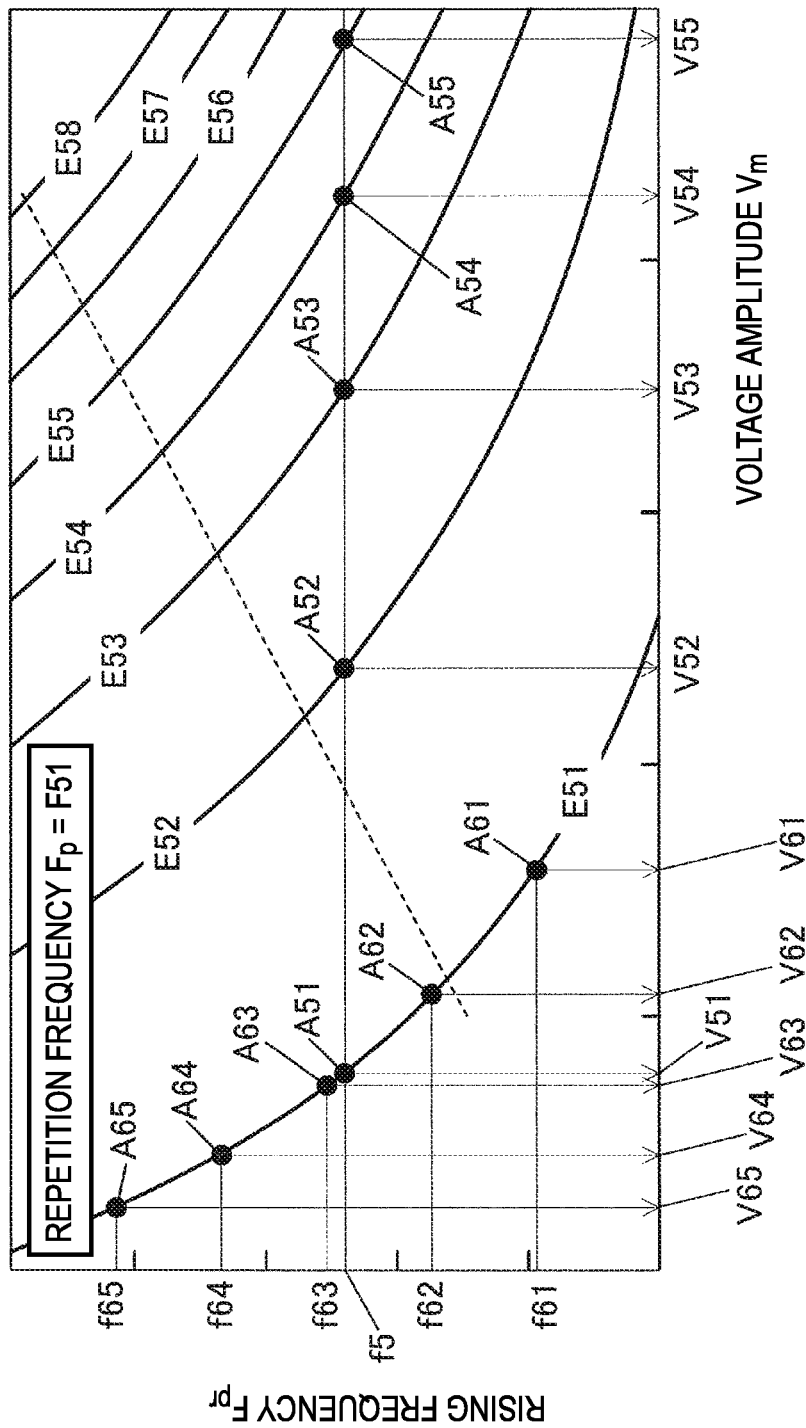
FIG. 29 is a diagram illustrating a relationship among voltage amplitude, a rising frequency, and energy in a case where a repetition frequency is fixed.

FIG. 29 is a diagram illustrating correspondence relationships among the energy E obtained at a predetermined repetition frequency (for example, "F51"), the rising frequency $F_{pr}$, and the voltage amplitude $V_m$, and is obtained by drawing contour lines regarding the energy E in a coordinate space in which a longitudinal axis expresses the rising frequency $F_{pr}$, and a transverse axis expresses the voltage amplitude $V_m$. Energies E51, E52, . . . of the respective contour lines are low on the lower left side, and increase by a predetermined amount toward the upper right side. Although not illustrated, if contour lines are drawn by plotting the energy E obtained at the same repetition frequency $F_p$ in the same coordinate space, a contour map corresponding to correspondence relationships among the energy E at the repetition frequency $F_p$, the rising frequency $F_{pr}$, and the voltage amplitude $V_m$ is obtained.

Here, it is noted that the energy E does not linearly change for the parameter in each coordinate axis direction.

For example, in the correspondence relationships among the energy E, the rising frequency $F_{pr}$, and the voltage amplitude $V_m$, a case is assumed that the rising frequency $F_{pr}$ is fixed (to f5, for example), the drive voltage waveform L1 of the piezoelectric element 45 is controlled by changing the voltage amplitude $V_m$.

If an amount of to the energy E to be changed is to be constant in order not to change a cut volume if at all possible, a voltage amplitude change between the voltage amplitudes V51 and V52 is necessary between the energies E51 and E52, and a voltage amplitude change between the voltage amplitudes V52 and V53 is necessary between the energies E52 and E53. However, a voltage amplitude gap between the voltage amplitudes V51 and V52 is different from a voltage amplitude gap between the voltage amplitudes V52 and V53. This phenomenon notably appears as the energy E increases.

Therefore, even if the voltage amplitude $V_m$ is controlled to be changed by a predetermined amount in a state in which the rising frequency $F_{pr}$ is fixed in order not to change a cut volume if at all possible, a situation in which the energy E changes may occur. This may also be same for a case where an operation of changing the rising frequency $F_{pr}$ by a predetermined amount in a state in which the voltage amplitude $V_m$ is fixed.

Therefore, in the present embodiment, at least an operation of setting the energy E is received as an operation performed by a user during surgery, and correspondence relationships among the energy E, the rising frequency $F_{pr}$, and the voltage amplitude $V_m$ for each repetition frequency $F_p$ are prepared in advance as table data on the basis of the contour map obtained for each repetition frequency $F_p$ as described above. Combinations of values of the respective control parameters (the repetition frequency $F_p$, the rising frequency $F_{pr}$, and the voltage amplitude $V_m$) for realizing the energy E set by the user are determined, and thus driving of the piezoelectric element 45 is controlled. Consequently, control for not greatly changing a cut volume is realized.

Next, regarding control of the drive voltage waveform L1 for "adjusting a cutting aspect using a pulsed liquid jet from a "narrow and deep" aspect to a "wide and shallow" aspect without changing a cut volume if at all possible", a principle of the portion "adjusting a cutting aspect" will be described.

Figure 30:
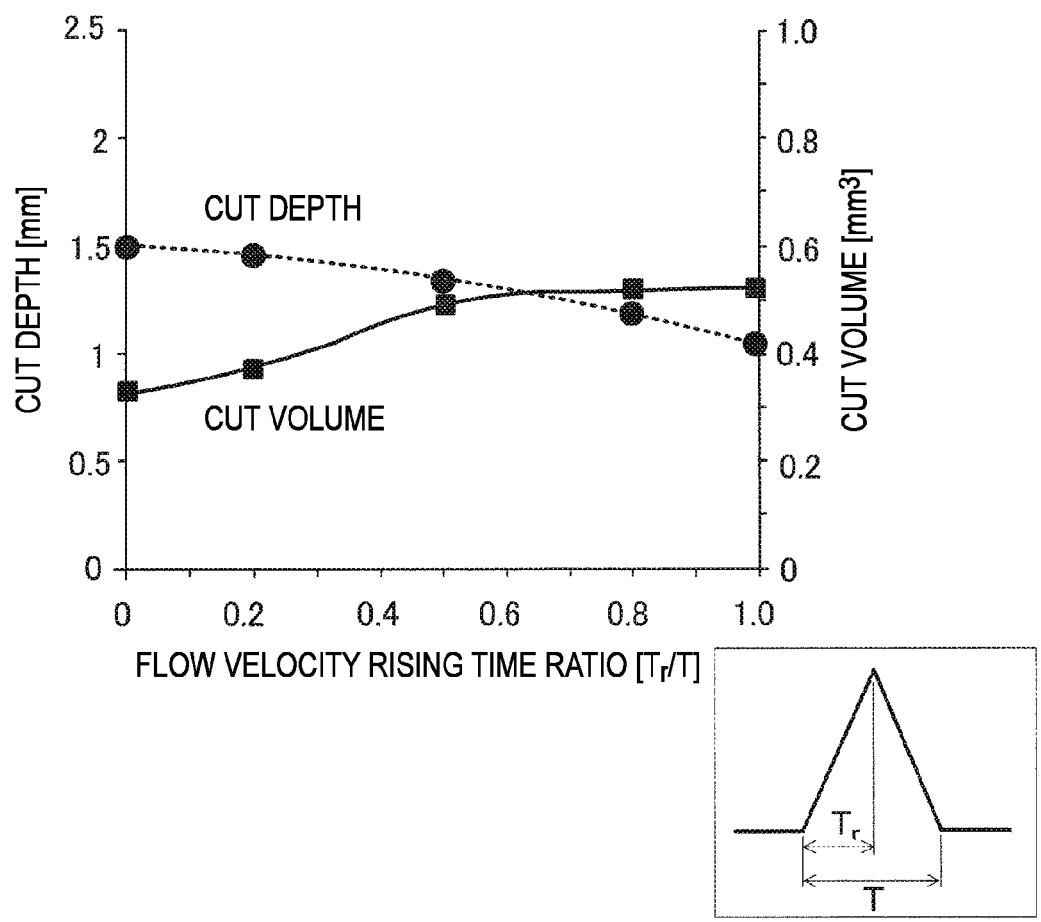
FIG. 30 is a graph illustrating a simulation result of a cut depth and a cut volume in a case where a flow velocity rising time ratio is changed when the voltage amplitude of a drive voltage waveform causing a flow velocity waveform to be a triangular wave is fixed.
Figure 31:
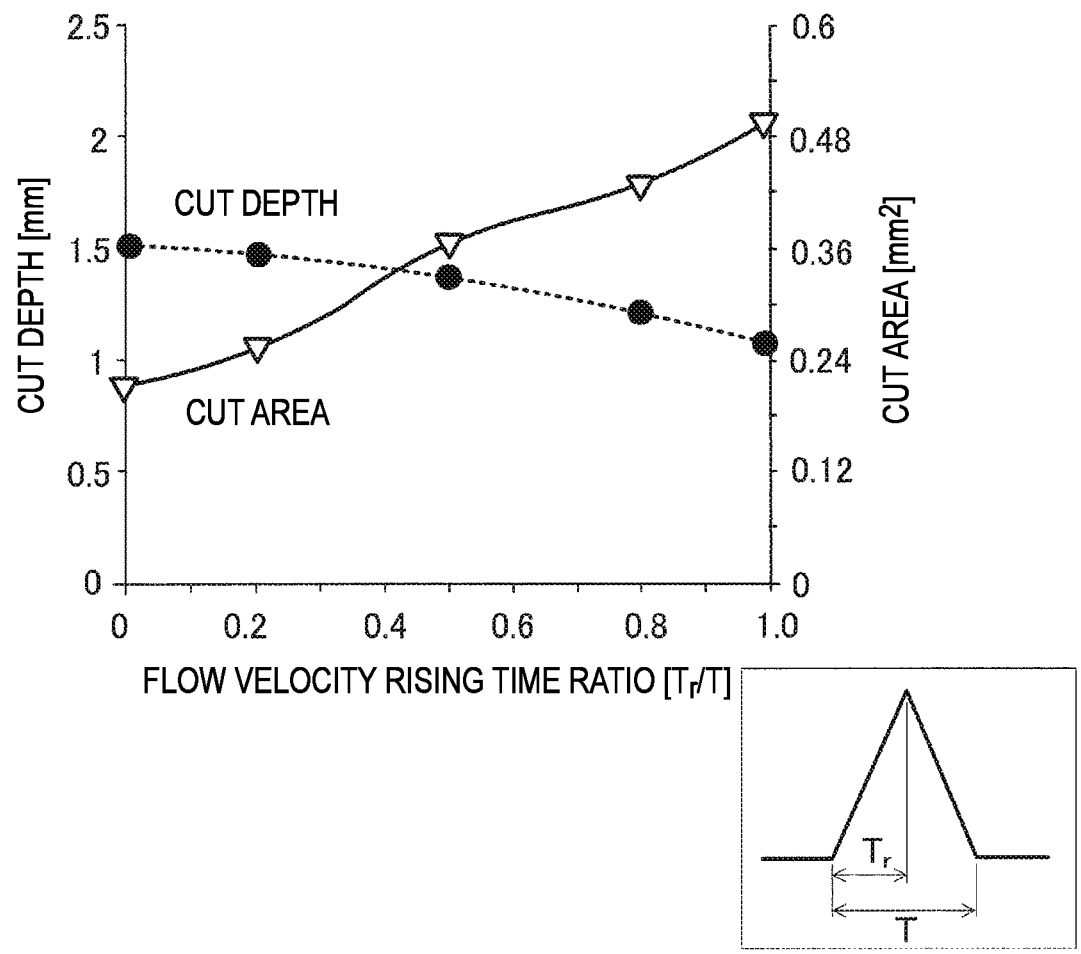
FIG. 31 is a graph illustrating a simulation result of a cut depth and a cut area in a case where a flow velocity rising time ratio is changed when the voltage amplitude of a drive voltage waveform causing a flow velocity waveform to be a triangular wave is fixed.
Figure 32:
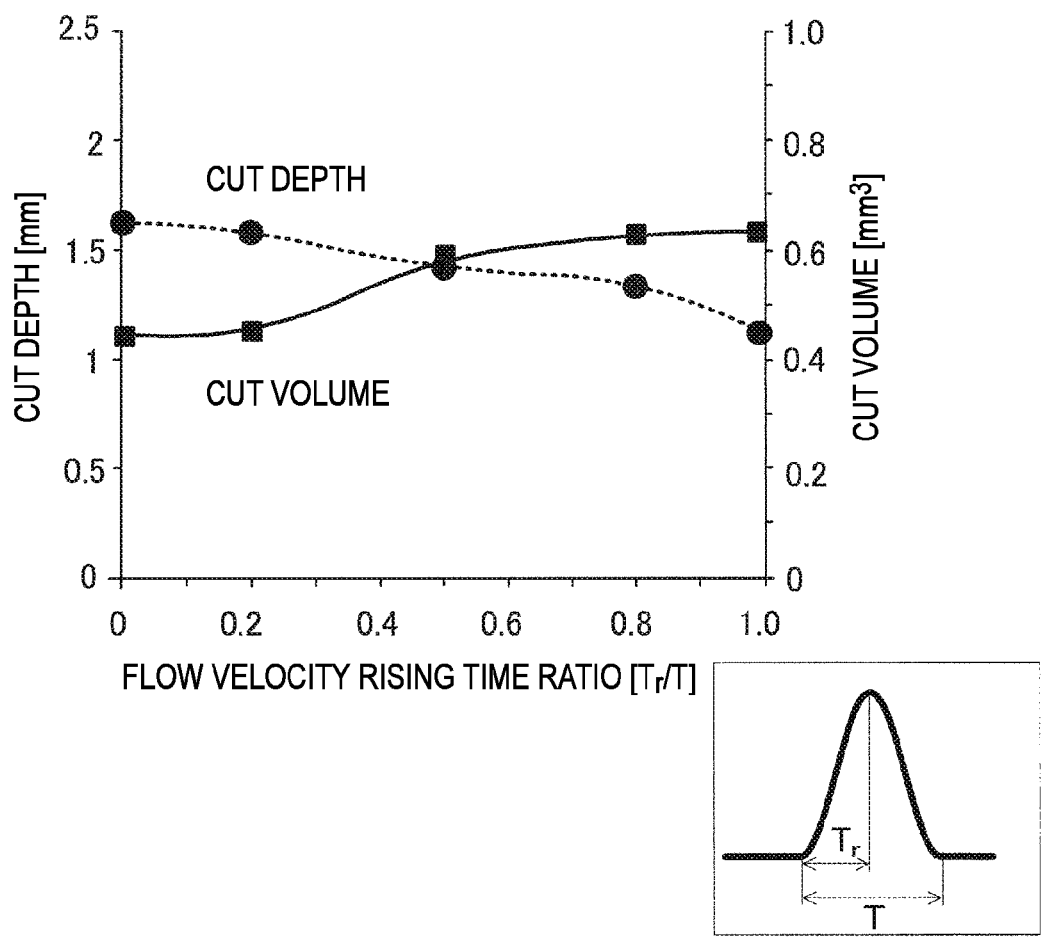
FIG. 32 is a graph illustrating a simulation result of a cut depth and a cut volume in a case where a flow velocity rising time ratio is changed when the voltage amplitude of a drive voltage waveform causing a flow velocity waveform to be a squared sine wave is fixed.

FIGS. 30 to 32 are graphs illustrating simulation results of three elements (a cut depth, a cut volume, and a cut area) indicating cutting aspects (cutting states) in a case where a flow velocity rising time ratio is changed in a state in which the voltage amplitude $V_m$ of the drive voltage waveform L1 is fixed. The cut area is an area of a surface orthogonal to a cutting depth direction, and is an index indicating narrow cutting or wide cutting.

A pulsed liquid jet is a fluid, and a cutting target object is a soft elastic body. Therefore, a cutting aspect using the pulsed liquid jet was simulated as a destruction behavior of the cutting target object using the pulsed liquid jet. As a computation method in the simulation, in the present embodiment, an appropriate destruction threshold value is set on the soft elastic body side, and then so-called interaction analysis (fluid structure interaction (FSI) analysis) of the fluid and a structure (here, the soft elastic body) is employed, but a finite element method (FEM), a method using a particle method whose representative is a smoothed particle hydrodynamics (SPH), and a method of combining the finite element method with the particle method may be employed.

When the simulation was performed, a diameter of the liquid ejection opening 61=0.15 mm, and a standoff distance (a distance from the liquid ejection opening 61 to a surface of the cutting target object)=1.0 mm were set. Assuming that the cutting target object was a soft elastic body having a flat surface, a Mooney-Rivlin super-elastic body having an elastic modulus of about 9 kPa (about 3 kPa in terms of shear modulus) in terms of Young's modulus was used as a physical model thereof. Equivalent deviation strain=0.7 was used in the destruction threshold value. Both of the density of the liquid and the density of the soft elastic body were 1 g/cm$^3$.

Regarding the flow velocity waveform L3 of the main jet 3 which is forced to be applied to a nozzle hole outlet and is ejected onto a cutting target object, the maximum amplitude of the flow velocity was fixed to 50 m/s, the duration was fixed to 125 µs, and various flow velocity waveforms L3 in which the maximum flow velocity occurs at various time points were assumed with a flow velocity waveform in which a flow velocity rising time is 62.5 µs as a "reference waveform". Specifically, five levels such as 1 µs, 25 µs, 62.5 µs, 100 µs, and 124 µs were assumed as a timing (=flow velocity rising time $T_r$) in which the maximum flow velocity occurs in the flow velocity waveform L3. A flow velocity of a steady flow was 1 m/s.

Figure 33:
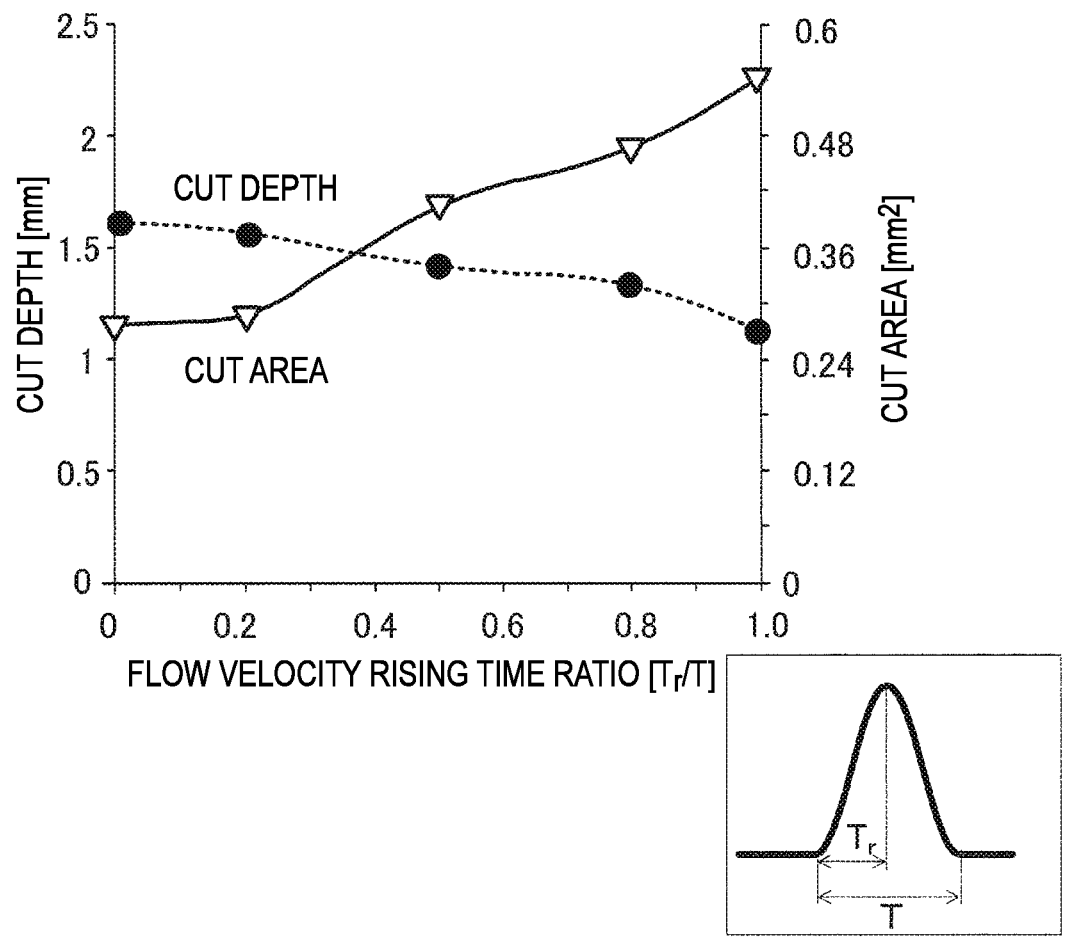
FIG. 33 is a graph illustrating a simulation result of a cut depth and a cut volume in a case where a flow velocity rising time ratio is changed when the voltage amplitude of a drive voltage waveform causing a flow velocity waveform to be a squared sine wave is fixed.

As the flow velocity waveform L3, a triangular wave expressed by Equation (7) and a squared sine wave expressed by Equation (8) were assumed. FIGS. 30 and 31 illustrate simulation results of employing the former, and FIGS. 32 and 33 illustrate simulation results of employing the latter.

$$u = \begin{cases} U_{BG} + \Delta U_m \dfrac{t}{T_r} & (0 \le t \le T_r) \\ U_{BG} + \Delta U_m \dfrac{(T-t)}{T_f} & (T_r \le t \le T) \end{cases} \quad (7)$$

$$u = \begin{cases} U_{BG} + \Delta U_m \sin^2\left(\dfrac{\pi}{2} \cdot \dfrac{t}{T_r}\right) & (0 \le t \le T_r) \\ U_{BG} + \Delta U_m \sin^2\left(\dfrac{\pi}{2} \cdot \dfrac{(T-t)}{T_f}\right) & (T_r \le t \le T) \end{cases} \quad (8)$$

In these equations, $U_{BG}$ indicates a steady flow of 1 m/s, $\Delta U_m$ indicates the flow velocity maximum amplitude of 50 m/s, and T indicates the main jet duration of 125 µs. $T_r$ is the flow velocity rising time $T_r$, $T^f$ is the flow velocity falling time, and a sum of $T_r$ and $T_f$ is the duration T ($T=T_r+T_f$) of the main jet 3.

It is noted that the maximum mass flux [kg/s], the maximum momentum flux [Ns/S=N], the maximum energy flux [J/s=W], outflow mass [kg], outflow momentum [Ns], and outflow energy [J] regarding a pulsation component obtained by excluding an amount corresponding to a background (an amount corresponding to a steady flow) are exactly the same for the main jet flow velocity waveforms of two types although flow velocity rising times are different each other.

It can be seen from the simulation results illustrated in FIGS. 30 to 33 that there is a tendency that a cut depth decreases as "$T_r/T$" increases regardless of the type of flow velocity waveform. In other words, it can be said that if the main jet is ejected with a flow velocity waveform in which a flow velocity peak timing of the main jet 3 is relatively early, cutting can be performed in a "narrow and deep" aspect. Conversely, it can be said that it can be said that if the main jet is ejected with a flow velocity waveform in which a flow velocity peak timing of the main jet 3 is relatively late, cutting can be performed in a "wide and shallow" aspect. In other words, even if the momentum P or the energy E of the main jet 3 is the same, cutting in various cutting aspects from a "narrow and deep" aspect to a "wide and shallow" aspect can be realized by adjusting "$T_r/T$".

The same simulation was performed by using flow velocity waveforms other than the triangular wave expressed by Equation (7) and the squared sine wave expressed by Equation (8), and this tendency does not change.

Next, a description will be made of a method of adjusting the flow velocity rising time ratio "$T_r/T$", that is, a method of adjusting a flow velocity peak timing of the main jet 3.

In actual use, the drive voltage waveform L1 (fundamental drive voltage waveform: refer to FIG. 3) corresponding to one cycle of drive voltage waveforms is applied from several tens of times to several hundreds of times per second, that is, at the repetition frequency $F_p$ of several tens of Hz to several hundreds of Hz. The drive voltage waveform L1 of one cycle may be regarded to be formed of two waveform portions. In other words, the two portions are a "rising portion" from a voltage of "0" till reaching the start voltage amplitude $V_m$, and a "falling portion" which slowly decreases from the voltage amplitude $V_m$ and reaches the voltage of "0" again.

Figure 34:
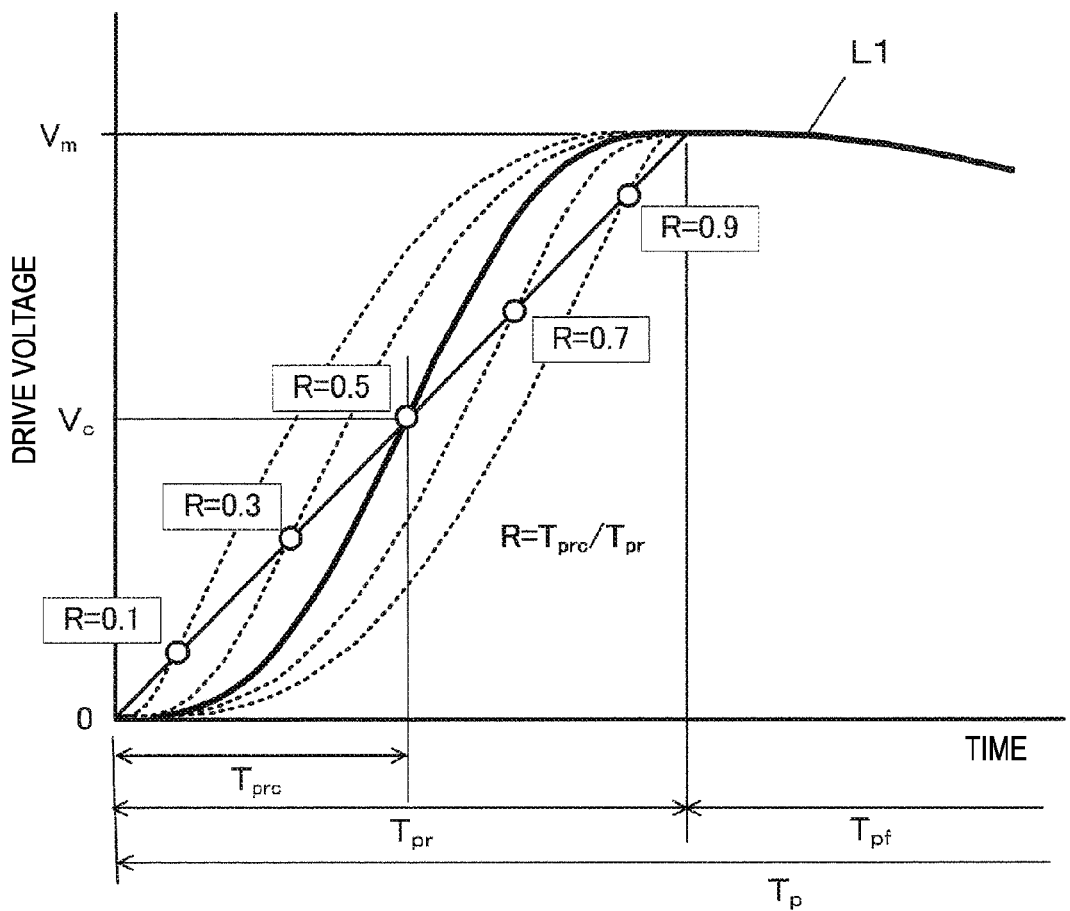
FIG. 34 is an enlarged view of a rising portion of a fundamental drive voltage waveform.

FIG. 34 is an enlarged view of the rising portion of the drive voltage waveform L1 of one cycle.

Focusing on the "rising portion" in relation to an inflection point (at a position of R=0.5 in the example illustrated in FIG. 34) of a waveform curve, it can be seen that the rising portion is formed of two curve portions such as a portion which increases along a curve projecting downwardly from the drive voltage of "0" and reaches the "inflection point" and a portion which reaches the voltage amplitude $V_m$ along a curve projecting upwardly from the "inflection point". The piezoelectric element 45 is substantially linearly expanded for the drive voltage, and thus it can be said that the "inflection point" corresponds to a peak of the flow velocity waveform L3 of the main jet 3. Therefore, if a position of the inflection point is moved, it is possible to adjust the flow velocity rising time ratio "$T_r/T$", that is, to adjust a flow velocity peak timing of the main jet 3.

Next, a description will be made of a method of modifying the fundamental drive voltage waveform (the drive voltage waveform L1 of one cycle) in order to move an inflection point.

In the present embodiment, an inflection point is moved along a line segment connecting a "rising start point (a point of drive voltage=0)" to a "rising end point (drive voltage=voltage amplitude)" of the drive voltage waveform. Consequently, "$T_r/T$", that is, a front-and-rear ratio of the rising portion is changed without greatly changing the momentum P or the energy E of the main jet 3. Therefore, various cutting aspects such as a "narrow and deep" aspect or a "wide and shallow" aspect without changing a cutting amount of a target substance.

Specifically, a drive voltage $V_p$ with the fundamental drive voltage waveform may be expressed as a function with a time point t as a variable in a domain in which an upper limit of the time point t is the repetition cycle $T_p$ as in the following Equation (9).

$$V_p = V(t) \ (0 \le t \le T_p) \quad (9)$$

The drive voltage $V_p$ in the rising portion during the rising time $T_{pr}$ may be expressed by the following Equation (10).

$$V_p = V(t) \ (0 \le t \le T_{pr}) \quad (10)$$

In the rising portion, the drive voltage $V_p$ with the fundamental drive voltage waveform (the drive voltage waveform L1 of one cycle) at the rising start point, that is, the time point of "0" is "0", and the drive voltage $V_p$ at the rising end point, that is, the time point $T_p$, is the voltage amplitude $V_m$. In other words, the following Equation (11) is satisfied.

$$V(0)=0, \text{ and } V(T_{pr})=V_m \quad (11)$$

Here, the rising portion intersects a line segment connecting the rising start point to the rising end point at a time point $T_{prc}$. This will be referred to as an "intersection". If a voltage at this time is a voltage $V_c$ with the fundamental drive voltage waveform (the drive voltage waveform L1 of one cycle), the following Equation (12) is satisfied.

$$V(T_{prc}) = V_c = (V_m/T_{pr})T_{prc} \quad (12)$$

The rising portion is modified on the basis of the following concepts of a) to c).

In other words, a) the rising portion is enlarged or reduced with unmagnification in a voltage axis direction or a time axis direction before the "intersection" with the "rising start point (drive voltage=0)" as a base point.

b) The rising portion is enlarged or reduced with unmagnification in the voltage axis direction or the time axis direction after the "intersection" with the "rising end point (voltage amplitude $V_m$)" as a base point.

c) The rising portion and the falling portion are smoothly connected to each other at a movement destination of the "intersection".

Specifically, it is assumed that the "intersection" is modified to become M times and M' times in the voltage axis direction and the time axis direction, respectively, with the "rising start point" and the "rising end point" as base points, and a point $(t, V_p)$ on the rising portion is moved to a point $(t^*, V_p^*)$. Then, the following Equations (13) and (14) are satisfied.

$$t^*/t = V_p^*/V_p = M \ (0 \le t < T_{prc}) \quad (13)$$

$$(T_{pr}-t^*)/(T_{pr}-t) = (V_m-V_p^*)/(V_m-V_p) = M' \ (T_{prc} \le t \le T_{pr}) \quad (14)$$

Here, M' is expressed by the following Equation (15).

$$M' = (T_{pr}-MT_{prc})/(T_{pr}-T_{prc}) = (V_m-MV_c)/(V_m-V_c) \quad (15)$$

Therefore, the rising portion obtained after the "intersection" is moved may be expressed by the following Equation (16).

$$V_p = \begin{cases} MV\left(\dfrac{t}{M}\right) & (0 \le t \le MT_{prc}) \\ \dfrac{V_m - MV_c}{V_m - V_c}\left[V\left(\dfrac{T_{pr} - T_{prc}}{T_{pr} - MT_{prc}}(t - T_{pr}) + T_{pr}\right) - V_m\right] + V_m & (MT_{prc} \le t \le T_{pr}) \end{cases} \quad (16)$$

Here, Equation (17) is introduced as an index indicating a ratio of the time $MT_{prc}$ of the moved "intersection" to the rising time $T_{pr}$.

$$R = MT_{prc}/T_{pr} \quad (17)$$

As a result, the rising portion after the "intersection" is moved is generalized to Equation (18) again.

$$V_p = \begin{cases} \dfrac{RT_{pr}}{T_{prc}}V\left(\dfrac{tT_{prc}}{RT_{pr}}\right) & (0 \le t \le RT_{pr}) \\ \dfrac{V_m - RV_m}{V_m - V_c}\left[V\left(\dfrac{T_{pr} - T_{prc}}{T_{pr} - RT_{pr}}(t - T_{pr}) + T_{pr}\right) - V_m\right] + V_m & (RT_{prc} \le t \le T_{pr}) \end{cases} \quad (18)$$

Next, a description will be made of a case where the "intersection" of the fundamental drive voltage waveform before being modified is an "inflection point", and the "inflection point" is located exactly at the center ($t = T_{prc} = T_{pr}/2$).

In this case, R can be changed in the range of $0 < R < 1$, and thus the user can perform an input operation of changing R. For example, a value of R may be changed by operating a dial switch or a button switch. A changing width or the number of steps to be changed may be set as appropriate, and, for example, states such as "0.1", "0.3", "0.5", "0.7", and "0.9" may be set. The fundamental driving waveform is not changed at R=0.5. In this case, the rising portion after a modification operation is performed may be expressed by Equation (19) more simply.

$$V_p = \begin{cases} 2RV\left(\dfrac{t}{2R}\right) & (0 \le t \le RT_{pr}) \\ 2(1-R)\left[V\left(\dfrac{t - T_{pr}}{2(1-R)} + T_{pr}\right) - V_m\right] + V_m & (RT_{pr} \le t \le T_{pr}) \end{cases} \quad (19)$$

If a differential waveform of the drive voltage waveform is a triangular wave, and the drive voltage waveform is set so that a flow velocity waveform becomes a triangular wave, Equation (19) of the rising portion may be expressed by the following Equation (20).

$$V_p = \begin{cases} 2V_m\left(\dfrac{t}{T_{pr}}\right)^2 & \left(0 \le t \le \dfrac{T_{pr}}{2}\right) \\ V_m\left[1 - 2\left(\dfrac{t}{T_{pr}} - 1\right)^2\right] & \left(\dfrac{T_{pr}}{2} \le t \le T_{pr}\right) \end{cases} \quad (20)$$

If the user can set a value of R by using a dial switch or a button switch, the rising portion is expressed by following Equation (21).

$$V_p = \begin{cases} 4RV_m\left(\dfrac{t}{2RT_{pr}}\right)^2 & (0 \le t \le RT_{pr}) \\ -4(1-R)V_m\left(\dfrac{t - T_{pr}}{2(1-R)T_{pr}}\right)^2 + V_m & (RT_{pr} \le t \le T_{pr}) \end{cases} \quad (21)$$

On the other hand, if a differential waveform of the drive voltage waveform is a squared sine wave ($\sin_2(x)$) which starts slowly and decreases slowly (a second order differential coefficient is zero at the rising start point and the rising end point), the rising portion is expressed by the following Equation (22).

$$V_p = V_m\left(\dfrac{t}{T_{pr}} - \dfrac{1}{2\pi}\sin\left(2\pi\dfrac{t}{T_{pr}}\right)\right)(0 \le t \le RT_{pr}) \quad (22)$$

If the user can set a value of R by using a dial switch or a button switch, the rising portion is expressed by following Equation (23).

$$V_p = \quad (23)$$
$$\begin{cases} RV_m\left(\dfrac{t}{RT_{pr}} - \dfrac{1}{\pi}\sin\left(\pi\dfrac{t}{RT_{pr}}\right)\right) & (0 \le t \le RT_{pr}) \\ (1-R)V_m\left(\dfrac{t - T_{pr}}{(1-R)T_{pr}} - \dfrac{1}{\pi}\sin\left(\dfrac{t - T_{pr}}{(1-R)T_{pr}}\right)\right) + V_m & (RT_{pr} \le t \le T_{pr}) \end{cases}$$

Here, the "falling portion" will be described.

The falling portion is a decrease portion which slowly decreases and then returns to a drive voltage of "0" after the fundamental drive voltage (the drive voltage waveform L1 of one cycle) reaches the voltage amplitude $V_m$, and slightly influences a flow velocity waveform, and thus the influence is not great. However, the falling portion is preferably smoothly connected to preceding and following rising portions. In other words, preferably, the falling portion is smoothly connected to the voltage amplitude $V_m$ of the rising portion, slowly decreased therefrom for a sufficiently longer time than the rising time, and smoothly connected to the rising portion of the next cycle at the drive voltage of "0". A waveform of the falling portion may be set to, for example, a waveform of a linear function, but is set to, for example, the following Equation (24) or (25) in the present embodiment from the viewpoint of the rising portion and the falling portion being preferably smoothly connected to each other.

$$V_p = \dfrac{V_m}{2}\left(1 - \cos\left(\pi\dfrac{T_p - t}{T_p - T_{pr}}\right)\right)(T_{pr} \le t \le T_p) \quad (24)$$

$$V_p = V_m\dfrac{(T_p - 3T_{pr} + 2t)(T_p - t)^2}{(T_p - T_{pr})^3}(T_{pr} \le t \le T_p) \quad (25)$$

Description of User Interface

Figure 35:
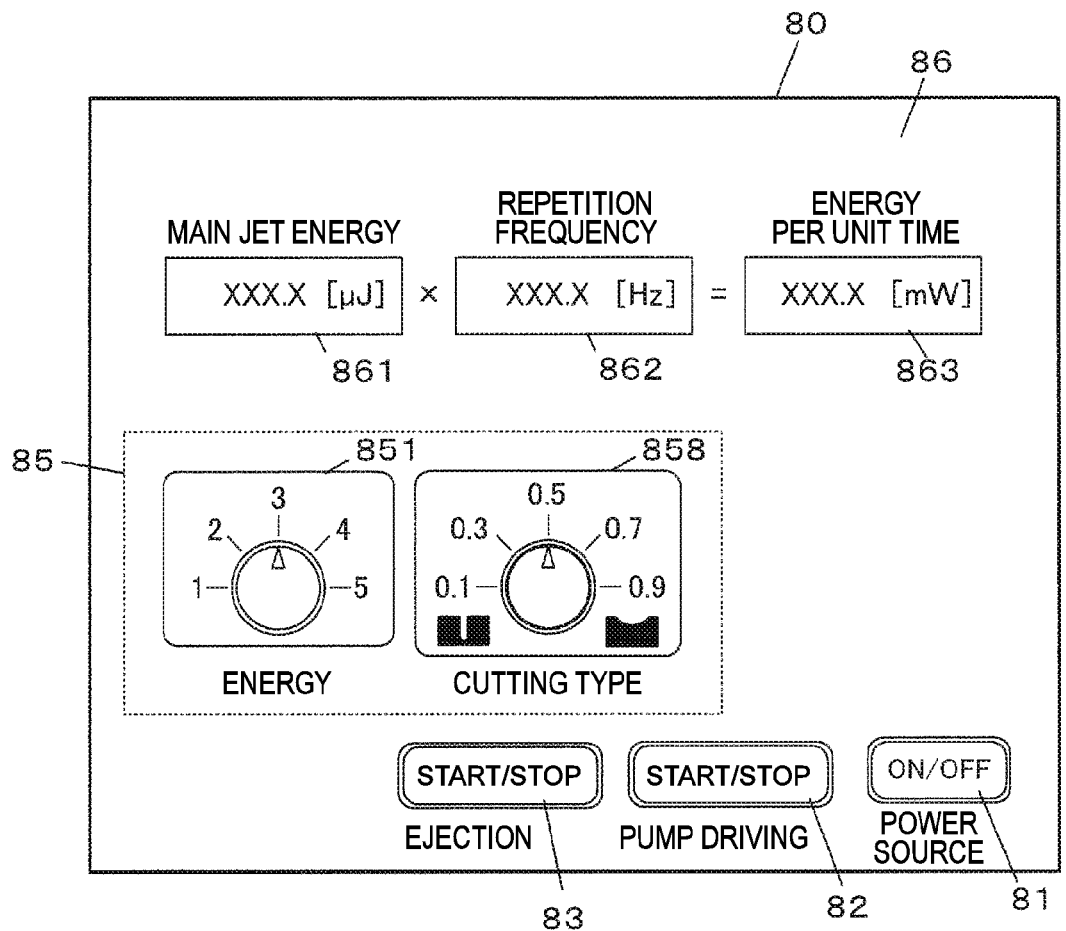
FIG. 35 is a diagram illustrating a configuration example of an operation panel of a liquid ejection control apparatus in a first embodiment.

FIG. 35 is a diagram illustrating a configuration example of the operation panel 80 of the liquid ejection control apparatus 70 in the present embodiment. The operation panel 80 of the present embodiment includes a main power source switch 81, a pump switch 82, a jet ejection switch 83, a jet setting operation portion 85, and a flat panel display 86.

The main power source switch 81 receives an ON or OFF operation on a main power source of the liquid ejection system 1 (refer to FIG. 1).

The pump switch 82 receives an ON or OFF operation on the liquid feeding pump 20 (refer to FIG. 1). If the switch is turned on, the liquid feeding pump 20 is driven, and thus a liquid is supplied from the container 10 to the liquid ejection device 30.

The jet ejection switch 83 receives an operation of driving or stopping the pulse flow generator 40, and provides the same function as that of the ejection pedal 88 illustrated in FIG. 1. If the pump switch 82 is turned on, a steady flow is only supplied to the liquid ejection device 30, and a liquid flows out of the nozzle 60 in a state in which there is no pulse (a state of the steady flow). However, the jet ejection switch 83 is turned on, a drive voltage corresponding to a set input operation in the jet setting operation portion 85 is applied to the piezoelectric element 45 (refer to FIG. 2) of the pulse flow generator 40, and thus a pulsed liquid jet is ejected from the nozzle 60.

The jet setting operation portion 85 receives various setting operations for adjusting a pulsed liquid jet to a state desired by the user. The jet setting operation portion 85 of the present embodiment includes an energy dial 851 and a cutting type dial 858.

The energy dial 851 is an operation portion which receives input of a set value of the energy E of the main jet 3, that is, setting of the strength of the main jet 3. For example, the energy dial 851 is configured to allow dial positions in five steps, provided with scales such as "1" to "5", to be selected. Energy indication values are allocated in advance to the respective diameter positions so as to be increased by a predetermined level in proportion to a numerical value of a corresponding scale, for example. The user can operate the strength of the main jet 3 by switching an indication position of the energy dial 851. The number of steps of the dial positions is not limited to five steps, and may be set as appropriate, for example, three steps such as "large", "intermediate", and "small", or adjustment may be performed steplessly.

The cutting type dial 858 is an operation portion which receives setting of a cutting aspect (cutting state) such as a "narrow and deep" aspect or a "wide and shallow" aspect. Specifically, dial positions of "0.1", "0.3", "0.5", "0.7", and "0.9" corresponding to values of R (refer to FIG. 34) are set in the cutting type dial 858. In other words, the cutting type dial 858 is an operation portion which receives an operation of setting an inflection point position of a rising portion in a drive voltage waveform, and functions as an operation portion which receives input of an index value for setting a flow velocity peak timing of a main jet of a pulsed liquid jet.

The flat panel display 86 displays various pieces of information regarding a pulsed liquid jet. The display content may be set as appropriate, and, in the present embodiment, the flat panel display 86 includes a main jet energy display portion 861, a repetition frequency display portion 862, and a power display portion 863.

The main jet energy display portion 861 displays the energy E [μJ] of a main jet corresponding to a single pulse.

The repetition frequency display portion 862 displays the repetition frequency $F_p$, that is, a repetition frequency [Hz] of the fundamental drive voltage waveform (the drive voltage waveform L1 of one cycle).

The power display portion 863 displays energy per unit time obtained by multiplying a frequency displayed on the repetition frequency display portion 862 by an energy value displayed on the main jet energy display portion 861, that is, power [mW].

A display form of each display portion may be displayed as appropriate. FIG. 35 exemplifies digital display using numerical values (which are replaced with "X" in the figure), but meter display may be used. A change of the energy E, the repetition frequency, or the like from starting of ejection of a pulsed liquid jet due to a changing operation may be displayed in a graph.

Description of Functional Configuration

Figure 36:
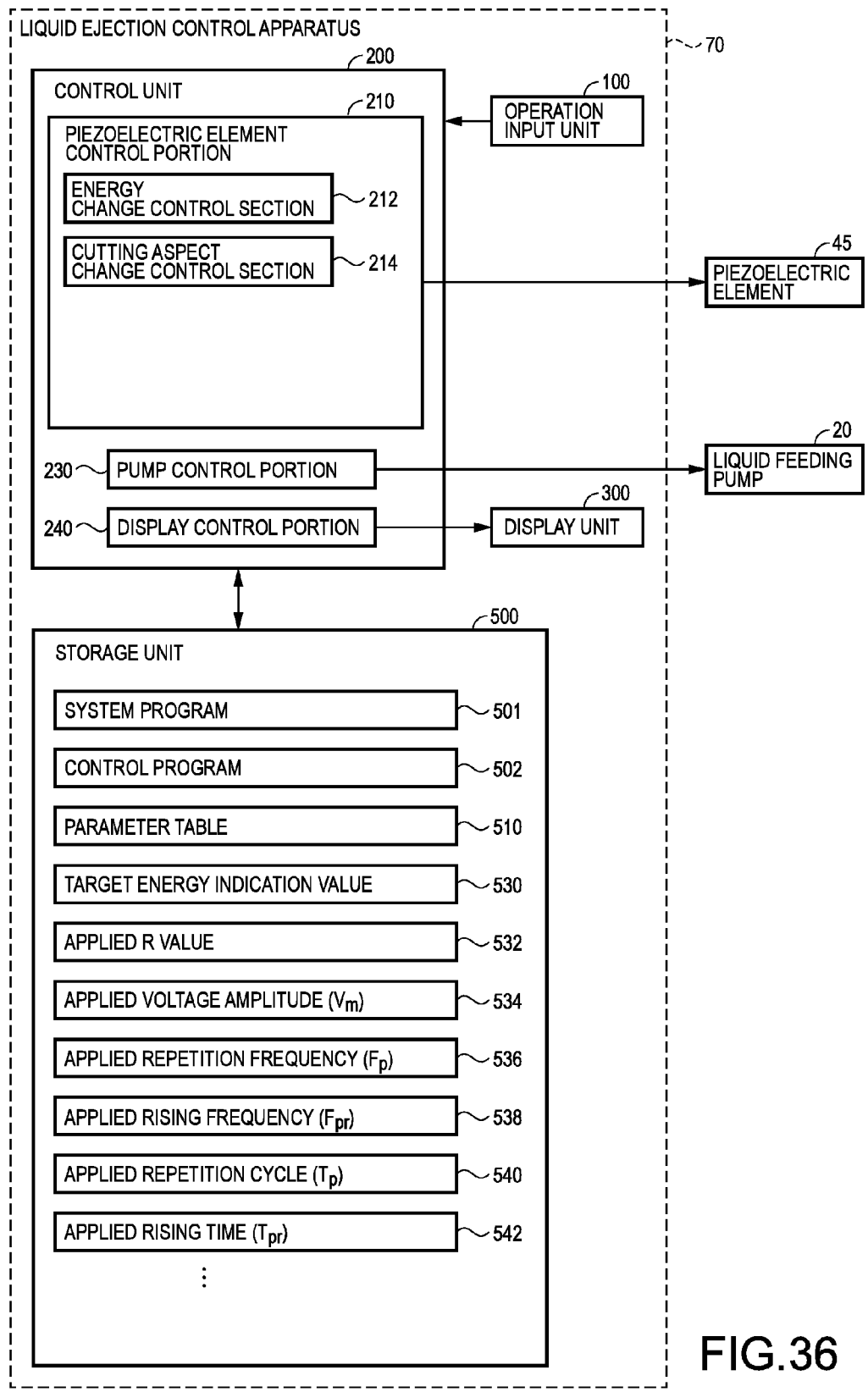
FIG. 36 is a block diagram illustrating a functional configuration example of the liquid ejection control apparatus in the first embodiment.

FIG. 36 is a block diagram illustrating a functional configuration example of the liquid ejection control apparatus in the present embodiment. The liquid ejection control apparatus 70 of the present embodiment includes an operation input unit 100, a display unit 300, a control unit 200, and a storage unit 500.

The operation input unit 100 is implemented by various switches such as a button switch, a lever switch, a dial switch, and a pedal switch, and an input device such as a touch panel, a track pad, and a mouse, and outputs an operation signal corresponding to an input operation to the control unit 200. In the present embodiment, the operation input unit 100 corresponds to the ejection pedal 88 illustrated in FIG. 1, and the main power source switch 81, the pump switch 82, the jet ejection switch 83, and the energy dial 851 and the cutting type dial 858 of the jet setting operation portion 85 illustrated in FIG. 35.

The control unit 200 is implemented by a microprocessor such as a central processing unit (CPU) or a digital signal processor (DSP), and a control device and a calculation device such as an application specific integrated circuit (ASIC), and generally controls the respective portions of the liquid ejection system 1. The control unit 200 of the present embodiment includes a piezoelectric element control portion 210, a pump control portion 230, and a display control portion 240. The respective portions constituting the control unit 200 may be formed of hardware such as a dedicated module circuit.

The piezoelectric element control portion 210 controls driving of the piezoelectric element 45. Specifically, a drive voltage waveform is generated on the basis of the above Equation (18), preferably, the above Equation (19) (as specific examples, Equation (21) or Equation (23)). The piezoelectric element control portion 210 of the present embodiment includes an energy change control section 212 and a cutting aspect change control section 214.

The energy change control section 212 changes the energy E of the main jet 3 corresponding to a single pulse in response to an energy setting operation performed by the user. In the present embodiment, a combination of the repetition frequency $F_p$, the rising frequency $F_p$, and the voltage amplitude $V_m$ correlated with a dial position of the energy dial 851 is determined by referring to a parameter table 510 stored in the storage unit 500. The repetition cycle $T_p$ and the rising time $T_{pr}$ are determined on the basis of the repetition frequency $F_p$ and the rising frequency $F_{pr}$, respectively.

The cutting aspect change control section 214 controls changing of a drive voltage waveform in response to a cutting aspect setting operation performed by the user. In the present embodiment, a value of R (an index value; refer to FIG. 34) corresponding to a dial position of the cutting type dial 858 is applied to the above Equation (18), preferably, Equation (19) (as specific examples, Equation (21) or Equation (23)) by referring to the parameter table 510 stored in the storage unit 500. In other words, a position of an inflection point of a rising portion (a rising portion of the drive voltage waveform) is set according to the index value corresponding to the dial position of the cutting type dial 858, and thus a flow velocity peak timing of the rising portion is set so that the drive voltage waveform is modified.

The pump control portion 230 generates and outputs a drive signal so as to drive the liquid feeding pump 20.

The display control portion 240 performs display control for displaying various pieces of information regarding a pulsed liquid jet on the display unit 300, and generation of display signals. In the present embodiment, the display control portion 240 performs calculation of various pieces of information displayed on the flat panel display 86 illustrated in FIG. 35, and display control.

The display unit 300 is implemented by a display device such as a liquid crystal display (LCD) or an electroluminescent (EL) display, and displays various screens such as a display screen on the basis of display signals input from the control unit 200. In the present embodiment, the flat panel display 86 illustrated in FIG. 35 corresponds to the display unit 300.

The storage unit 500 is implemented by various integrated circuit (IC) memories such as a read only memory (ROM), a flash ROM, or a random access memory (RAM), or a storage medium such as a hard disk. The storage unit 500 stores in advance a program for operating the liquid ejection system 1 and thus realizing various functions of the liquid ejection system 1, data used during execution of the program, and the like. The storage unit 500 is used as a work storage region of the control unit 200 and stores various items of data.

The storage unit 500 of the present embodiment stores a system program 501, a control program 502, the parameter table 510, a target energy indication value 530, an applied R value 532, an applied voltage amplitude 534, an applied repetition frequency 536, an applied rising frequency 538, an applied repetition frequency 540, and an applied rising time 542. Of course, the storage unit 500 may store other data, for example, a clocking timer or counter as appropriate.

The system program 501 is a basic program for causing a computer to function as the liquid ejection control apparatus 70. The control program 502 is a program for causing the control unit 200 to function as the piezoelectric element control portion 210, the pump control portion 230, and the display control portion 240. The control program 502 may be formed as a part of the system program 501. In a case where the functional portions (the piezoelectric element control portion 210, the pump control portion 230, and the display control portion 240) of the control unit 200 are realized by hardware, elements for realizing the functional portions may be omitted from the program.

The parameter table 510 defines values of various control parameters for setting a drive voltage waveform. In the present embodiment, the parameter table 510 defines values of the respective control parameters (the voltage amplitude $V_m$, the repetition frequency $F_p$, and the rising frequency $F_{pr}$) for controlling a drive voltage waveform so that the energy E (flow velocity energy) of the main jet 3 corresponding to a single pulse has an energy indication value 512 corresponding to a dial position of the energy dial 851.

Specifically, for example, as illustrated in FIG. 37, an energy indication value 512 is stored in correlation with an energy dial position 511. Cutting type dial positions 513 (R values; inflection point indication values) of five types, voltage amplitudes 514 of five types, repetition frequencies 516 of five types, and rising frequencies 518 of five types are stored in correlation with each other for each set of the energy dial position 511 and the energy indication value 512.

Combinations of respective values of the voltage amplitudes 514, the repetition frequencies 516, and the rising frequencies 518 may be determined in advance through simulation.

The simulation may be performed on the basis of a model replacing a channel system of the liquid ejection device 30 with fluid (channel) resistance, fluid inertance, fluid compliance, or the like, and various control parameters regarding a drive voltage waveform may be set by using numerical value simulation which uses an equivalent circuit method. Alternatively, if higher accuracy is required, fluid simulation using a finite element method (FEM), a finite volume method (FVM), or the like may be used.

Specifically, the energy E of the main jet 3 corresponding to a single pulse is calculated while changing each of the voltage amplitude $V_m$, the rising frequency $F_{pr}$, and the repetition frequency $F_p$ as various control parameters regarding a drive voltage waveform. If the voltage amplitude $V_m$ and the rising frequency $F_{pr}$ are changed in a state in which the repetition frequency $F_p$ is fixed, contour lines of the energy E of the main jet 3 may be drawn (FIG. 29).

In the present embodiment, the energy indication value 512 in five steps at predetermined intervals is allocated to the energy dial 851, and thus at least five contour lines are set. For example, in FIG. 29, values of intersections with energy indication values (five contour lines) in five steps along the dashed line obliquely drawn from the lower left to the upper right of the graph may be read in a state in which the repetition frequencies 516 is fixed, and may be stored in the voltage amplitudes 514 and the rising frequencies 518 of the parameter table 510.

Of course, a method of selecting values stored in the parameter table 510 is not limited thereto. The voltage amplitudes 514 and the repetition frequencies 516 may be fixed values, and only the rising frequencies 518 may be set for the energy indication value 512. In other words, in FIG. 29, the rising frequency $F_{pr}$ at an intersection between a line (for example, a line segment drawn in parallel to the longitudinal axis from the drive voltage V54) of "$V_m$=fixed" and the contour line may be read.

Similarly, the repetition frequencies 516 and the rising frequencies 518 may be fixed values, and only the voltage amplitudes 514 may be set for the energy indication value 512. None of the voltage amplitudes 514, the repetition frequencies 516, and the rising frequencies 518 may be set to fixed values. In this case, a plurality of graphs as illustrated in FIG. 29 are created with a difference of the repetition frequency $F_p$, and transverse reading is performed on the graphs.

Energy of a jet corresponding to a single pulse may be calculated through simulation by changing four elements such as the voltage amplitude $V_m$, the rising frequency $F_{pr}$, the repetition frequency $F_p$, and an R value as various control parameters regarding a drive voltage waveform. In other words, each value of the parameter table 510 may be determined so that the energy indication value 512 is realized by combinations of the four elements such as an R value of the cutting type dial positions 513, the voltage amplitudes 514, the repetition frequencies 516, and the rising frequencies 518.

Referring to FIG. 36 again, the target energy indication value 530 is a target value of energy realized by a main jet corresponding to a single pulse when a drive voltage waveform is generated. An index value or a set value corresponding to a dial position of the energy dial 851 is stored.

The applied R value 532 is an R value used when a drive voltage waveform is generated on the basis of Equation (18), preferably, Equation (19) (as specific examples, Equation (21) or Equation (23)). In the present embodiment, an R value corresponding to a dial position of the cutting type dial 858, that is, a value indicating an inflection point position is stored.

The applied voltage amplitude 534 is the voltage amplitude $V_m$ used when a drive voltage waveform is generated on the basis of Equation (18), preferably, Equation (19) (as specific examples, Equation (21) or Equation (23)). The applied voltage amplitude 534 is determined by referring to the parameter table 510.

The applied repetition frequency 536 is the repetition frequency $F_p$ used when a drive voltage waveform is generated on the basis of a rising portion expressed by Equation (18), preferably, Equation (19) (as specific examples, Equation (21) or Equation (23)), or a falling portion expressed by Equation (24) or (25). The applied repetition frequency 536 is determined by referring to the parameter table 510.

The applied rising frequency 538 is the rising frequency $F_{pr}$ used when a drive voltage waveform is generated on the basis of Equation (18), preferably, Equation (19). In the present embodiment, the applied rising frequency 538 is determined by referring to the parameter table 510.

The applied repetition frequency 540 is the repetition cycle $T_p$ used when a drive voltage waveform is generated on the basis of a rising portion expressed by Equation (18), preferably, Equation (19) (as specific examples, Equation (21) or Equation (23)), or a falling portion expressed by Equation (24) or (25). The applied repetition frequency 540 is calculated on the basis of the applied repetition frequency 536.

The applied rising time 542 is the rising time $T_{pr}$ used when a drive voltage waveform is generated on the basis of Equation (18), preferably, Equation (19). In the present embodiment, the applied rising time 542 is calculated on the basis of the applied rising frequency 538.

Description of Operation

Figure 38:
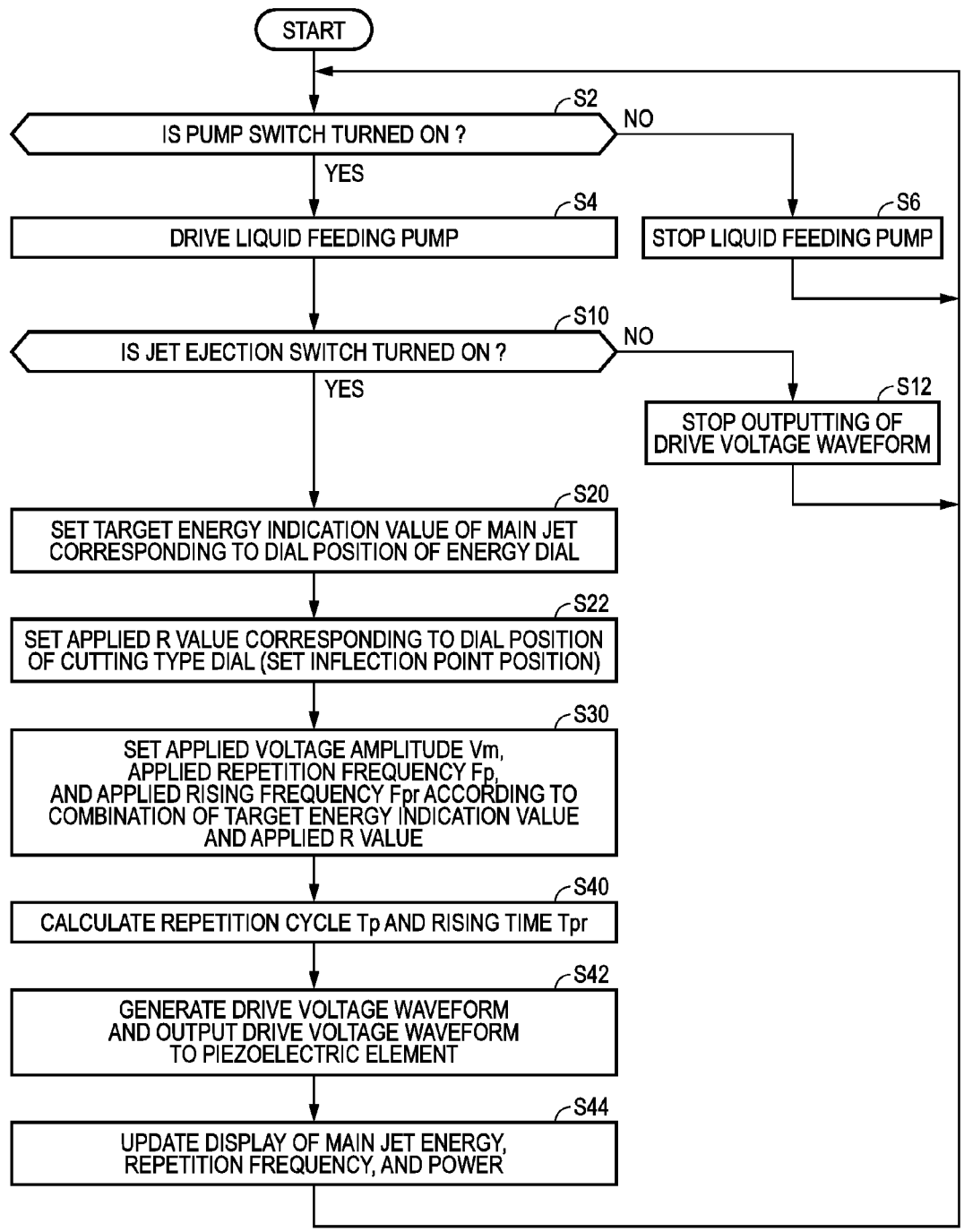
FIG. 38 is a flowchart illustrating a flow of a process performed by a control unit in the first embodiment.

FIG. 38 is a flowchart illustrating a flow of a process performed by the control unit 200 of the present embodiment, and the process is performed by the control unit 200 executing the control program 502.

If the pump switch 82 of the operation panel 80 is turned on (YES in step S2; refer to FIG. 35), the control unit 200 drives the liquid feeding pump 20 (step S4). If the pump switch 82 is turned off (NO in step S2), the liquid feeding pump 20 is stopped (step S6).

If the jet ejection switch 83 is turned off (NO in step S10), the control unit 200 does not output a drive voltage waveform to the piezoelectric element 45 (refer to FIG. 2) although the pump switch 82 of the operation panel 80 is turned on (step S12).

If the pump switch 82 of the operation panel 80 is turned on, and the jet ejection switch 83 is turned on (YES in step S10), the control unit 200 reads the energy indication value 512 corresponding to the present dial position of the energy dial 851 from the parameter table 510 (refer to FIG. 27), and sets the value as the target energy indication value 530 (step S20; refer to FIG. 36).

Next, the control unit 200 reads any one of the cutting type dial positions 513 corresponding to the energy indication value 512 conforming to the target energy indication value 530 from the parameter table 510 according to the present dial position of the cutting type dial 858, and sets the applied R value 532 (step S22). That is, an inflection point position in a rising portion is set. In other words, a flow velocity peak timing of the main jet 3 is set.

The control unit 200 reads the voltage amplitudes 514, the repetition frequencies 516, and the rising frequencies 518 corresponding to a combination of the target energy indication value 530 and the applied R value 532 from the parameter table 510, and sets the values as the applied voltage amplitudes 534, the applied repetition frequencies 536, and the applied rising frequencies 538, respectively (step S30). The control unit 200 derives the applied repetition frequency 540 from the applied repetition frequency 536, and derives the applied rising time 542 from the applied rising frequency 538 (step S40).

Consequently, all the variables in Equation (18), preferably, Equation (19) (as specific examples, Equation (21) or Equation (23)) are prepared, and thus the control unit 200 calculates the drive voltage $V_p$ on the basis of Equation (18), preferably, Equation (19) (as specific examples, Equation (21) or Equation (23)), and outputs a drive signal having the drive voltage $V_p$ to the piezoelectric element 45 (step S42). The control unit 200 calculates a value of energy and a value of power (energy per unit time) of a main jet, and updates each item of display content of the flat panel display 86 (step S44; refer to FIG. 35).

As described above, according to the first embodiment, it is possible to provide a technique of controlling ejection of a pulsed liquid jet, capable of flexibly coping with needs for a fine cutting aspect in various use cases. It is possible to adjust a relationship between a cut depth and a cut area without changing a cut volume.

Second Embodiment

Next, a description will be made of a second embodiment to which the invention is applied.

The present embodiment is fundamentally realized in the same manner as the first embodiment, but is different in that a user can change the repetition frequency $F_p$. Hereinafter, differences from the first embodiment will be mainly described, the same constituent elements as those in the first embodiment are given the same reference numerals, and repeated description will be omitted.

Figure 39:
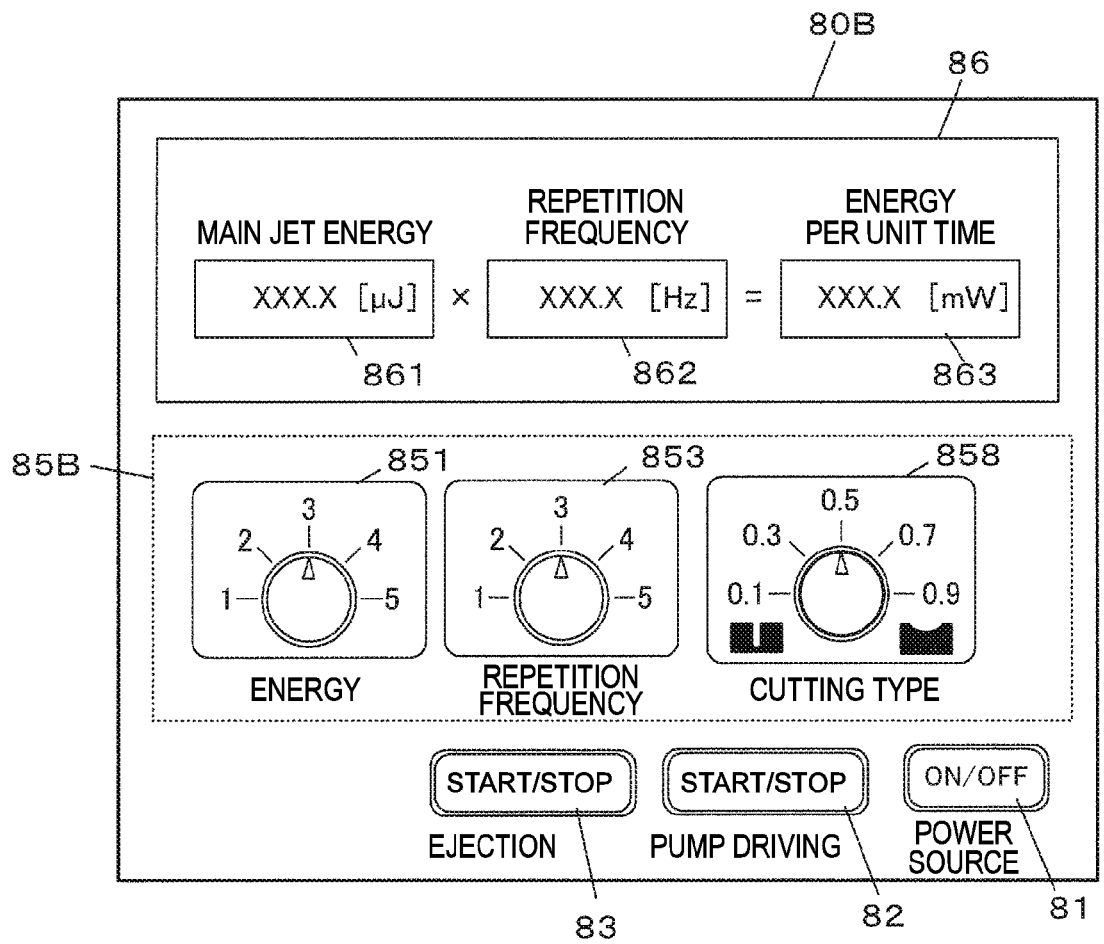
FIG. 39 is a diagram illustrating a configuration example of an operation panel of a liquid ejection control apparatus in a second embodiment.

FIG. 39 is a diagram illustrating a configuration example of an operation panel 80B in the present embodiment. The operation panel 80B is fundamentally the same as that in the first embodiment, but a jet setting operation portion 85B of the present embodiment includes a repetition frequency dial 853 for setting the repetition frequency $F_p$.

The repetition frequency dial 853 receives an operation of setting the repetition frequency $F_p$. In the present embodiment, the repetition frequency dial 853 is formed of dials with scales in five steps such as "1" to "5", the respective scales are correlated with frequencies at the same intervals, and the applied repetition frequency 536 is determined in accordance with a dial position of the repetition frequency dial 853. Scales of the repetition frequency dial 853 may be set as appropriate. For example, the repetition frequency $F_p$ may be configured to be set steplessly.

Figure 40:
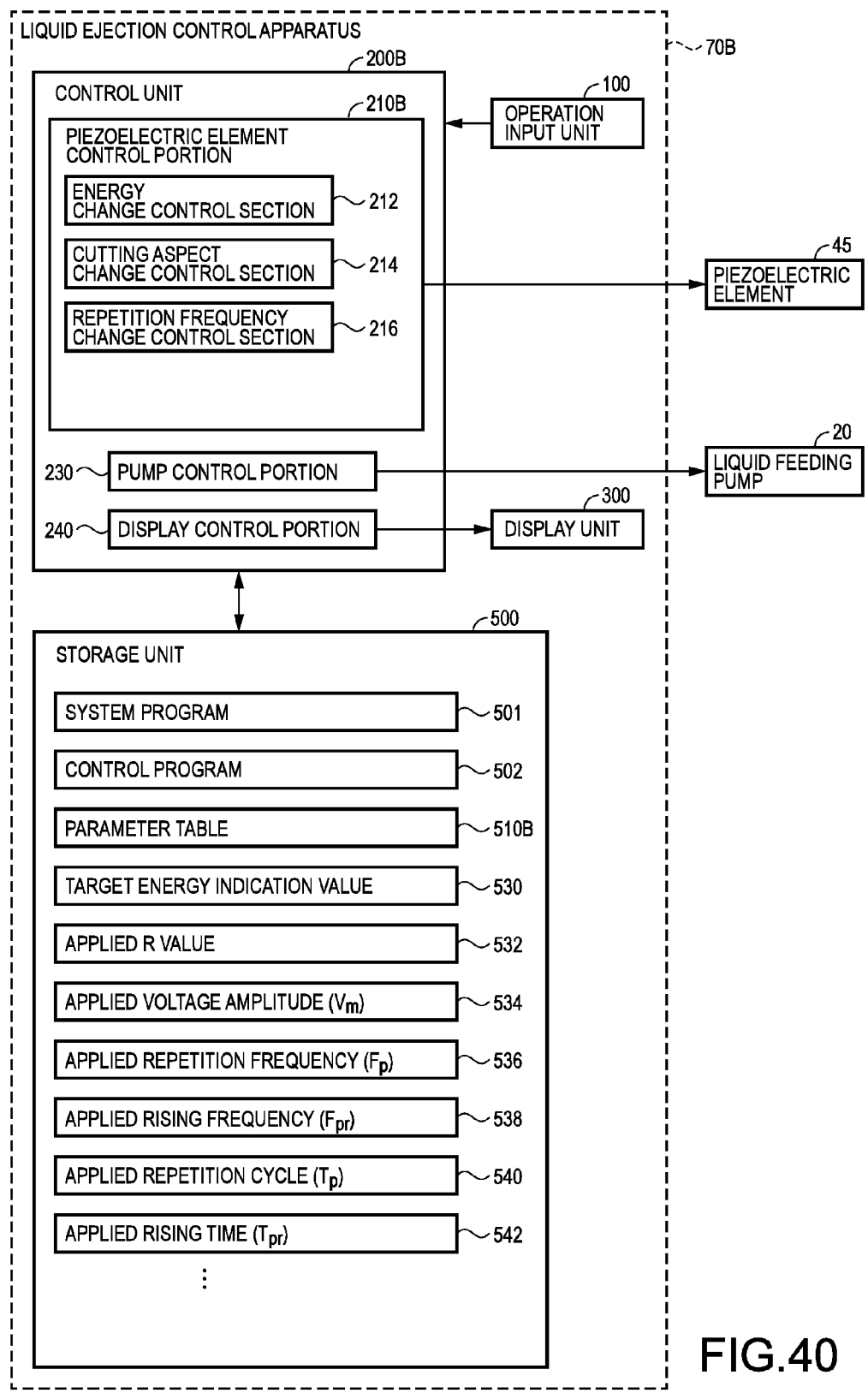
FIG. 40 is a block diagram illustrating a functional configuration example of the liquid ejection control apparatus in the second embodiment.

FIG. 40 is a block diagram illustrating a functional configuration example of a liquid ejection control apparatus 70B in the present embodiment. The liquid ejection control apparatus 70B fundamentally has the same functional configuration as that of the liquid ejection control apparatus 70 of the first embodiment, but, in a control unit 200B of the present embodiment, a piezoelectric element control portion 210B includes a repetition frequency change control section 216.

The repetition frequency change control section 216 controls changing of the repetition frequency $F_p$ used to generate a drive voltage waveform according to an operation of setting a repetition frequency. In the present embodiment, a value correlated with each dial position of the repetition frequency dial 853 in advance is set as the applied repetition frequency 536 by referring to a parameter table 510B.

FIG. 41 is a diagram illustrating a data configuration example of the parameter table 510B of the present embodiment. In the parameter table 510B, cutting type dial positions 513 of five types are correlated with each combination of two elements such as an energy dial position 511 (energy indication value 512) and a repetition frequency dial position 515 (repetition frequencies 516B). The repetition frequencies 516B are fixed values which are correlated with the respective dial positions of the repetition frequency dial 853 in advance.

The voltage amplitudes 514 and the rising frequencies 518 are stored in correlation with each combination of three elements such as the energy dial position 511 (energy indication value 512), the repetition frequency dial position 515 (repetition frequencies 516B), and the cutting type dial positions 513.

The voltage amplitudes 514 and the rising frequencies 518 of the present embodiment are set so as to realize corresponding energy indication values 512 through combination with corresponding repetition frequencies 516B. Specifically, a graph as illustrated in FIG. 29 is prepared for each repetition frequency, and voltage amplitudes and rising frequencies may be read on the basis of intersections with contour lines of the energy indication value 512 so as to be set.

Alternatively, the voltage amplitudes 514 and the rising frequencies 518 of the present embodiment may be set through simulation so that corresponding energy indication values 512 are realized through combination with two elements such as corresponding repetition frequencies 516B and R values indicated by the cutting type dial positions 513.

Figure 42:
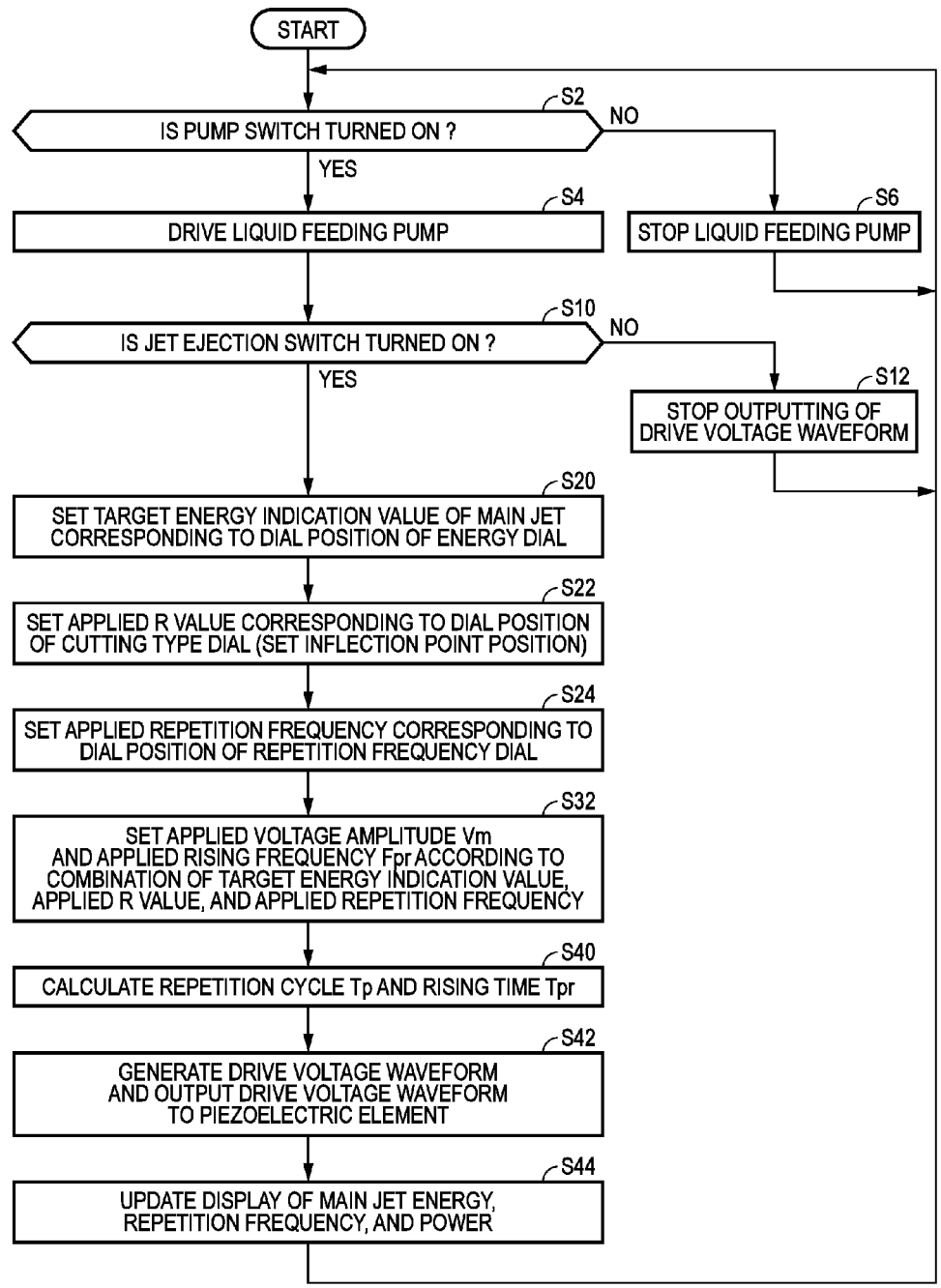
FIG. 42 is a flowchart illustrating a flow of a process performed by a control unit in the second embodiment.

FIG. 42 is a flowchart illustrating a flow of a process performed by the control unit 200B of the present embodiment. The flow of the process in the present embodiment is fundamentally the same as the flow of the process in the first embodiment, but step S24 is added, and step S32 is executed instead of step S30.

In other words, after step S22, the control unit 200B reads the repetition frequency 516B corresponding to the present dial position of the repetition frequency dial 853 by referring to the parameter table 510B, and sets the applied repetition frequency 536 (refer to FIG. 40) (step S24).

The control unit 200B reads the voltage amplitudes 514 and the rising frequencies 518 corresponding to a combination of the target energy indication value 530, the applied R value 532, and the applied repetition frequency 536 by referring to the parameter table 510B, and sets the values as the applied voltage amplitudes 534 and the applied rising frequencies 538 (step S32).

As described above, according to the present embodiment, it is possible to achieve the same effect as in the first embodiment. In addition, it is possible for a user to change a repetition frequency during use.

Third Embodiment

Next, a description will be made of a third embodiment to which the invention is applied.

The present embodiment is fundamentally realized in the same manner as the second embodiment, but is different in that a user can change the rising frequency $F_{pr}$. Hereinafter, differences from the first and second embodiments will be mainly described, the same constituent elements as those in the second embodiment are given the same reference numerals, and repeated description will be omitted.

Figure 43:
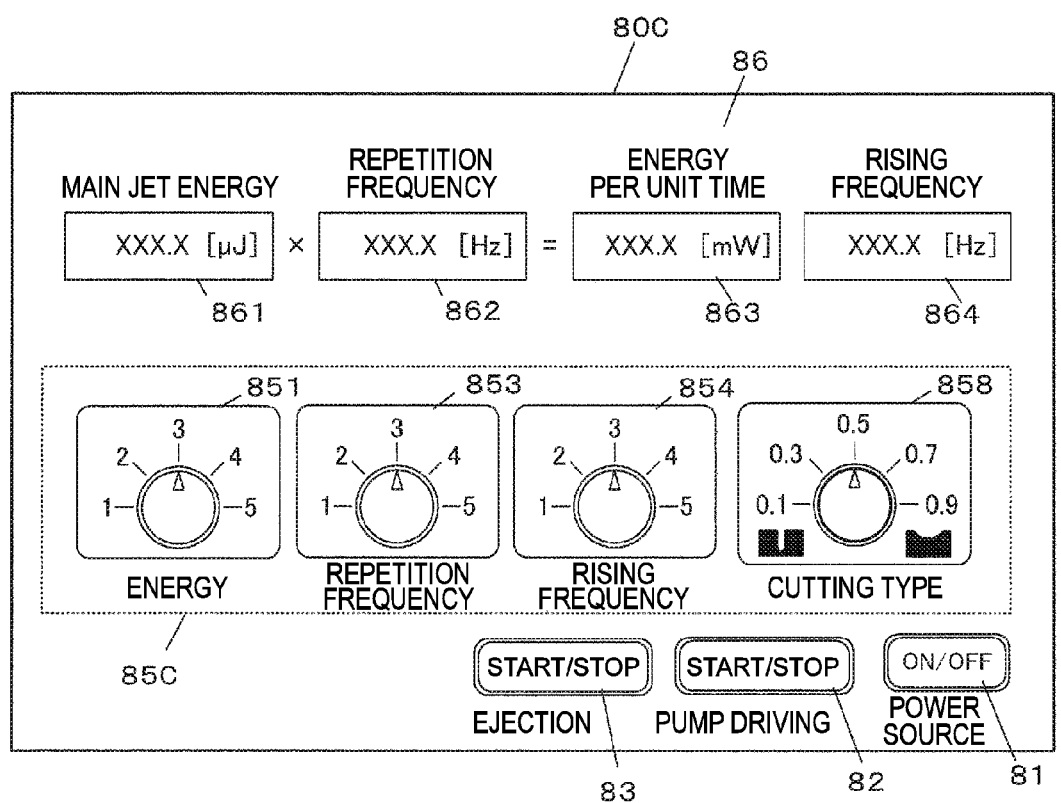
FIG. 43 is a diagram illustrating a configuration example of an operation panel of a liquid ejection control apparatus in a third embodiment.

FIG. 43 is a diagram illustrating a configuration example of an operation panel 80C in the present embodiment. The operation panel 80C is fundamentally the same as that in the second embodiment, but a jet setting operation portion 85C of the present embodiment includes a rising frequency dial 854 for setting the rising frequency $F_{pr}$, and a rising frequency display portion 864 is further displayed on the flat panel display 86.

The rising frequency dial 854 receives an operation of setting the rising frequency $F_{pr}$. In the present embodiment, the rising frequency dial 854 is formed of dials with scales in five steps such as "1" to "5", the respective scales are correlated with frequencies at the same intervals, and the applied rising frequency 538 is determined in accordance with a dial position of the rising frequency dial 854. Scales of the rising frequency dial 854 may be set as appropriate. For example, the rising frequency $F_{pr}$ may be configured to be set steplessly.

Figure 44:
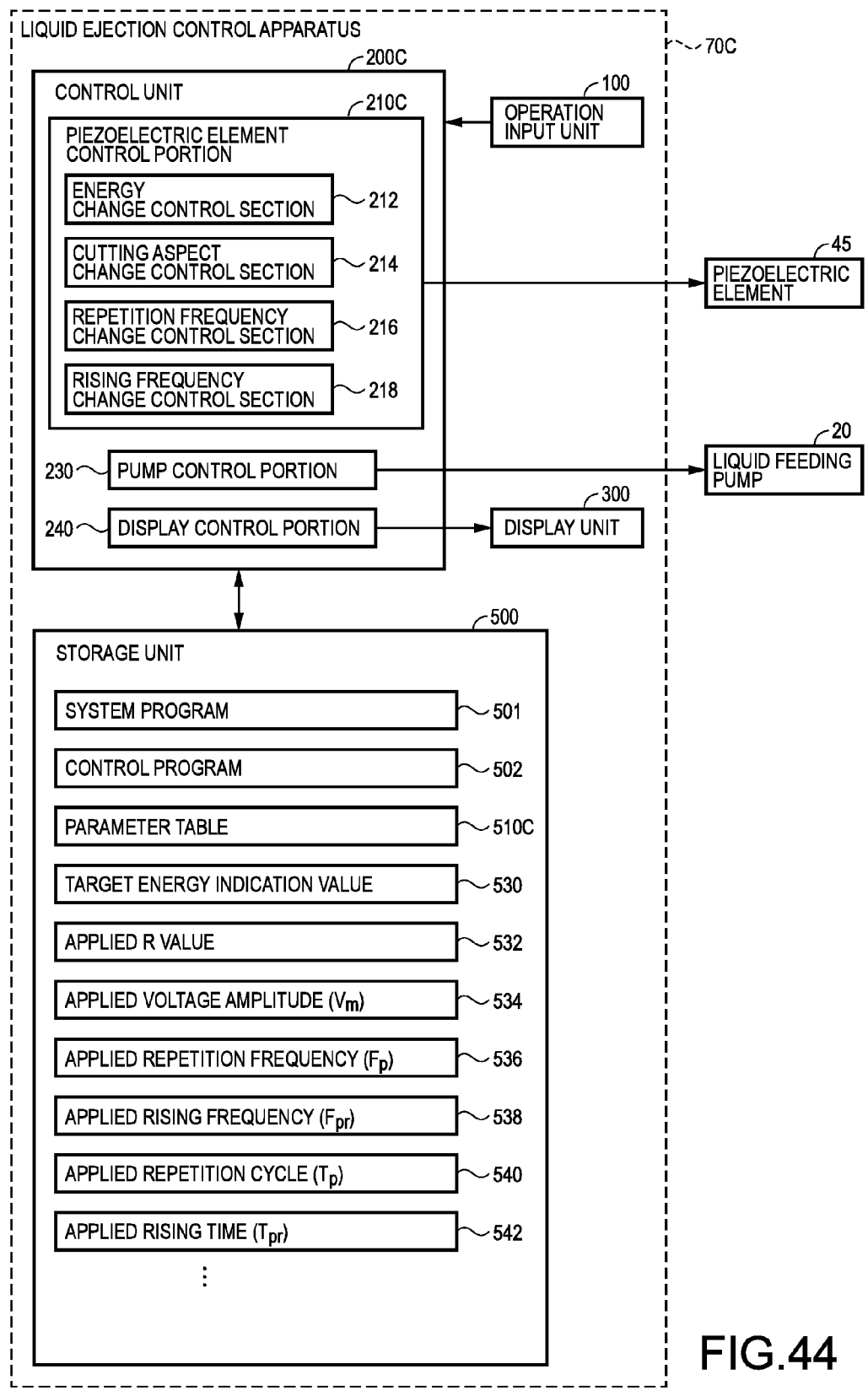
FIG. 44 is a block diagram illustrating a functional configuration example of the liquid ejection control apparatus in the third embodiment.

FIG. 44 is a block diagram illustrating a functional configuration example of a liquid ejection control apparatus 70C in the present embodiment.

The liquid ejection control apparatus 70C fundamentally has the same functional configuration as that of the liquid ejection control apparatus 70B of the second embodiment, but a piezoelectric element control portion 210C of a control unit 200C of the present embodiment includes a rising frequency change control section 218.

The rising frequency change control section 218 controls changing of the rising frequency $F_{pr}$ used to generate a drive voltage waveform according to an operation of setting a rising frequency. In the present embodiment, a value correlated with each dial position of the rising frequency dial 854 in advance is set as the applied rising frequency 538 by referring to a parameter table 510C.

The display control portion 240 of the present embodiment may display the rising frequency display portion 864 on the flat panel display 86.

FIG. 45 is a diagram illustrating a data configuration example of the parameter table 510C of the present embodiment. The parameter table 510C is fundamentally the same as that in the second embodiment, but rising frequency dial positions 517 of five types and rising frequencies 518C of five types are correlated with each combination of an energy dial position 511 (energy indication value 512) and a repetition frequency dial position 515 (repetition frequency 516B). The rising frequencies 518C are fixed values which are correlated with the respective dial positions of the rising frequency dial 854 in advance.

The cutting type dial positions 513 and the voltage amplitudes 514 are stored in correlation with each combination of three elements such as the energy dial position 511 (energy indication value 512), the repetition frequency dial position 515 (repetition frequencies 516B), and the rising frequency dial positions 517 (rising frequencies 518).

The voltage amplitudes 514 of the present embodiment are set so as to realize corresponding energy indication values 512 through combination with two elements such as corresponding repetition frequencies 516B and rising frequencies 518C. The voltage amplitudes 514 may be set in advance on the basis of simulation results.

Alternatively, the voltage amplitudes 514 of the present embodiment may be set through simulation so that corresponding energy indication values 512 are realized through combination with three elements such as corresponding repetition frequencies 516B and rising frequencies 518C, and R values indicated by the cutting type dial positions 513.

In other words, the control unit 200C reads the repetition frequency 516B corresponding to the present dial position of the repetition frequency dial 853 by referring to the parameter table 510C, and sets the applied repetition frequency 536 (refer to FIG. 44).

The display control portion 240 of the present embodiment may display the rising frequency display portion 864 on the flat panel display 86.

Figure 46:
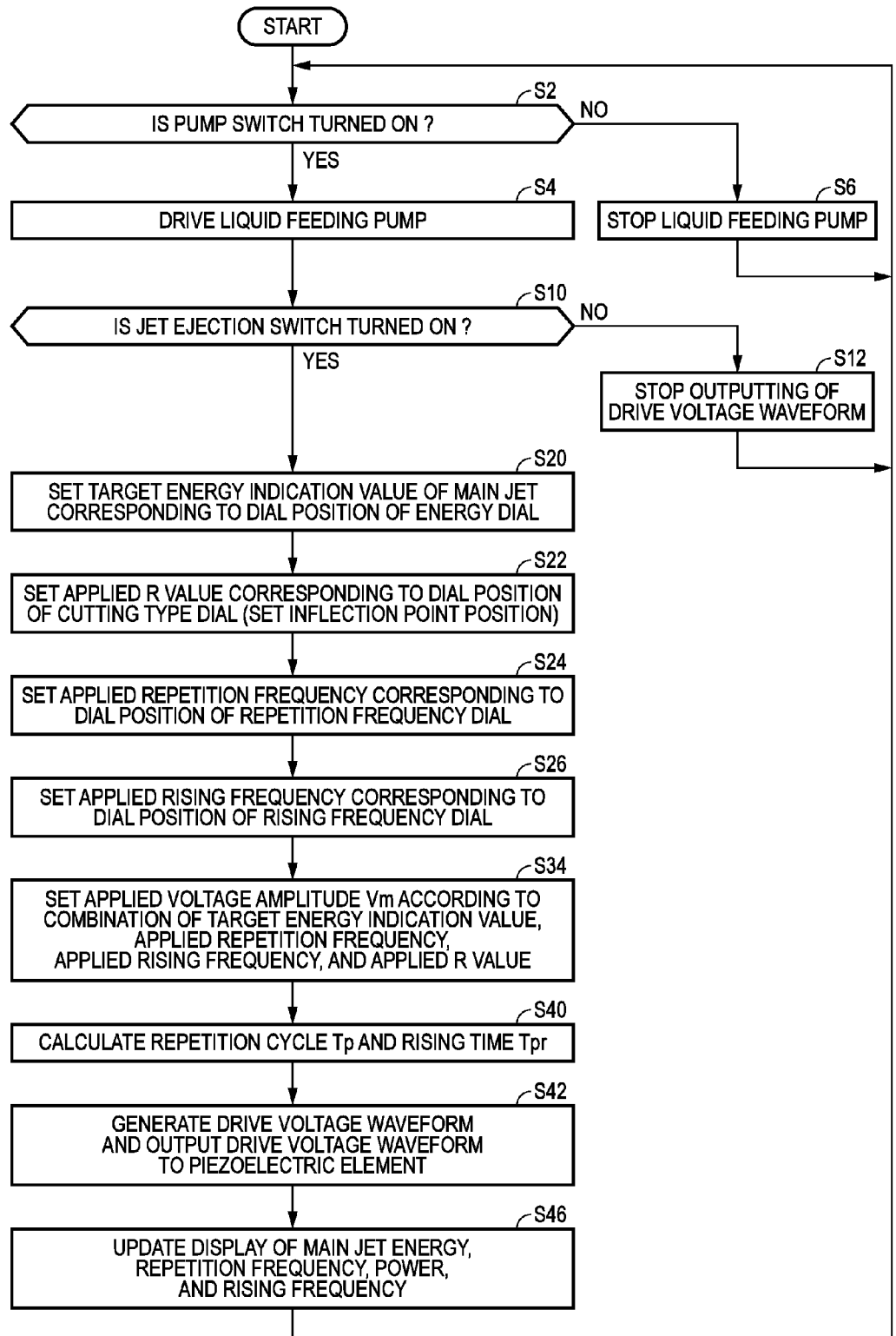
FIG. 46 is a flowchart illustrating a flow of a process performed by a control unit in the third embodiment.

FIG. 46 is a flowchart illustrating a flow of a process performed by the control unit 200C of the present embodiment. The flow of the process in the present embodiment is fundamentally the same as the flow of the process in the second embodiment, but step S26 is added, step S34 is executed instead of step S32, and step S46 is executed instead of step S44.

In other words, after step S24, the control unit 200C reads the rising frequency 518C corresponding to the present dial position of the rising frequency dial 854 by referring to the parameter table 510C, and sets the applied rising frequency 538 (step S26).

The control unit 200C searches the parameter table 510C for the cutting type dial positions 513 conforming to the applied rising frequency 538 in a combination of the energy indication value 512 conforming to the target energy indication value 530, the repetition frequency 516B conforming to the applied repetition frequency 536, and the rising frequency 518 conforming to the applied rising frequency 538. The voltage amplitudes 514 correlated with the cutting type dial positions 513 are read, and are set as the applied voltage amplitudes 534 (step S34).

After step S42, the control unit 200C updates display of the main jet energy display portion 861, the repetition frequency display portion 862, the power display portion 863, and the rising frequency display portion 864 of the flat panel display 86 (refer to FIG. 43) (step S46).

As described above, according to the present embodiment, it is possible to achieve the same effect as in the second embodiment. In addition, it is possible for a user to change the rising frequency $F_{pr}$.

Fourth Embodiment

Next, a description will be made of a fourth embodiment to which the invention is applied.

The present embodiment is fundamentally realized in the same manner as the third embodiment. Hereinafter, differences from the third embodiment will be mainly described, the same constituent elements as those in the first to third embodiments are given the same reference numerals, and repeated description will be omitted.

Figure 47:
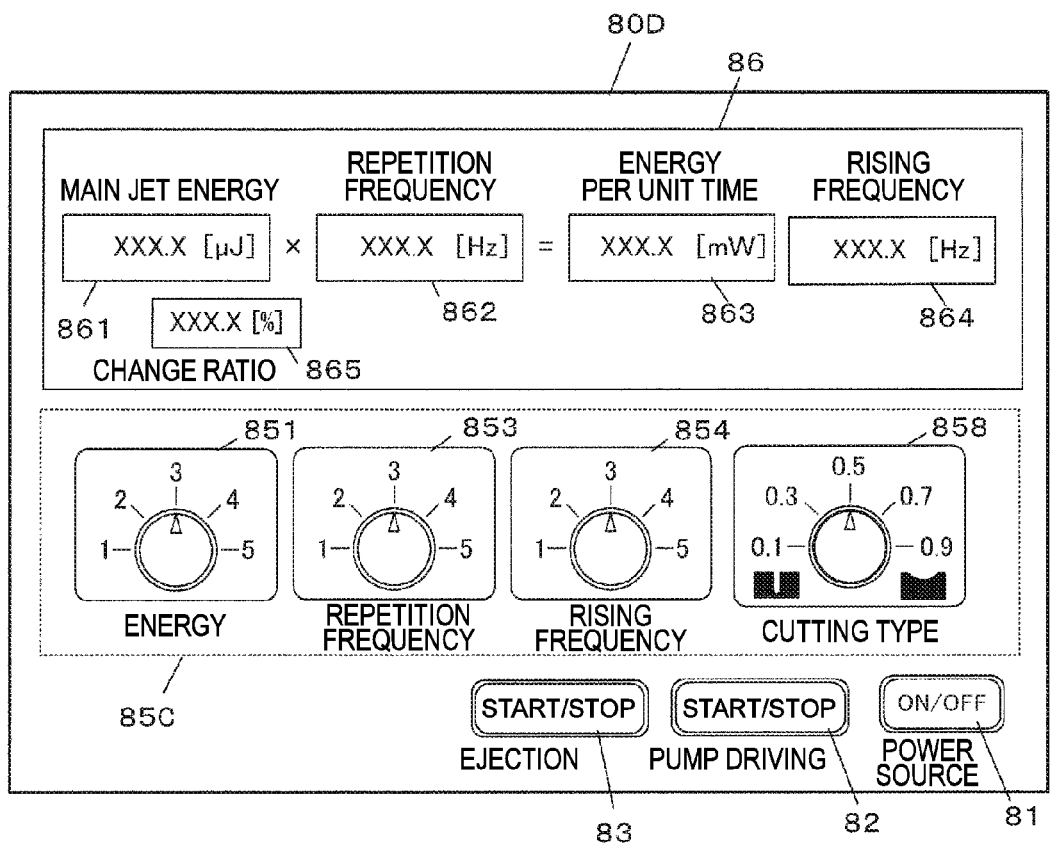
FIG. 47 is a diagram illustrating a configuration example of an operation panel of a liquid ejection control apparatus in a fourth embodiment.

FIG. 47 is a diagram illustrating a configuration example of an operation panel 80D in the present embodiment. The operation panel 80D is fundamentally the same as that in the third embodiment, but an energy change ratio display portion 865 is displayed on the flat panel display 86.

The energy change ratio display portion 865 displays a change ratio of the energy E of the main jet 3 in a case where an R value is changed from a predetermined reference value (a reference position of an inflection point of a rising portion) in a state in which set values of energy, a repetition frequency, and a rising frequency are fixed.

Figure 48:
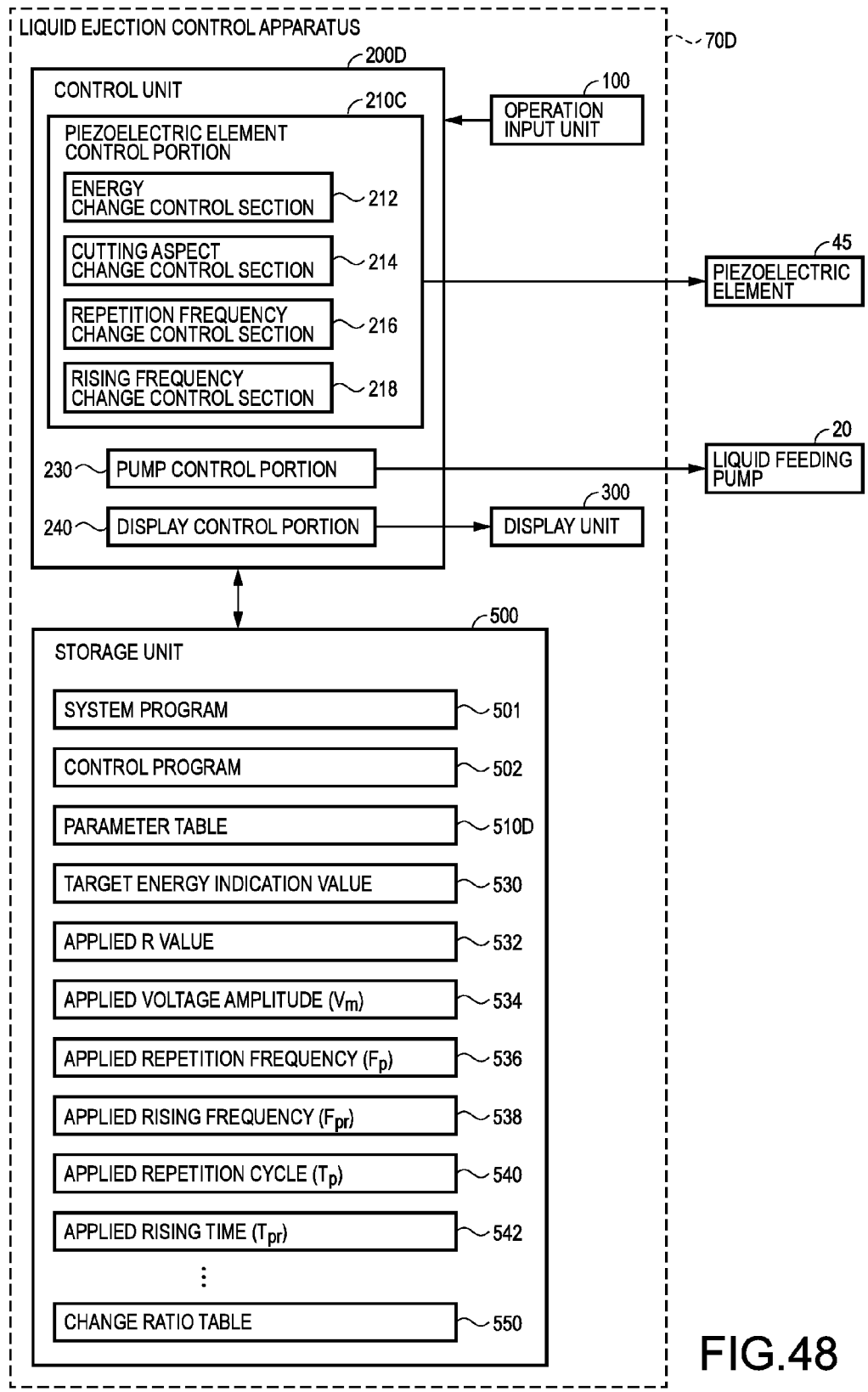
FIG. 48 is a block diagram illustrating a functional configuration example of the liquid ejection control apparatus in the fourth embodiment.

FIG. 48 is a block diagram illustrating a functional configuration example of a liquid ejection control apparatus 70D in the present embodiment. The liquid ejection control apparatus 70D fundamentally has the same functional configuration as that of the liquid ejection control apparatus 70C of the third embodiment, but the display control portion 240 of the present embodiment may control display of the energy change ratio display portion 865. The storage unit 500 of the present embodiment stores a parameter table 510D and a change ratio table 550.

FIG. 49 is a diagram illustrating a data configuration example of the parameter table 510D of the present embodiment. The parameter table 510D is fundamentally the same as the parameter table 510C in the third embodiment, but does not include the cutting type dial positions 513. In other words, values of the control parameters (the repetition frequency $F_p$, the rising frequency $F_{pr}$, and the voltage amplitude $V_m$) of a drive voltage waveform of the present embodiment are determined without being influenced by changes of R values (inflection point positions) based on the cutting type dial positions 513.

The change ratio table 550 stores an energy change ratio obtained through simulation in advance. For example, as illustrated in FIG. 50, cutting type dial positions 554 (similar to the cutting type dial positions 513) of five types, main jet energies 556 of five types, and energy change ratios 557 of five types are stored for each combination of three elements such as a repetition frequency 551, a rising frequency 552, and a voltage amplitude 553.

The main jet energies 556 are values of energy of the main jet 3, determined on the basis of four elements such as corresponding repetition frequency 551, rising frequency 552 and voltage amplitude 553, and R values of the cutting type dial positions 554. The main jet energies 556 may be obtained in advance through simulation.

The energy change ratios 557 are ratios obtained when compared with the main jet energy 556 at R=0.5 without changing combinations of four elements such as the repetition frequency 551, the rising frequency 552, the voltage amplitude 553, and R values of the cutting type dial positions 554. R is changed by changing the cutting type dial positions 554. R=0.5 is used as a reference, but other R values may be used as references.

Figure 51:
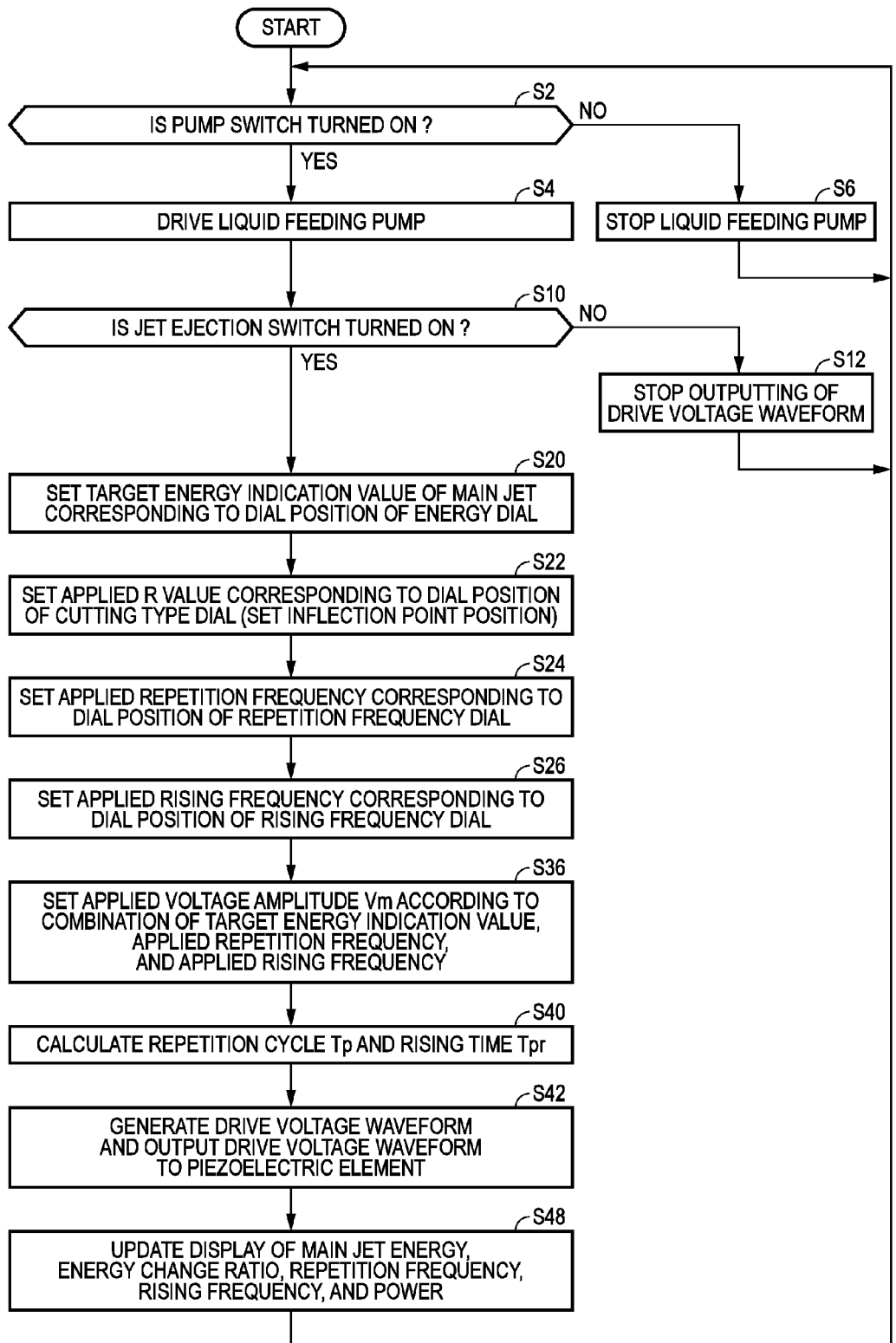
FIG. 51 is a flowchart illustrating a flow of a process performed by a control unit in the fourth embodiment.

FIG. 51 is a flowchart illustrating a flow of a process performed by the control unit 200D of the present embodiment. The flow of the process in the present embodiment is fundamentally the same as the flow of the process in the third embodiment, but step S36 is executed instead of step S34, and step S48 is executed instead of step S46.

In other words, after step S26, the control unit 200D reads, from the parameter table 510D, the voltage amplitudes 514 correlated with a combination of three elements such as the energy indication value 512 conforming to the target energy indication value 530, the repetition frequency 516B conforming to the applied repetition frequency 536, and the rising frequency 518 conforming to the applied rising frequency 538, and sets the applied voltage amplitudes 534 (step S36).

After step S42, the control unit 200D updates display of the main jet energy display portion 861, the repetition frequency display portion 862, the power display portion 863, and the rising frequency display portion 864 of the flat panel display 86. The control unit 200D refers to the change ratio table 550, reads the energy change ratios 557 correlated with a combination of three elements such as the repetition frequency 551 conforming to the applied repetition frequency 536, the rising frequency 552 conforming to the applied rising frequency 538, and the voltage amplitude 553 conforming to the applied voltage amplitude 534, and updates display of the energy change ratio display portion 865 (step S48).

As described above, according to the present embodiment, even in a configuration in which a cutting aspect (R value; inflection point position) is changed after control parameters of a drive voltage waveform are determined and fixed, it is possible to achieve the same effect as in the third embodiment. In this case, it is possible to notify a user how much main jet energy is changed due to changing of a cutting aspect.

Fifth Embodiment

Next, a description will be made of a fifth embodiment to which the invention is applied.

The present embodiment is fundamentally realized in the same manner as the first embodiment. However, the first embodiment focuses on holding of the energy E of the main jet 3 in order not to change a cutting amount when setting values of the control parameters (the repetition frequency $F_p$, the rising frequency $F_{pr}$, and the voltage amplitude $V_m$) of a drive voltage waveform, but the present embodiment is different therefrom in that determination is performed focusing on the momentum P of the main jet 3. Hereinafter, differences from the first embodiment will be mainly described, the same constituent elements as those in the first embodiment are given the same reference numerals, and repeated description will be omitted.

Figure 52:
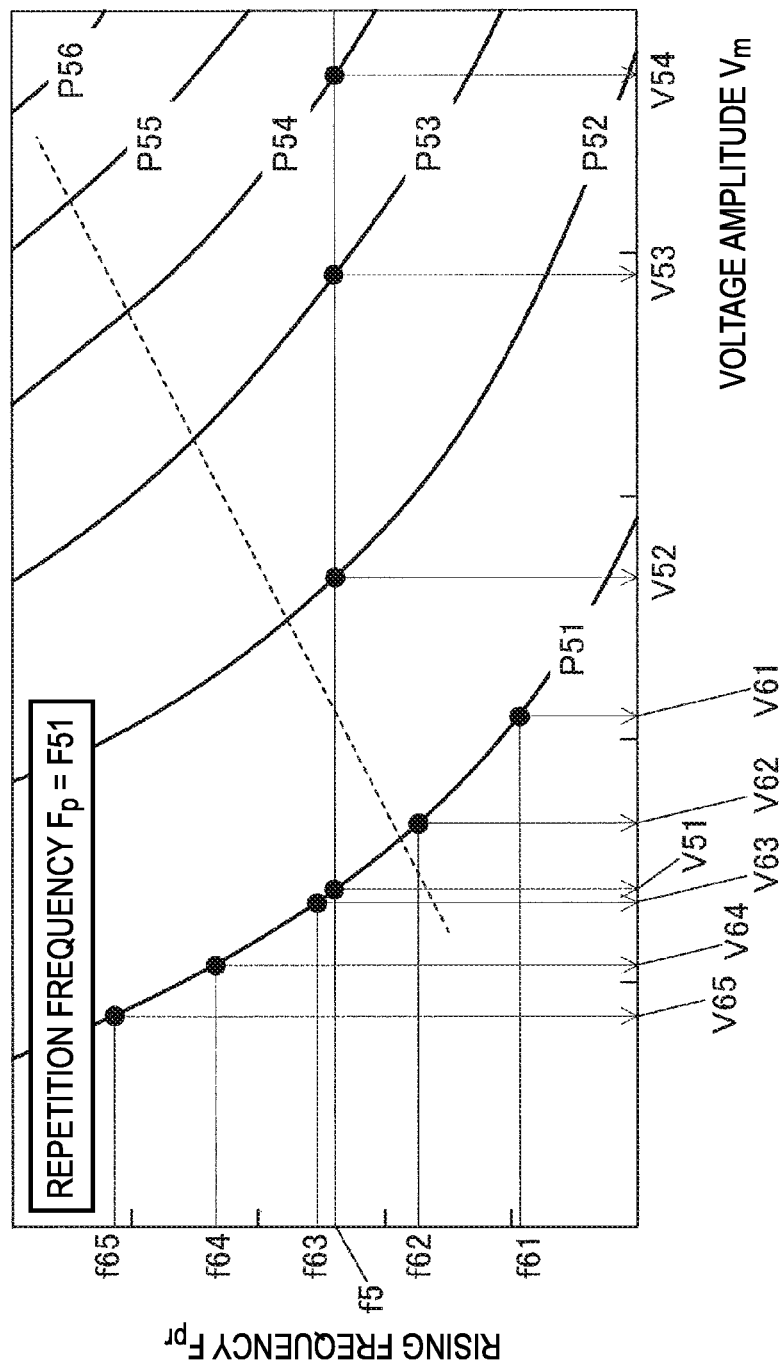
FIG. 52 is a diagram illustrating a relationship among voltage amplitude, a rising frequency, and momentum in a case where a repetition frequency is fixed.

FIG. 52 is a graph corresponding to FIG. 29 of the first embodiment, and is a diagram illustrating a simulation result of a correspondence relationship among the momentum P of the main jet 3 obtained at a predetermined repetition frequency (for example, "F51"), the rising frequency $F_{pr}$, and the voltage amplitude $V_m$.

In other words, for each repetition frequency $F_p$ while changing the repetition frequency $F_p$ in the way described with reference to FIGS. 27 and 28, simulation is performed in a case where the voltage amplitude $V_m$ is fixed and the rising frequency $F_{pr}$ is changed in the way described with reference to FIGS. 23 and 24 and simulation is performed in a case where the rising frequency $F_{pr}$ is fixed and the voltage amplitude $V_m$ is changed in the way described with reference to FIGS. 25 and 26. The momentum P of the main jet 3 obtained through each simulation is obtained.

FIG. 52 is obtained by drawing contour lines regarding the momentum P in a coordinate space in which a longitudinal axis expresses the rising frequency $F_{pr}$, and a transverse axis expresses the voltage amplitude $V_m$. Momentums P51, P52, . . . of the respective contour lines are low on the lower left side, and increase by a predetermined amount toward the upper right side. Although not illustrated, if contour lines are drawn by plotting the momentum P obtained at the same repetition frequency $F_p$ in the same coordinate space, a contour map corresponding to correspondence relationships among the momentum P at the repetition frequency $F_p$, the rising frequency $F_{pr}$, and the voltage amplitude $V_m$ is obtained.

Here, it is noted that the momentum P does not linearly change for the parameter in each coordinate axis direction.

For example, in the correspondence relationships among the momentum P, the rising frequency $F_{pr}$, and the voltage amplitude $V_m$, a case is assumed that the rising frequency $F_{pr}$ is fixed (to f5, for example), the drive voltage waveform of the piezoelectric element 45 is controlled by changing the voltage amplitude $V_m$.

If an amount of to the momentum P to be changed is to be constant in order not to change a cut volume if at all possible, a voltage amplitude change between the voltage amplitudes V51 and V52 is necessary between the momentums P51 and P52, and a voltage amplitude change between the voltage amplitudes V52 and V53 is necessary between the momentum P52 and P53. However, a voltage amplitude gap between the voltage amplitudes V51 and V52 is different from a voltage amplitude gap between the voltage amplitudes V52 and V53. This phenomenon notably appears as the momentum P increases.

Therefore, even if the voltage amplitude $V_m$ is controlled to be changed by a predetermined amount in a state in which the rising frequency $F_{pr}$ is fixed in order not to change a cut volume, a situation in which the momentum P changes may occur. This may also be same for a case where an operation of changing the rising frequency $F_{pr}$ by a predetermined amount in a state in which the voltage amplitude $V_m$ is fixed.

Therefore, in the present embodiment, at least an operation of setting the momentum P is received as an operation performed by a user, and correspondence relationships among the momentum P, the rising frequency $F_{pr}$, and the voltage amplitude $V_m$ for each repetition frequency $F_p$ are prepared in advance as table data on the basis of the contour map obtained for each repetition frequency $F_p$.

Combinations of values of the respective control parameters (the repetition frequency $F_p$, the rising frequency $F_{pr}$, and the voltage amplitude $V_m$) for realizing the momentum P set by the user are determined, and thus driving of the piezoelectric element 45 is controlled. Consequently, adjustment of a cutting aspect from a "narrow and deep" aspect to a "wide and shallow" aspect is realized without changing a cut volume.

Figure 53:
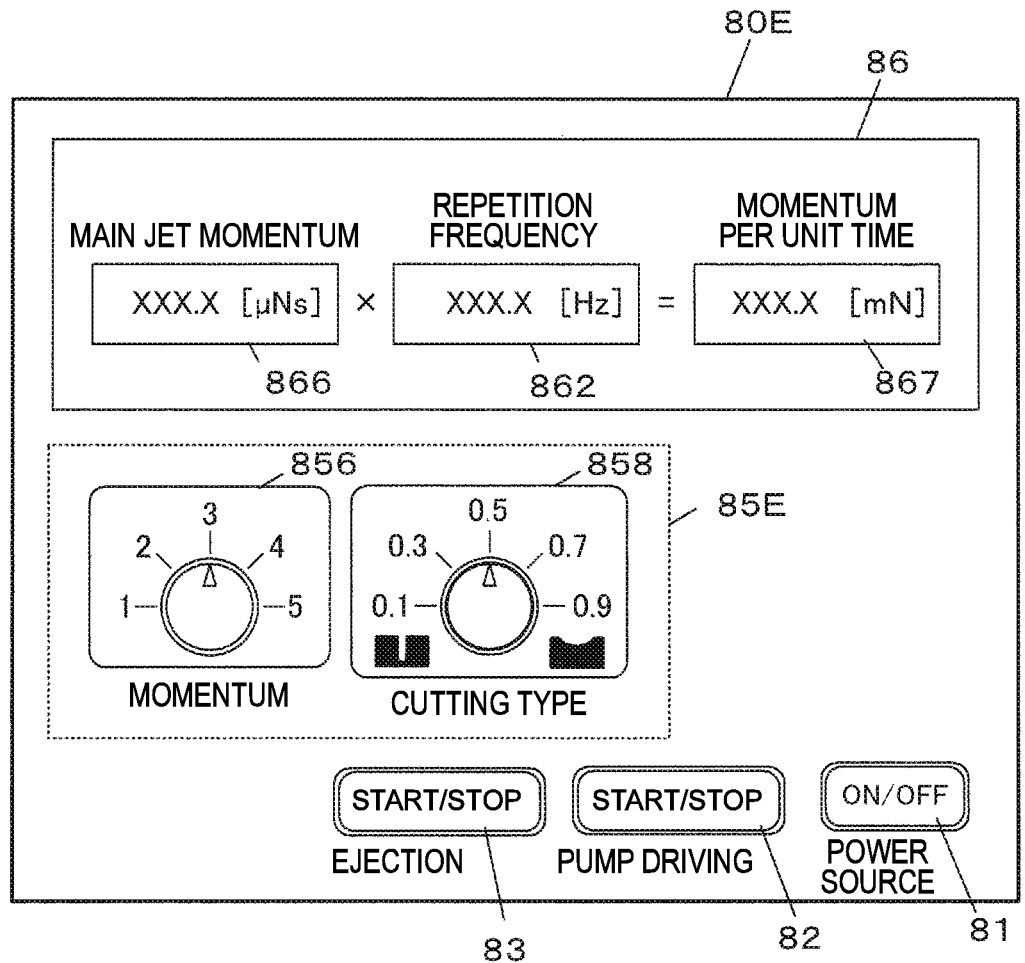
FIG. 53 is a diagram illustrating a configuration example of an operation panel of a liquid ejection control apparatus in a fifth embodiment.

FIG. 53 is a diagram illustrating a configuration example of an operation panel 80E of a liquid ejection control apparatus 70E in the present embodiment. The operation panel 80E is fundamentally the same as that in the first embodiment, but a jet setting operation portion 85E of the present embodiment includes a momentum dial 856 instead of the energy dial 851.

The momentum dial 856 is an operation portion which receives input of an indication value of the momentum P of the main jet, that is, setting of the strength of the main jet. For example, the momentum dial 856 is configured to allow dial positions in five steps, provided with scales such as "1" to "5", to be selected. Momentum indication values are allocated in advance to the respective diameter positions so as to be increased by a predetermined level in proportion to a numerical value of a corresponding scale, for example. The user can operate the strength of the main jet 3 by switching an indication position of the dial. The number of steps of the dial positions is not limited to five steps, and may be set as appropriate, for example, three steps such as "large", "intermediate", and "small", or adjustment may be performed steplessly.

The flat panel display 86 of the present embodiment is provided with a main jet momentum display portion 866 instead of the main jet energy display portion 861, and a per-unit-time-momentum display portion 867 instead of the power display portion 863, in addition to the repetition frequency display portion 862 in order to display various pieces of information regarding a pulsed liquid jet.

The main jet momentum display portion 866 displays momentum [μNs] of a main jet corresponding to a single pulse.

The per-unit-time-momentum display portion 867 momentum [mN] per unit time obtained by multiplying a frequency displayed on the repetition frequency display portion 862 by the momentum displayed on the main jet momentum display portion 866.

Figure 54:
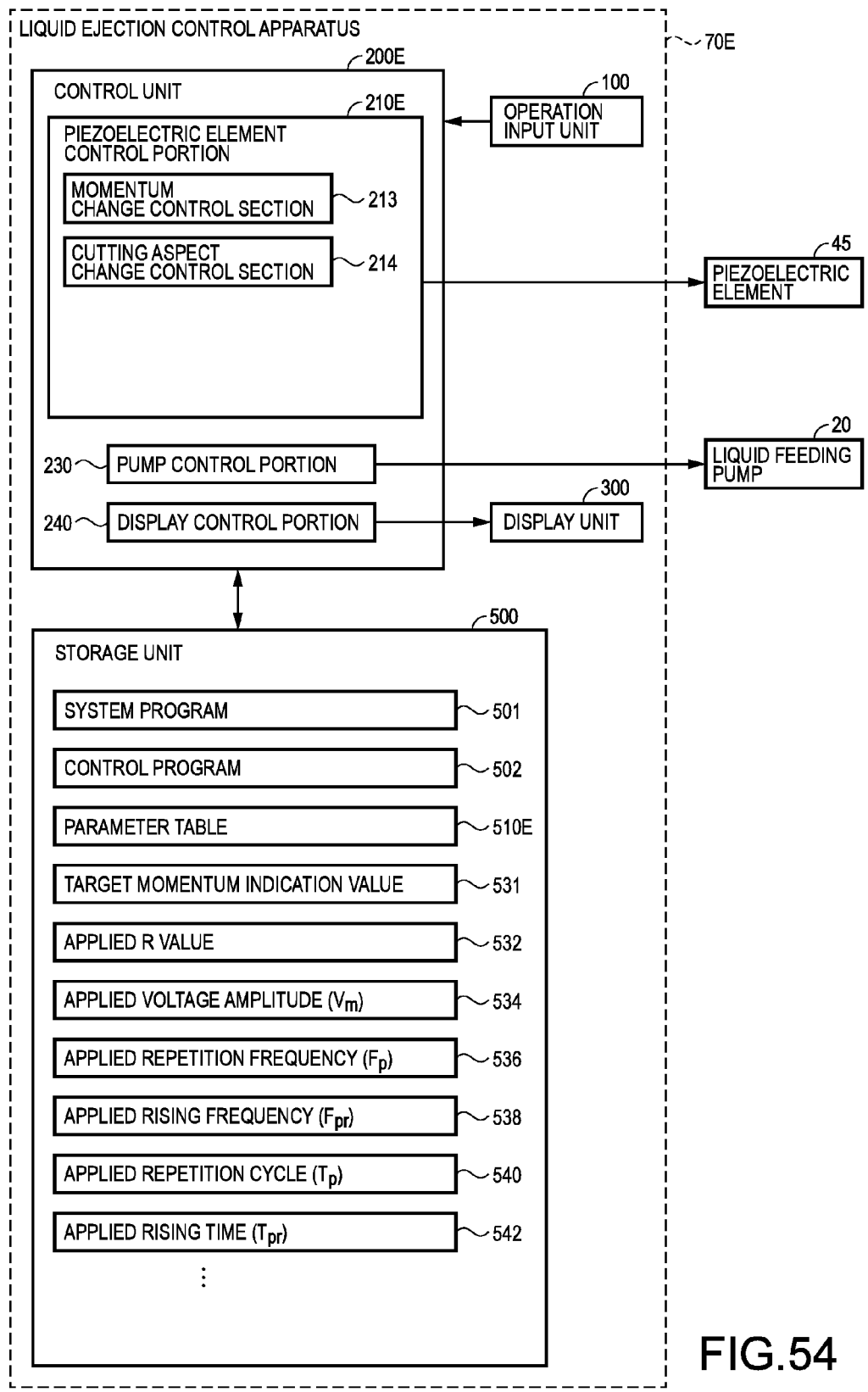
FIG. 54 is a block diagram illustrating a functional configuration example of the liquid ejection control apparatus in the fifth embodiment.

FIG. 54 is a block diagram illustrating a functional configuration example of the liquid ejection control apparatus 70E in the present embodiment.

The liquid ejection control apparatus 70E fundamentally has the same functional configuration as that of the liquid ejection control apparatus 70 of the first embodiment, but a piezoelectric element control portion 210E of a control unit 200E of the present embodiment includes a momentum change control section 213 instead of the energy change control section 212.

The momentum change control section 213 changes the momentum P of the main jet corresponding to a single pulse in response to a momentum setting operation performed by the user. In the present embodiment, a combination of the repetition frequency $F_p$, the rising frequency $F_{pr}$, and the voltage amplitude $V_m$ correlated with a dial position of the momentum dial 856 is determined by referring to a parameter table 510E stored in the storage unit 500. The repetition cycle $T_p$ and the rising time $T_{pr}$ are determined on the basis of the repetition frequency $F_p$ and the rising frequency $F_{pr}$, respectively.

The display control portion 240 of the present embodiment may display the main jet momentum display portion 866 instead of the main jet energy display portion 861, and may display the per-unit-time-momentum display portion 867 instead of the power display portion 863.

The storage unit 500 of the present embodiment stores the parameter table 510E instead of the parameter table 510, and stores a target momentum indication value 531 instead of the target energy indication value 530.

FIG. 55 is a diagram illustrating a data configuration example of the parameter table 510E of the present embodiment. The parameter table 510E is fundamentally the same as the parameter table 510 in the first embodiment, but stores a momentum dial position 520 instead of the energy dial position 511, and stores a momentum indication value 521 instead of the energy indication value 512.

Figure 56:
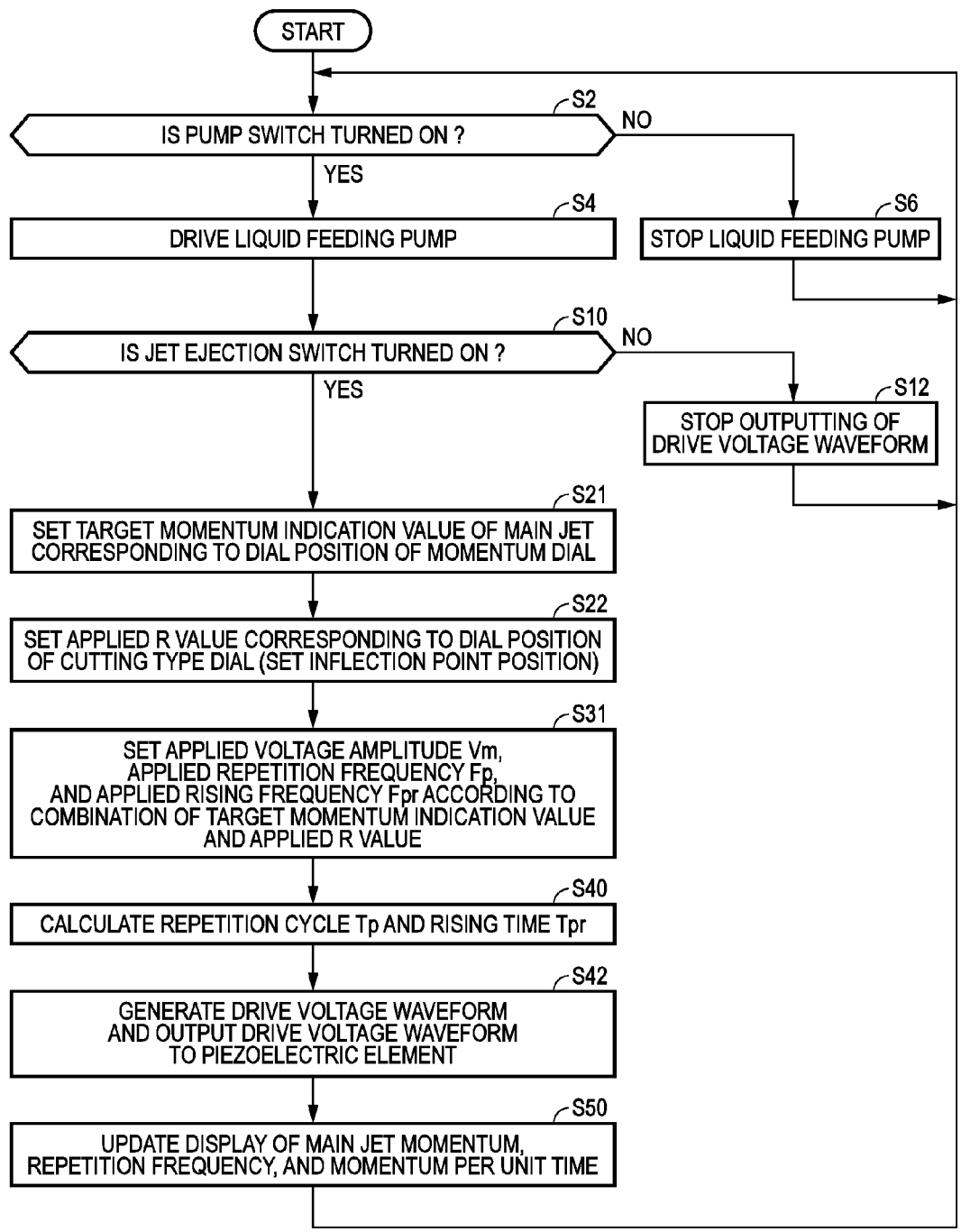
FIG. 56 is a flowchart illustrating a flow of a process performed by a control unit in the fifth embodiment.

FIG. 56 is a flowchart illustrating a flow of a process performed by the control unit 200E of the present embodiment. The flow of the process in the present embodiment is fundamentally the same as the flow of the process in the first embodiment, but step S21 is executed instead of step S20, step S31 is executed instead of step S30, and step S50 is executed instead of step S44.

In other words, after YES is determined in step S10, the control unit 200E sets the target momentum indication value 531 according to a dial position of the momentum dial 856 (step S21).

After step S22, the control unit 200E reads the voltage amplitudes 514, the repetition frequencies 516, and the rising frequencies 518 corresponding to a combination of the target momentum indication value 531 and the applied R value 532 from the parameter table 510E, and sets the values as the applied voltage amplitudes 534, the applied repetition frequencies 536, and the applied rising frequencies 538, respectively (step S31).

After step S42, the control unit 200E updates display of the main jet momentum display portion 866, the repetition frequency display portion 862, and the per-unit-time-momentum display portion 867 on the flat panel display 86 (step S50).

As described above, according to the present embodiment, it is possible to achieve the same effect as in the first embodiment.

Sixth Embodiment

Next, a description will be made of a sixth embodiment to which the invention is applied.

The present embodiment is fundamentally realized in the same manner as the fifth embodiment, but is different in that a user can change the repetition frequency $F_p$. Hereinafter, differences from the fifth embodiment will be mainly described, the same constituent elements as those in the first to fifth embodiments are given the same reference numerals, and repeated description will be omitted.

Figure 57:
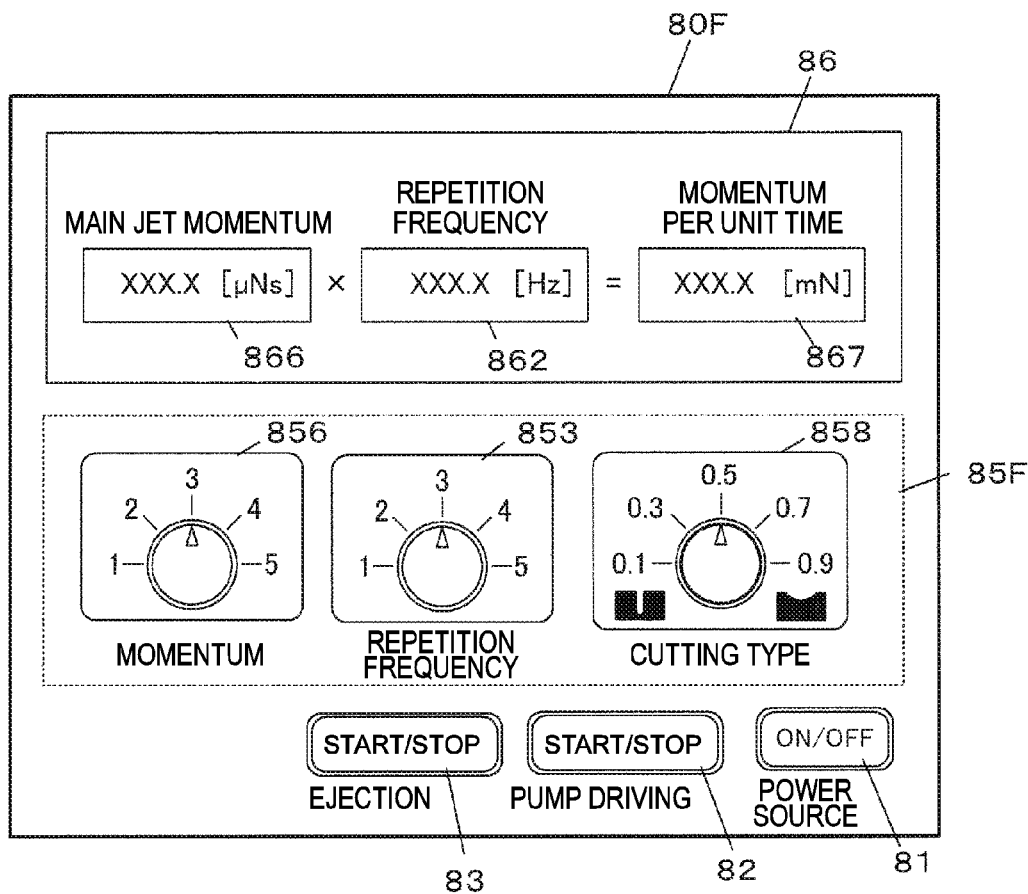
FIG. 57 is a diagram illustrating a configuration example of an operation panel of a liquid ejection control apparatus in a sixth embodiment.

FIG. 57 is a diagram illustrating a configuration example of an operation panel 80F in the present embodiment. The operation panel 80F is fundamentally the same as that in the fifth embodiment, but a jet setting operation portion 85F includes a repetition frequency dial 853 for setting the repetition frequency $F_p$.

Figure 58:
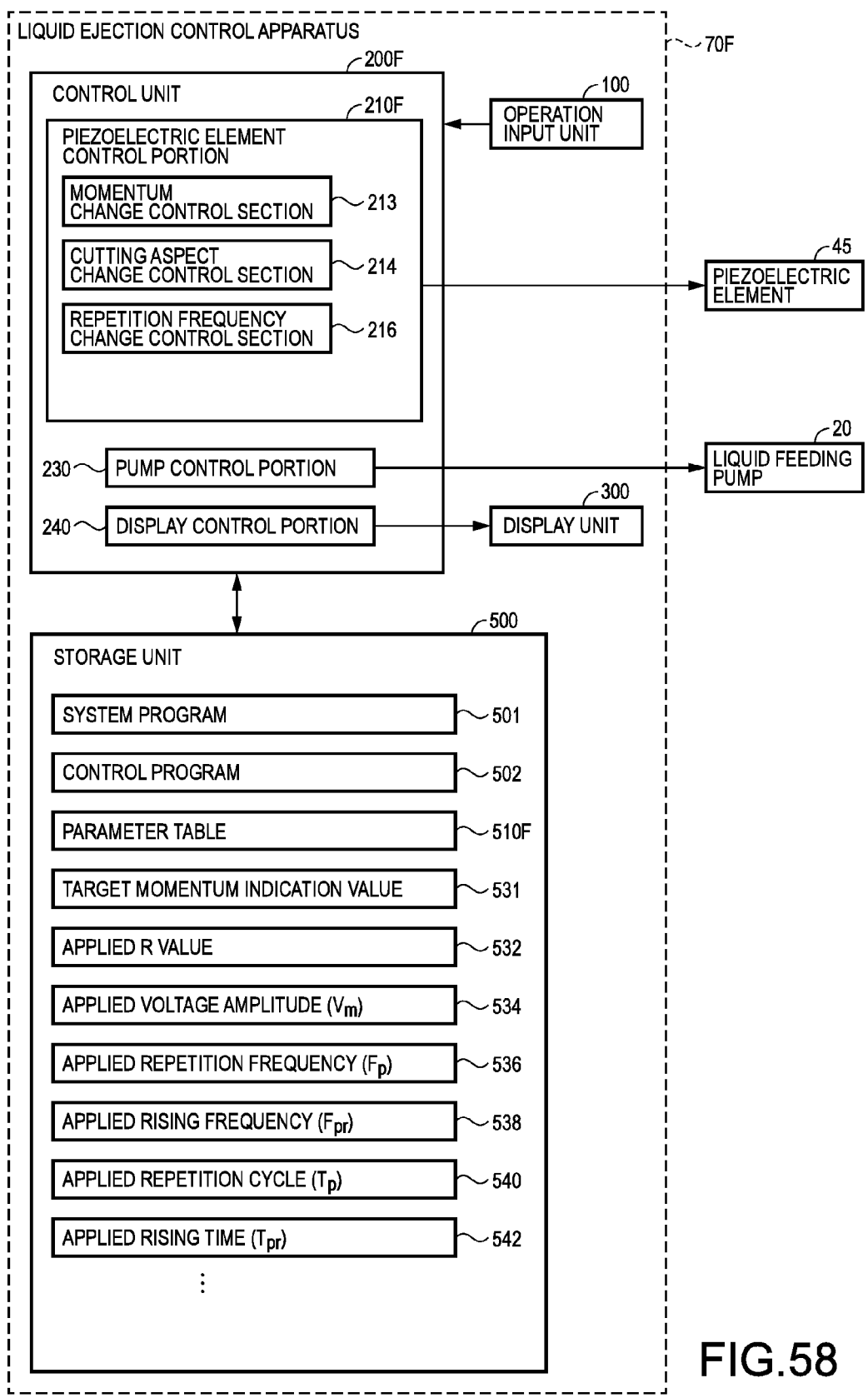
FIG. 58 is a block diagram illustrating a functional configuration example of the liquid ejection control apparatus in the sixth embodiment.

FIG. 58 is a block diagram illustrating a functional configuration example of a liquid ejection control apparatus 70F in the present embodiment. The liquid ejection control apparatus 70F fundamentally has the same functional configuration as that of the liquid ejection control apparatus 70E of the fifth embodiment, but a piezoelectric element control portion 210F of a control unit 200F of the present embodiment includes a repetition frequency change control section 216. The storage unit 500 stores a parameter table 510F.

FIG. 59 is a diagram illustrating a data configuration example of the parameter table 510F of the present embodiment. In the parameter table 510F, the repetition frequency dial position 515 of five types and repetition frequencies 516B are correlated with each momentum dial position 520 (each momentum indication value 521). The cutting type dial positions 513 of five types, the voltage amplitudes 514 of five type, and the rising frequencies 518 of five types are correlated with each combination of two elements such as the momentum dial position 520 (momentum indication value 521) and the repetition frequency dial position 515 (repetition frequencies 516B).

The voltage amplitudes 514 and the rising frequencies 518 of the present embodiment can realize corresponding momentum indication values 521 through combination with corresponding repetition frequencies 516B. Specifically, a graph as illustrated in FIG. 52 is prepared for each repetition frequency 516B, and voltage amplitudes and rising frequencies may be read on the basis of intersections with contour lines of the momentum indication value 521 so as to be set.

Figure 60:
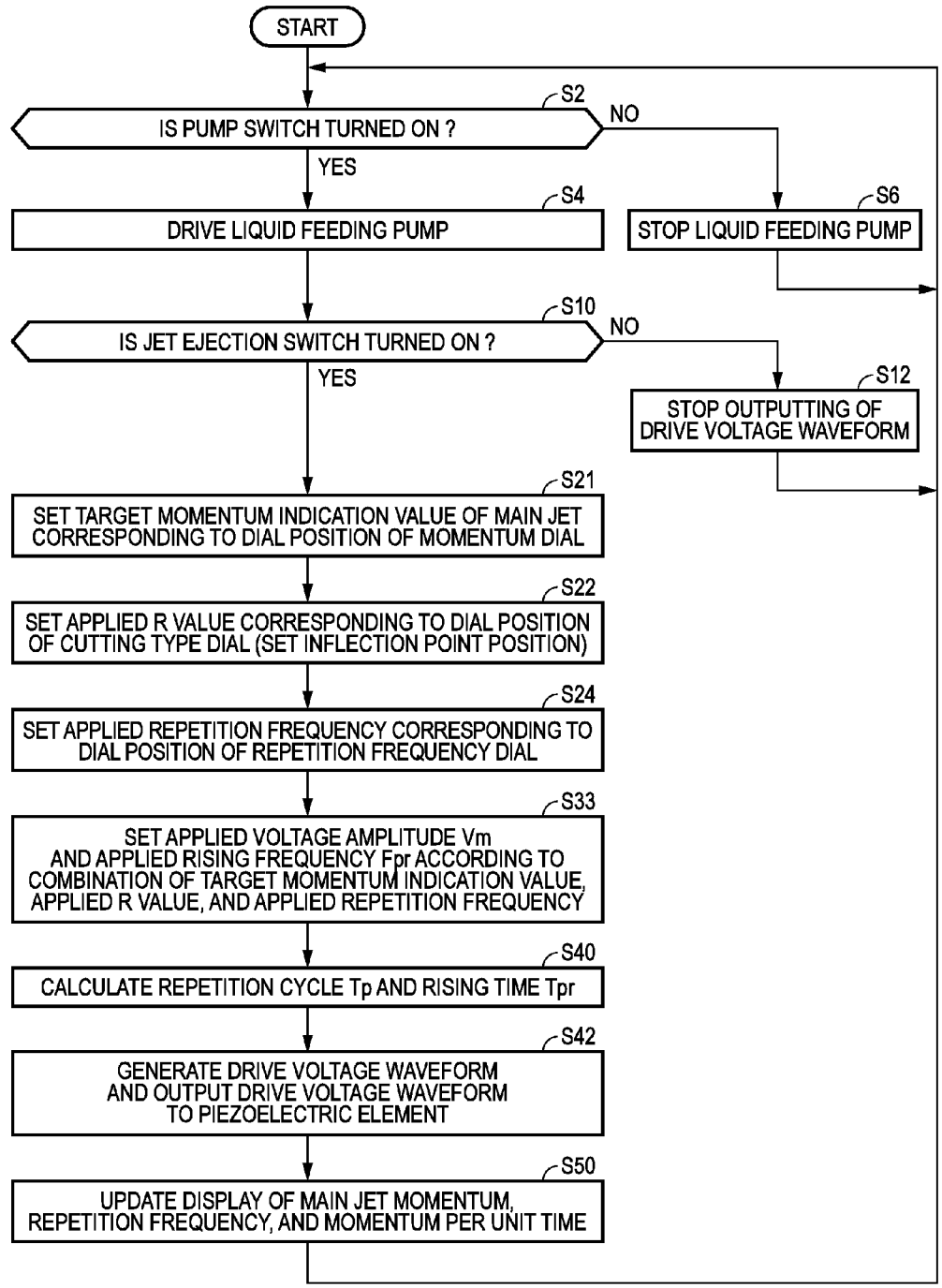
FIG. 60 is a flowchart illustrating a flow of a process performed by a control unit in the sixth embodiment.

FIG. 60 is a flowchart illustrating a flow of a process performed by the control unit 200F of the present embodiment. The flow of the process in the present embodiment is fundamentally the same as the flow of the process in the fifth embodiment, but step S24 (refer to FIG. 42) is executed after step S22, and step S33 is executed instead of step S31.

In step S33, the control unit 200F reads the voltage amplitudes 514 and the rising frequencies 518 corresponding to a combination of three elements such as the target momentum indication value 531, the applied R value 532, and the applied repetition frequency 536 from the parameter table 510F, and sets the values as the applied voltage amplitudes 534 and the applied rising frequencies 538 (step S33).

As described above, according to the present embodiment, it is possible to achieve the same effect as in the fifth embodiment. In addition, it is possible for a user to change a repetition frequency.

Seventh Embodiment

Next, a description will be made of a seventh embodiment to which the invention is applied.

The present embodiment is fundamentally realized in the same manner as the sixth embodiment, but is different in that a user can change the rising frequency $F_{pr}$. Hereinafter, differences from the sixth embodiment will be mainly described, the same constituent elements as those in the first to sixth embodiments are given the same reference numerals, and repeated description will be omitted.

Figure 61:
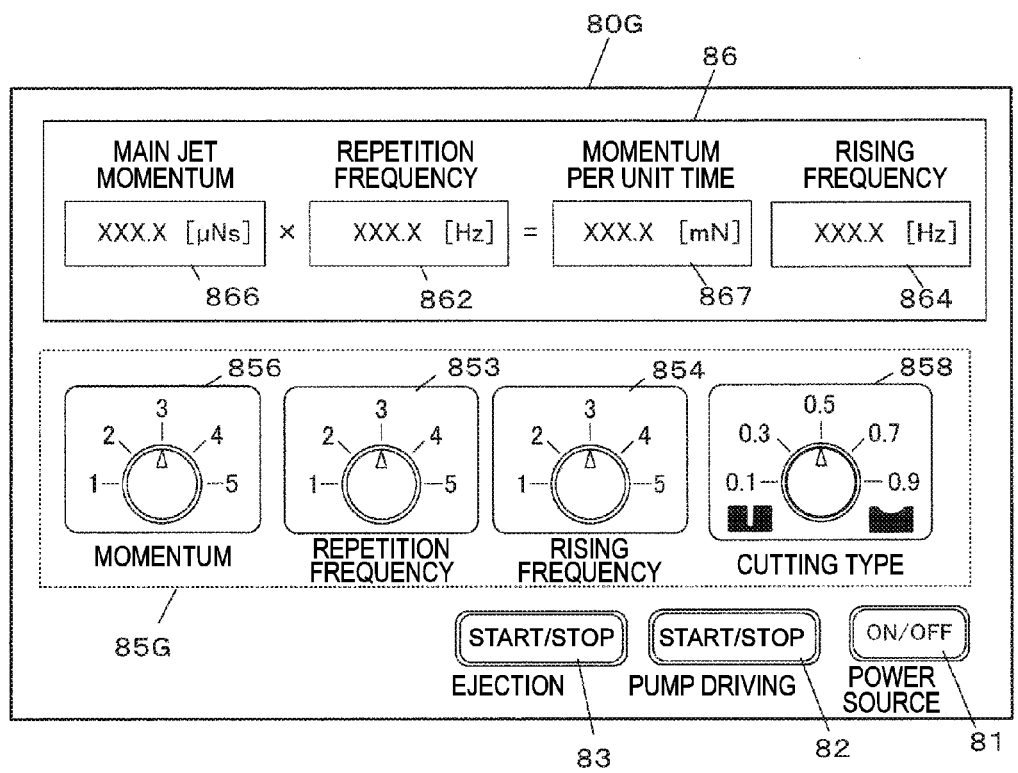
FIG. 61 is a diagram illustrating a configuration example of an operation panel of a liquid ejection control apparatus in a seventh embodiment.

FIG. 61 is a diagram illustrating a configuration example of an operation panel 80G in the present embodiment. The operation panel 80G is fundamentally the same as that in the sixth embodiment, but a jet setting operation portion 85G of the present embodiment includes a rising frequency dial 854 for setting the rising frequency $F_{pr}$, and a rising frequency display portion 864 is included on the flat panel display 86.

Figure 62:
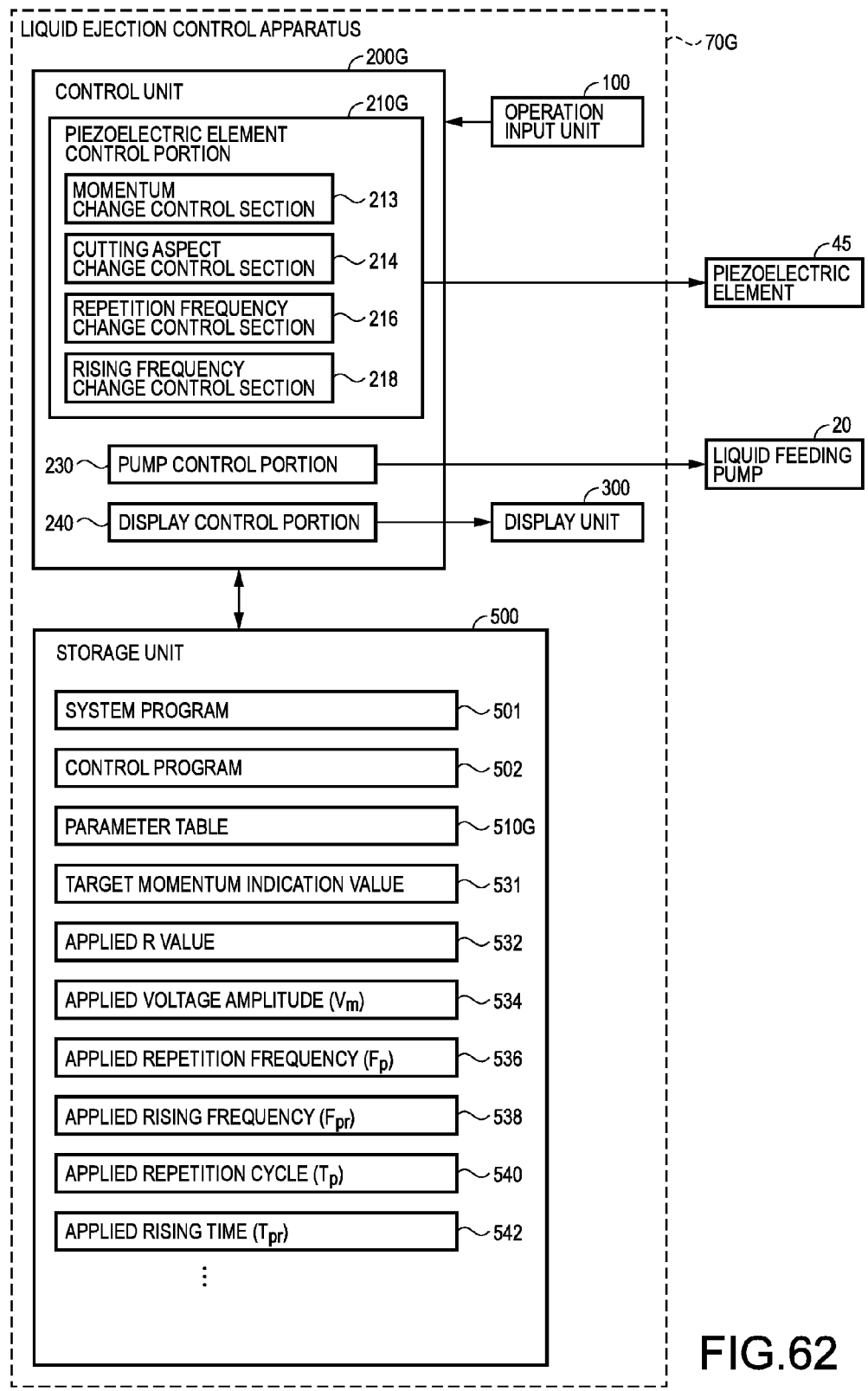
FIG. 62 is a block diagram illustrating a functional configuration example of the liquid ejection control apparatus in the seventh embodiment.

FIG. 62 is a block diagram illustrating a functional configuration example of a liquid ejection control apparatus 70G in the present embodiment. The liquid ejection control apparatus 70G fundamentally has the same functional configuration as that of the liquid ejection control apparatus 70F of the sixth embodiment, but a piezoelectric element control portion 210G of a control unit 200G of the present embodiment includes a rising frequency change control section 218. The display control portion 240 of the present embodiment may display the rising frequency display portion 864 on the flat panel display 86. The storage unit 500 stores a parameter table 510G.

FIG. 63 is a diagram illustrating a data configuration example of the parameter table 510G of the present embodiment. The parameter table 510G stores the rising frequency dial positions 517 of five types and the rising frequencies 518C corresponding thereto in correlation with each combination of two elements such as the momentum indication value 521 and the repetition frequencies 516B. The cutting type dial positions 513 of five types and the voltage amplitudes 514 of five types are stored in correlation with each combination of three elements such as the momentum indication value 521, the repetition frequencies 516B, and the rising frequencies 518C.

The voltage amplitudes 514 of the present embodiment can realize a corresponding momentum indication value 521 by controlling a drive voltage through combination with the momentum indication value 521, the repetition frequencies 516B, and the rising frequencies 518C. When such a value is set, for example, a graph as illustrated in FIG. 52 may be prepared for each repetition frequency 516B, and voltage amplitudes and rising frequencies may be read on the basis of intersections with contour lines of the momentum indication value 521 so as to be set.

Figure 64:
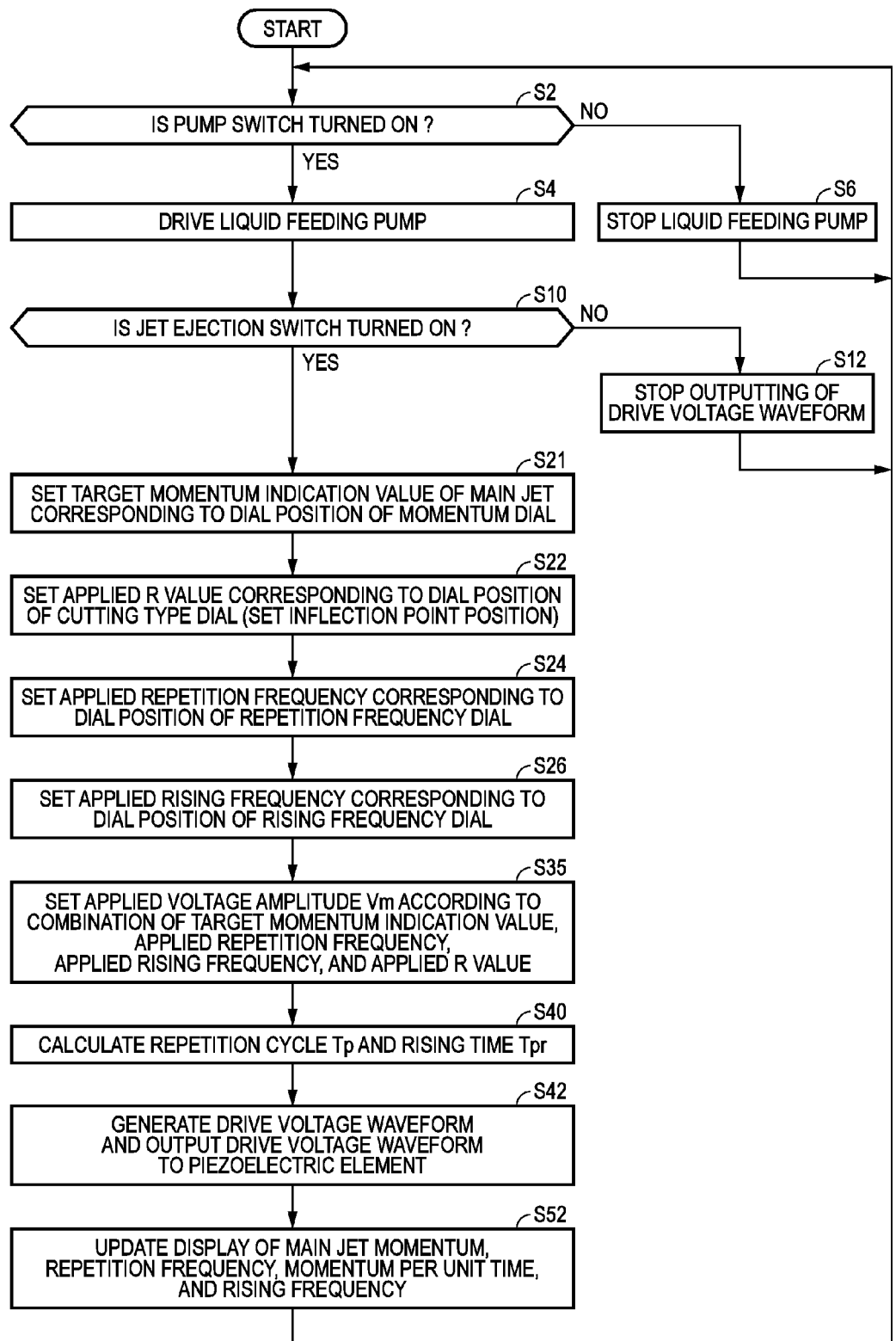
FIG. 64 is a flowchart illustrating a flow of a process performed by a control unit in the seventh embodiment.

FIG. 64 is a flowchart illustrating a flow of a process performed by the control unit 200G of the present embodiment. The flow of the process in the present embodiment is fundamentally the same as the flow of the process in the sixth embodiment, but step S26 (refer to FIG. 46) is executed after step S24, step S35 is executed instead of step S33, and step S52 is executed instead of step S50.

In step S35, the control unit 200G reads the voltage amplitudes 514 corresponding to a combination of four elements such as the target momentum indication value 531, the applied R value 532, the applied repetition frequency 536, and the applied rising frequency 538 from the parameter table 510G, and sets the values as the applied voltage amplitudes 534 (step S35).

In step S52, the control unit 200G updates display of the main jet momentum display portion 866, the repetition frequency display portion 862, the per-unit-time-momentum display portion 867, and the rising frequency display portion 864 on the flat panel display 86 (step S52).

As described above, according to the present embodiment, it is possible to achieve the same effect as in the sixth embodiment. In addition, it is possible for a user to change a rising frequency.

Eighth Embodiment

Next, a description will be made of an eighth embodiment to which the invention is applied.

The present embodiment is fundamentally realized in the same manner as the seventh embodiment. Hereinafter, differences from the seventh embodiment will be mainly described, the same constituent elements as those in the first to seventh embodiments are given the same reference numerals, and repeated description will be omitted.

Figure 65:
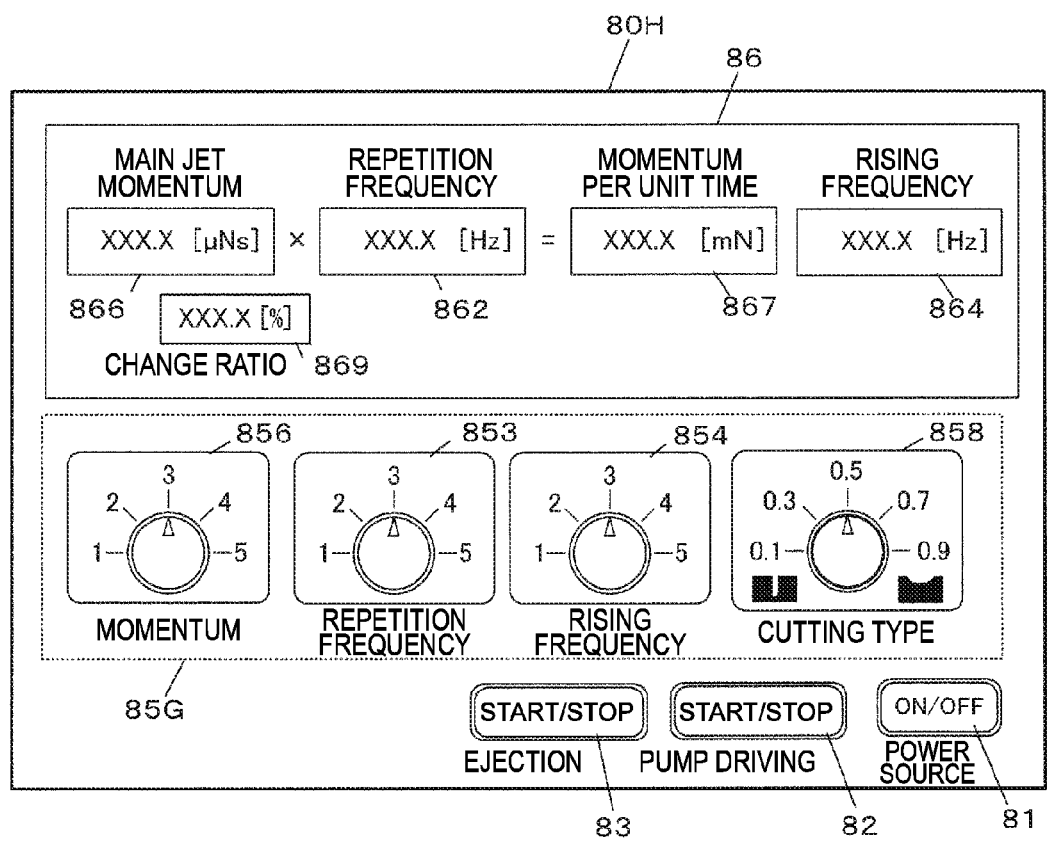
FIG. 65 is a diagram illustrating a configuration example of an operation panel of a liquid ejection control apparatus in an eighth embodiment.

FIG. 65 is a diagram illustrating a configuration example of an operation panel 80H in the present embodiment. The operation panel 80H is fundamentally the same as that in the seventh embodiment, but a momentum change ratio display portion 869 is included on the flat panel display 86.

The energy change ratio display portion 869 displays a change ratio of the momentum P in a case where an R value is changed from a predetermined reference value (a reference position of an inflection point of a rising portion) in a state in which set values of the momentum P, the repetition frequency $F_p$, and the rising frequency $F_{pr}$ are fixed.

Figure 66:
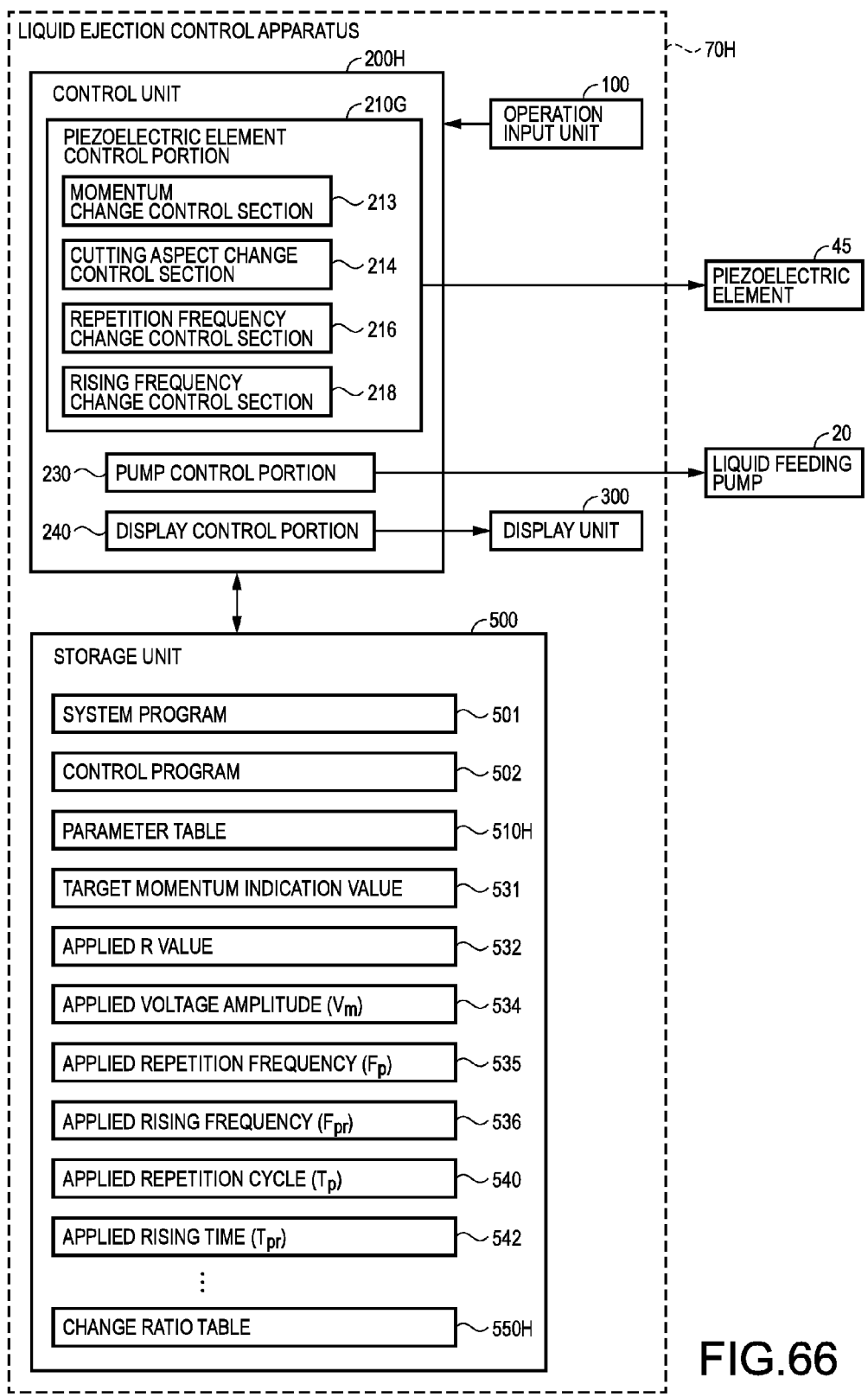
FIG. 66 is a block diagram illustrating a functional configuration example of the liquid ejection control apparatus in the eighth embodiment.

FIG. 66 is a block diagram illustrating a functional configuration example of a liquid ejection control apparatus 70H in the present embodiment. The liquid ejection control apparatus 70H fundamentally has the same functional configuration as that of the liquid ejection control apparatus 70G of the seventh embodiment, but the display control portion 240 of the present embodiment may control display of the momentum change ratio display portion 869. The storage unit 500 of the present embodiment stores a parameter table 510H and a change ratio table 550H.

FIG. 67 is a diagram illustrating a data configuration example of the parameter table 510H of the present embodiment. The parameter table 510H is fundamentally the same as the parameter table 510G in the seventh embodiment, but does not include the cutting type dial positions 513. In other words, the repetition frequency $F_p$, the rising frequency $F_{pr}$, and the voltage amplitude $V_m$ are determined so as to realize the momentum indication value 521 through combination of the three elements.

FIG. 68 is a diagram illustrating a data configuration example of the change ratio table 550H of the present embodiment. The change ratio table 550H stores cutting type dial positions 554 (similar to the cutting type dial positions 513) of five types, main jet momentums 560 of five types, and momentum change ratios 561 of five types for each combination of three elements such as a repetition frequency 551, a rising frequency 552, and a voltage amplitude 553.

The main jet momentums 560 are values of momentum of the main jet 3, determined on the basis of three elements such as corresponding repetition frequency 551, and rising frequency 552 and voltage amplitude 553. The main jet momentums 560 may be obtained in advance through simulation.

The momentum change ratios 561 are ratios of the main jet momentum 560 for the respective cutting type dial positions 554 in a case where the main jet momentum 560 at R=0.5 is used as a reference. R=0.5 is used as a reference, but other R values may be used as references.

Figure 69:
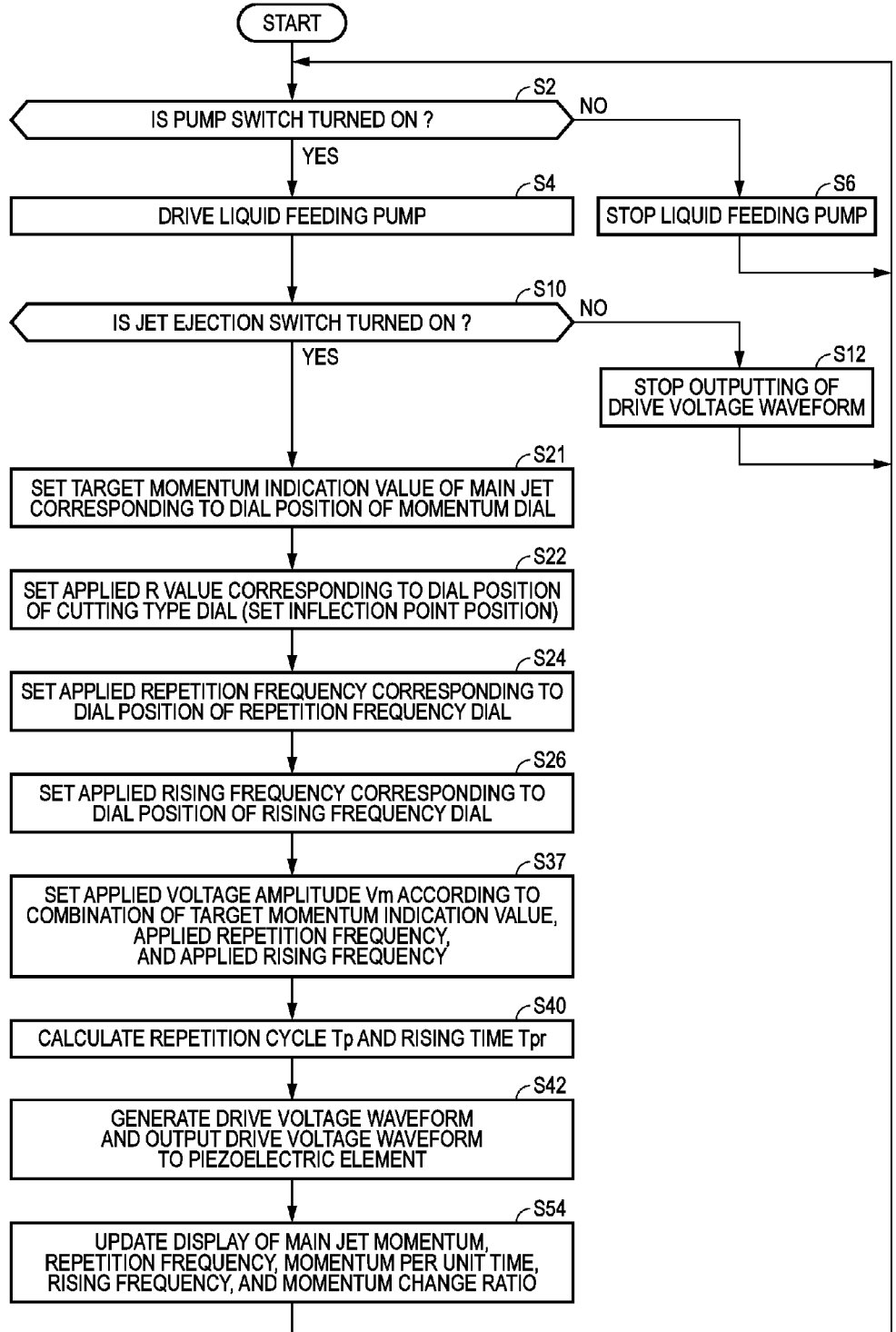
FIG. 69 is a flowchart illustrating a flow of a process performed by a control unit in the eighth embodiment.

FIG. 69 is a flowchart illustrating a flow of a process performed by the control unit 200H of the present embodiment. The flow of the process in the present embodiment is fundamentally the same as the flow of the process in the seventh embodiment, but step S37 is executed instead of step S35, and step S52 is executed instead of step S54.

In other words, after step S26, the control unit 200H reads, from the parameter table 510H, the voltage amplitudes 514 correlated with a combination of three elements such as the momentum indication value 521 conforming to the target momentum indication value 531, the repetition frequency 516B conforming to the applied repetition frequency 536, and the rising frequency 518C conforming to the applied rising frequency 538, and sets the applied voltage amplitudes 534 (step S37).

After step S42, the control unit 200H updates display of the main jet momentum display portion 866, the repetition frequency display portion 862, the per-unit-time-momentum display portion 867, the rising frequency display portion 864, and the momentum change ratio display portion 869 of the flat panel display 86 (step S54).

When the display of the momentum change ratio display portion 869 is updated, the momentum change ratio 561 corresponding to a combination of three elements such as the repetition frequency 551 conforming to the applied repetition frequency 536, the rising frequency 552 conforming to the applied rising frequency 538, and the voltage amplitude 553 conforming to the applied voltage amplitude 534 is read by referring to the change ratio table 550H, and the display of the momentum change ratio display portion 869 is updated by using the read momentum change ratios.

As described above, according to the present embodiment, even in a configuration in which a cutting aspect (R value; inflection point position) is changed after control parameters of a drive voltage waveform are determined and fixed, it is possible to achieve the same effect as in the seventh embodiment. In this case, it is possible to notify a user how much main jet energy is changed due to changing of a cutting aspect.

Modification Examples

As mentioned above, the embodiments to which the invention is applied have been described, but embodiments of the invention are not limited thereto, and an appropriate constituent element may be added, omitted, or changed.

For example, in the above-described embodiments, the energy dial 851, the cutting type dial 858, the repetition frequency dial 853, the rising frequency dial 854, and the momentum dial 856 have been exemplified as a click type dial for performing stepwise changing, but may be configured of a volume type dial. In other words, the parameter values allocated to each dial may be set and operated steplessly. Specifically, for example, in the energy dial 851, in a case where a dial position between the scales is selected, the energy indication values 512 correlated with dial positions of the preceding and following scales may be read, and may be interpolated through linear interpolation or polynomial interpolation so that an energy indication value corresponding to the present selected dial position is specified.

In the above-described embodiments, a drive voltage waveform is generated on the basis of Equation (18), preferably, Equation (19) (as specific examples, Equation (21) or Equation (23)), but waveform data regarding drive voltage waveforms which can be taken may be prepared in advance, and waveform data conforming to a parameter value selected by a user may be read and reproduced. Specifically, in the first embodiment, there may be a configuration in which a fundamental drive voltage waveform of one cycle is generated in advance for each combination of two elements such as the target energy indication value 530 and the applied R value 532, and is prepared in the storage unit 500 as waveform data correlated with the combination. In the second embodiment, waveform data may be prepared for each combination of three elements such as the target energy indication value 530, the applied R value 532, and the applied repetition frequency 536.

In the above-described embodiments, a $T_r/T$ value (refer to FIG. 4; a ratio of the flow velocity rising time $T_r$ to the duration T in the main jet flow velocity waveform) may be used as a "main jet flow velocity rising time position index $R^*$" instead of an R value.

In this configuration, table data defining a correspondence relationship between an R value and an $R^*$ value ($T_r/T$) is separately prepared and is stored in the storage unit 500. In the process step of calculating the applied R value 532, the $R^*$ value may be converted into the R value on the basis of the table data, and the R value may be set.

The entire disclosure of Japanese Patent Application No. 2015-185396 filed Sep. 18, 2015 is expressly incorporated by reference herein.

What is claimed is:

1. A liquid ejection control apparatus which controls a drive voltage waveform applied to a piezoelectric element so as to control ejection of a pulsed liquid jet, the apparatus comprising:

a first operation unit that receives input of an index value for setting a position of an inflection point in a rising portion of the drive voltage waveform; and a control unit that sets the position of the inflection point in the rising portion of the drive voltage waveform according to the index value so as to control changing of the drive voltage waveform.

2. The liquid ejection control apparatus according to claim 1, wherein the control unit moves the inflection point along a line segment connecting a rising start point to a maximum voltage in the rising portion so as to set the position of the inflection point corresponding to the index value.

3. A liquid ejection system comprising:

the liquid ejection control apparatus according to claim 2;

a liquid ejection device that ejects the pulsed liquid jet; and a liquid feeding pump that feeds a liquid to the liquid ejection device.

4. The liquid ejection control apparatus according to claim 1, further comprising:

a second operation unit that receives input of an indication value of momentum or kinetic energy of the pulsed liquid jet, wherein the control unit sets the position of the inflection point according to the index value, and controls changing of the drive voltage waveform so that the indication value is obtained.

5. The liquid ejection control apparatus according to claim 4, wherein the control unit controls amplitude of the drive voltage waveform so that the indication value is obtained.

6. A liquid ejection system comprising:

the liquid ejection control apparatus according to claim 5;

a liquid ejection device that ejects the pulsed liquid jet; and a liquid feeding pump that feeds a liquid to the liquid ejection device.

7. The liquid ejection control apparatus according to claim 4, wherein the control unit controls any one of time, a rising frequency, and a repetition frequency related to rising of the drive voltage waveform so that the indication value is obtained.

8. A liquid ejection system comprising:

the liquid ejection control apparatus according to claim 7;

a liquid ejection device that ejects the pulsed liquid jet; and a liquid feeding pump that feeds a liquid to the liquid ejection device.

9. A liquid ejection system comprising:

the liquid ejection control apparatus according to claim 4;

a liquid ejection device that ejects the pulsed liquid jet; and a liquid feeding pump that feeds a liquid to the liquid ejection device.

10. The liquid ejection control apparatus according to claim 1, wherein ejection control of the pulsed liquid jet is performed so that momentum of the pulsed liquid jet is equal to or more than 2 nanonewton seconds (nNs) and is equal to or less than 2 millinewton seconds (mNs), or kinetic energy of the pulsed liquid jet is equal to or more than 2 nanojoules (nJ) and is equal to or less than 200 millijoules (mJ).

11. A liquid ejection system comprising:

the liquid ejection control apparatus according to claim 10;

a liquid ejection device that ejects the pulsed liquid jet; and a liquid feeding pump that feeds a liquid to the liquid ejection device.

12. The liquid ejection control apparatus according to claim 1, wherein ejection control of the pulsed liquid jet is performed so that living tissue is cut.

13. A liquid ejection system comprising:

the liquid ejection control apparatus according to claim 12;

a liquid ejection device that ejects the pulsed liquid jet; and a liquid feeding pump that feeds a liquid to the liquid ejection device.

14. A liquid ejection system comprising:

the liquid ejection control apparatus according to claim 1;

a liquid ejection device that ejects the pulsed liquid jet; and a liquid feeding pump that feeds a liquid to the liquid ejection device.

15. A control method of controlling a drive voltage waveform applied to a piezoelectric element so as to control ejection of a pulsed liquid jet, the method comprising:

receiving input of an index value for setting a position of an inflection point in a rising portion of the drive voltage waveform; and setting the position of the inflection point in the rising portion of the drive voltage waveform according to the index value so as to control changing of the drive voltage waveform.

* * * * *